(12) United States Patent
Mohapatra et al.

(10) Patent No.: US 10,184,942 B2
(45) Date of Patent: Jan. 22, 2019

(54) NATRIURETIC PEPTIDE RECEPTOR AS A BIOMARKER FOR DIAGNOSIS AND PROGNOSIS OF CANCER

(75) Inventors: Subhra Mohapatra, Lutz, FL (US); Shyam Mohapatra, Lutz, FL (US)

(73) Assignee: UNIVERSITY OF SOUTH FLORIDA, Tampa (*) Notice: Subject to any disclaimer, the term of this patent is extended or adjusted under 35 U.S.C. 154(b) by 492 days.

(21) Appl. No.: 13/422,880

(22) Filed: Mar. 16, 2012

(65) Prior Publication Data

US 2012/0270923 A1 Oct. 25, 2012

Related U.S. Application Data

(60) Provisional application No. 61/453,646, filed on Mar. 17, 2011.

(51) Int. Cl.
| | |
|---|---|
| G01N 33/574 | (2006.01) |
| C07K 16/28 | (2006.01) |
| C12Q 1/6886 | (2018.01) |
| C12N 15/113 | (2010.01) |

(52) U.S. Cl.
CPC ..... *G01N 33/57415* (2013.01); *C07K 16/286* (2013.01); *C12N 15/1138* (2013.01); *C12Q 1/6886* (2013.01); *G01N 33/5743* (2013.01); *G01N 33/57419* (2013.01); *G01N 33/57434* (2013.01); *G01N 33/57438* (2013.01); *G01N 33/57446* (2013.01); *G01N 33/57492* (2013.01); *C07K 2317/34* (2013.01); *C12N 2310/11* (2013.01); *C12N 2310/12* (2013.01); *C12N 2310/14* (2013.01); *C12Q 2600/158* (2013.01); *G01N 2333/72* (2013.01); *G01N 2800/50* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | |
|---|---|---|
| 4,753,945 A | 6/1988 | Gilbard et al. |
| 4,957,735 A | 9/1990 | Huang |
| 5,013,556 A | 5/1991 | Woodle et al. |
| 5,043,164 A | 8/1991 | Huang et al. |
| 5,087,617 A | 2/1992 | Smith |
| 5,093,246 A | 3/1992 | Cech et al. |
| 5,116,742 A | 5/1992 | Cech et al. |
| 5,135,917 A | 8/1992 | Burch |
| 5,144,019 A | 9/1992 | Rossi et al. |
| 5,168,053 A | 12/1992 | Altman et al. |
| 5,176,996 A | 1/1993 | Hogan et al. |
| 5,180,818 A | 1/1993 | Cech et al. |
| 5,190,931 A | 3/1993 | Inouye |
| 5,272,262 A | 12/1993 | Rossi et al. |
| 5,352,770 A | 10/1994 | Matsuo |
| 5,545,614 A | 8/1996 | Stamler et al. |
| 5,595,756 A | 1/1997 | Bally et al. |
| 5,602,143 A | 2/1997 | Krauss |
| 5,625,056 A | 4/1997 | Genieser et al. |
| 5,646,032 A | 7/1997 | ter Meulen et al. |
| 5,665,861 A | 9/1997 | Forssmann et al. |
| 5,686,101 A | 11/1997 | Tagawa et al. |
| 5,691,310 A | 11/1997 | Vesely |
| 5,705,187 A | 1/1998 | Unger |
| 5,817,856 A | 10/1998 | Tirosh et al. |
| 5,820,873 A | 10/1998 | Choi et al. |
| 5,840,341 A | 11/1998 | Watts et al. |
| 5,858,694 A | 1/1999 | Piazza et al. |
| 6,004,755 A | 12/1999 | Wang |
| 6,013,630 A | 1/2000 | Shimkets |
| 6,028,055 A | 2/2000 | Lowe et al. |
| 6,040,138 A | 3/2000 | Lockhart et al. |
| 6,184,037 B1 | 2/2001 | Rolland et al. |
| 6,506,559 B1 | 1/2003 | Fire et al. |
| 6,528,245 B2 | 3/2003 | Sanchez-Ramos et al. |
| 6,943,147 B2 | 9/2005 | Vesely |
| 7,022,828 B2 | 4/2006 | McSwiggen |
| 7,354,908 B2 | 4/2008 | Mohapatra et al. |
| 7,488,713 B2 | 2/2009 | Vesely |
| 7,595,303 B1 | 9/2009 | Mohapatra et al. |
| 7,655,772 B2 | 2/2010 | Mohapatra |
| 7,825,092 B2 | 11/2010 | Vesely |
| 7,846,900 B2 | 12/2010 | Vesely |
| 8,071,560 B2 | 12/2011 | Mohapatra et al. |
| 8,148,114 B2 | 4/2012 | Mohapatra |
| 8,604,019 B2 | 12/2013 | Liang et al. |
| 2001/0027181 A1 | 10/2001 | Kitakaze |
| 2002/0094326 A1 | 7/2002 | Donahue et al. |
| 2002/0146821 A1 | 10/2002 | Sanchez-Ramos et al. |
| 2002/0193579 A1 | 12/2002 | Usman et al. |
| 2003/0069186 A1 | 4/2003 | Burnett et al. |
| 2003/0073628 A1 | 4/2003 | Shailubhai et al. |

(Continued)

FOREIGN PATENT DOCUMENTS

| | | |
|---|---|---|
| WO | WO 1999/32619 A1 | 7/1999 |
| WO | WO 2000/71576 A2 | 11/2000 |

(Continued)

OTHER PUBLICATIONS

Vine, K.L. et al. "In vitro cytotoxity evaluation of some substituted isatin derivatives" Bioorganic & Medicinal Chemistry, 2007, 15(2):931-938.

(Continued)

*Primary Examiner* — Alana Harris Dent
(74) *Attorney, Agent, or Firm* — Saliwanchik, Lloyd & Saliwanchik

(57) ABSTRACT

The invention pertains to biomarkers for clinical detection of malignancies, especially for early detection of cancers. More specifically, this invention pertains to the role of Natriuretic Peptide Receptor A (NPRA) in cancer (e.g., tumor) progression. Thus, the invention includes materials and methods for the detection and prognosis of malignancies. The invention also pertains to methods for treating malignancies.

16 Claims, 26 Drawing Sheets

Specification includes a Sequence Listing.

(56) References Cited

U.S. PATENT DOCUMENTS

| | | |
|---|---|---|
| 2003/0105000 A1 | 6/2003 | Pero et al. |
| 2003/0138793 A1 | 7/2003 | Su et al. |
| 2003/0147943 A1 | 8/2003 | Luo et al. |
| 2003/0204063 A1 | 10/2003 | Gravel et al. |
| 2003/0215528 A1 | 11/2003 | Graham et al. |
| 2004/0002458 A1 | 1/2004 | Seilhamer et al. |
| 2004/0067889 A1 | 4/2004 | Belenky et al. |
| 2004/0138134 A1 | 7/2004 | Golembo et al. |
| 2004/0146549 A1 | 7/2004 | Ben-Sasson et al. |
| 2004/0171550 A1 | 9/2004 | Backstrom et al. |
| 2004/0203081 A1 | 10/2004 | James et al. |
| 2004/0213782 A1 | 10/2004 | Wax |
| 2004/0224903 A1 | 11/2004 | Berry et al. |
| 2004/0229784 A1 | 11/2004 | Vesely |
| 2004/0258687 A1 | 12/2004 | Waldman et al. |
| 2004/0266673 A1 | 12/2004 | Bakis et al. |
| 2005/0008617 A1 | 1/2005 | Chen et al. |
| 2005/0014287 A1 | 1/2005 | Friese et al. |
| 2005/0014289 A1 | 1/2005 | Parsons et al. |
| 2005/0176641 A1 | 8/2005 | Bakis et al. |
| 2005/0209139 A1 | 9/2005 | Vesely |
| 2005/0266093 A1 | 12/2005 | Mohapatra |
| 2005/0272650 A1 | 12/2005 | Mohapatra |
| 2005/0287118 A1 | 12/2005 | Tian et al. |
| 2006/0014689 A1 | 1/2006 | Vesely |
| 2006/0019256 A1 | 1/2006 | Clark et al. |
| 2006/0068405 A1 | 3/2006 | Diber et al. |
| 2006/0089324 A1 | 4/2006 | Bank |
| 2006/0110359 A1 | 5/2006 | Sanchez-Ramos et al. |
| 2006/0239971 A1 | 10/2006 | Mohapatra |
| 2006/0276382 A1 | 12/2006 | Mohapatra |
| 2007/0009951 A1 | 1/2007 | Mohapatra et al. |
| 2007/0036867 A1 | 2/2007 | Mohapatra et al. |
| 2007/0116767 A1 | 5/2007 | Mohapatra |
| 2007/0178075 A1 | 8/2007 | Chaudhry et al. |
| 2007/0238676 A1 | 10/2007 | Mohapatra et al. |
| 2007/0265204 A1 | 11/2007 | Mohapatra et al. |
| 2008/0023325 A1 | 1/2008 | Mohapatra et al. |
| 2008/0039394 A1 | 2/2008 | Vesely |
| 2008/0070858 A1 | 3/2008 | Mohapatra |
| 2008/0214437 A1 | 9/2008 | Mohapatra et al. |
| 2009/0062206 A1 | 3/2009 | Vesely |
| 2009/0123439 A1* | 5/2009 | Yun et al. ............ 424/93.21 |
| 2009/0170196 A1 | 7/2009 | Vesely |
| 2009/0176706 A1 | 7/2009 | Mohapatra |
| 2009/0215636 A1* | 8/2009 | Krizman et al. ............ 506/7 |
| 2009/0280143 A1 | 11/2009 | Mohapatra et al. |
| 2010/0260725 A1 | 10/2010 | Mohapatra et al. |
| 2011/0034386 A1 | 2/2011 | Vesely |
| 2011/0039777 A1 | 2/2011 | Vesely |

FOREIGN PATENT DOCUMENTS

| | | |
|---|---|---|
| WO | WO 2001/68836 A3 | 9/2001 |
| WO | WO 2001/75164 A3 | 10/2001 |
| WO | WO 2001/92513 A1 | 12/2001 |
| WO | WO 2004/011498 A3 | 2/2004 |
| WO | WO 2004/022003 A3 | 3/2004 |
| WO | WO 2004/022579 A3 | 3/2004 |
| WO | WO 2004/083236 A3 | 9/2004 |
| WO | WO 2005/094420 A3 | 10/2005 |
| WO | WO 2006/026536 A3 | 3/2006 |
| WO | WO 2007/127487 A2 | 11/2007 |
| WO | WO 2007/130627 A3 | 11/2007 |
| WO | WO 2008/157834 A1 | 12/2008 |
| WO | WO 2009/042173 A1 | 3/2009 |
| WO | WO 2009/073527 A2 | 6/2009 |

OTHER PUBLICATIONS

Vita, M. et al. "The Myc oncoprotein as a therapeutic target for human cancer" Seminars in Cancer Biology, 2006, 16:318-330.

Vlasuk, G.P. et al. "Structure and analysis of the bovine atrial natriuretic peptide precursor gene" Biochem. Biophys. Res. Commun., 1986, 136(1):396-403.

Voet, D. et al. editors, "Section 9-3: Abnormal Hemoglobins" Biochemistry, 2nd Edition; New York: John Wiley & Sons, 1995, pp. 235-241.

Wang, W. et al. "AlbuBNP, a recombinant B-type natriuretic peptide and human serum albumin fusion hormone, as a long-term therapy of congestive heart failure" Pharm. Res., 2004, 21(11):2105-2111.

Wang, X. et al. "siRNA Targeting the Natriuretic Peptide Receptor-A Prevents Airway Inflammation in a Mouse Model of Allergic Asthma" Journal of Allergy and Clinical Immunology, Jan. 2007, 119(1):S131, abstract 515.

Weiss, W.J. et al. "Inhalation efficacy of RFI-641 in an African green monkey model of RSV infection" *Journal of Medical Primatology*, 2003, 32:82-88.

Weller, M, et al. "Predicting Chemoresistance in Human Malignant Glioma Cells: The Role of Molecular Genetic Analyses" Int. J. Cancer (Pred. Oncol.), 1998, pp. 640-644.

White, R.E. et al. "Potassium channel stimulation by natriuretic peptides through cGMP-dependent dephosphorylation" Nature, Jan. 21, 1993, pp. 263-266, vol. 361.

Wigle, D.A. et al. "ANP secretion from small cell lung cancer lines: a potential model of ANP release" Am J Physiol Heart Circ Physiol, 1995, pp. H1869-H1874, vol. 268, abstract.

Winder, D.G. et al. "ERK plays a Regulatory Role in Induction of LTP by Theta Frequency Stimulation and Its Modulation by β-adrenergic Receptors" *Neuron*, Nov. 1999, 24:715-726.

Winnepennickx, V. et el. "Gene Expression Profiling of Primary Cutaneous Melanoma and Clinical Outcome" Journal of the National Cancer Institute, Apr. 5, 2006, 98(7):472-482.

Winquist, R. et al. "Atrial natriuretic factor elicits an endothelium-independent relaxation and activates particulate guanylate cyclase in vascular smooth muscle" Proc. Natl. Acad. Sci. USA, 1984, 81:7661-7664.

Winters, C.J. et al. "The N-Terminus and a 4,000-MW Peptide From the Midportion of the N-Terminus of the Atrial Natriuretic Factor Prohormone Each Circulate in Humans and Increase in Congestive Heart Failure" Circulation, 1989, pp. 438-449, vol. 80.

U.S. Appl. No. 10/526,584, Oct. 11, 2005, Mohapatra.

"atrial natriuretic factor receptor A", MeSH results, accessed http://www.ncbi.nlm.nih.gov/mesh on Dec. 3, 2009, pp. 1-2.

"Designing Custom Peptides" from Technical Bulletin of SIGMA Genosys, http://www.sigma-genosys.com/peptide_design.asp; accessed Dec. 16, 2004, 2 pages.

Abadi, A.H. et al. "Synthesis of 3-substituted-2-oxoindole analogues and their evaluation ans kinase inhibitors, anticancer and antiangiogenic agents" European Journal of Medicinal Chemistry, 2006, 41(3):296-305.

Abbey, S. and Potter, L. "Lysophosphatidic acid inhibits C-type natriuretic peptide activation of guanylyl cyclase-B" Endocrinology, 2003, 144:240-246.

Advisory Action dated Oct. 15, 2008 in U.S. Appl. No. 11/059,814, filed Feb. 17, 2005.

Ahn, K.S. et al. "Simvastatin Potentiates TNF-α-Induced Apoptosis through the Down-Regulation of NF-$_K$B-Dependent Antiapoptotic Gene Products: Role of I$_K$Bα Kinase and TGF-β-Activated Kinase-1" Journal of Immunology, 2007, 178:2507-2516.

Ala, ACRC "Clinical Trial of Low-Dose Theophylline and Montelukast in Patients with Poorly Controlled Asthma" *American Journal of Respitory and Critical Care Medicine*, 2007, 175:235-242.

Ala, ACRC The Safety of Inactivated Influenza Vaccine in Adults and Children With Asthma *New England Journal of Medicine*, 2001, 345:1529-1536.

Allen, T.M. et al. "Large unilamellar liposomes with low uptake into the reticuloendothelial system" FEBS Letters, 1987, 223:42-46.

Angus, R.M. et al. "Effect of inhaled atrial natriuretic peptide on methacholine induced bronchoconstriction in asthma" Clin Exp Allergy,1994, 24:784-788.

Angus, R.M. et al. "Effect of inhaled atrial natriuretic peptide and a neutral endopeptidase inhibitor on histamine-induced bronchoconstriction" Am. J. Respir. Crit. Care Med., 1995, 151:2003-2005.

(56) References Cited

OTHER PUBLICATIONS

Arenberg, D. "Chemokines in the Biology of Lung Cancer" Journal of Thoracic Oncology, 2006, 1(4):287-288.
Ashworth, T. et al. "Cutting Edge: TFII-I Controls B Cell Proliferation via Regulating NF-$_K$B" Journal of Immunology, 2007, 178:2631-2635.
ATCC No. CCL-248 (T84, 1984), 2 pages.
Auerbach, R. et al. "Angiogenesis assays, Problems and Pitfalls" Cancer and Metastasis Reviews 2000, 19: 167-172.
Baldini, P.M. et al. "Decrease of polyamine levels and enhancement of transglutaminase activity in selective reductionof B16-F10 melanoma cell proliferation induced by atrial natriuretic peptide" Melanoma Research, 2006, 16:501-507.
Bass, B.L. "RNA interference: The short answer" Nature, 2001, 411:428-429.
Benjamin, B.A. et al. "Effect of proANF-(31-67) on sodium excretion in conscious monkeys" Am J Physiol Regul Integr Comp Physiol, 1995, pp. R1351-1355, vol. 269, abstract.
Benson, J.D. et al. "Validating cancer drug targets" Nature, May 2006, 441:451-456.
Berendsen, H.J.C. "A Glimpse of the Holy Grail?" Science, Oct. 23, 1998, 282(5389):642-643.
Bernstein, E. et al. "Role for a bidentate ribonuclease in the initiation step of RNA interference" Nature, Jan. 2001, 409:363-366.
Bernstein, E. et al. "The rest is silence" RNA, 2001, 7:1509-1521.
Bliss, D. etal. "Expression of the atrial natriuretic factor gene in small cell lung cancer tumors and tumor cell lines" J Natl Can Inst, 1990, 82:305-310.
Boiteau, R. et al. "Increase in atrial natriuretic factor (ANF) in acute severe asthma (ASA)" Am Rev Res Dis., 1988, 137:A484.
Borish, L.C. et al. "Interleukin-4 Receptor in Moderate Atopic Asthma A Phase I/II Randonmized, Placebo-controlled Trial" *Am. J. Respir. Crit. Care Med.*, 1999, 160:1816-1823.
Bossé, Y. et al. "Toward a Comprehensive Set of Asthma Susceptibility Genes" *Annual Review of Medicine*, 2007, 58:171-184.
Bradley, C.M. et al. "Limits of Cooperativity in a Structurally Modular Protein: Response of the Notch Ankyrin Domain to Analogous Alanine Substitutions in Each Repeat" J Mol Biol, 2002, 324:373-386.
Brafford, P. et al. "Gene expression profiling of melanoma cells—searching the haystack" Journal of Translational Medicine, 2005, 3:2, pp. 1-2.
Broide, D.H. "Immunologic and inflammatory mechanisms that drive asthma progression to remodeling" J. Allergy Clin. Immunol., 2008, 121(3):560-570.
Bryan, P.M. et al. "The Atrial Natriuretic Peptide Receptor (NPR-A/GC-1) is Dephosphorylated by Distinct Microcystin-sensitive and Magnesium-dependent Protein Phosphatase" J. Biol. Chem., 2002, 277(18):16041-16047.
Buskens, C. et al. "Adenocarcinomas of the Gastro-Esophageal Junction: A Comparative Study of the Gastric Cardia and the Esophagus with Respect to Cyclooxygenase-2 Expression" Digestive Disease Week Abstracts and Itinerary Planner, 2003, Abstract No. 850.
Cane, A. et al. "The Endogenous Oxindoles 5-Hydroxyoxindole and Isatin Are Antiproliferative and Proapoptotic" Biochemical and Biophysical Research Communications, 2000, 276:379-384.
Capizzi, R.L. "Molecular and Cellular Biology of Cancer" In: Internal Medicine, 4th Edition, Ed. Jay Stein, Elsevier Science, 1994, pp, 707-729.
Carr, K.M. et al. "Gene-expression profiling in human cutaneous melanoma" Oncogene, 2003, 22:3076-3080.
Carthew, R.W. "Gene silencing by double-stranded RNA" Current Opinion in Cell Biology, 2001, 13:244-248.
Chanez, P. et al. "Atrial natriuretic factor (ANF) is a potent bronchodilator in asthma" J. Allergy Clin. Immunol., 1990, 86:321-324.

Chen, J. et al. "Therapeutic benefit of intracerebral transplantation of bone marrow stromal cells after cerebral ischemia in rats" J. Neurological Sci., 2001, 189:49-57.
Chen, J. et al. "Therapeutic benefit of intravenous administration of bone marrow stromal cells after cerebral ischemia in rats" Stroke, 2001, 32:1005-1011.
Chen, J.H. "Application of cationic polymer vector for gene delivery systems" Yao Xue Xue Bao, Apr. 2003, 38(4):316-20, abstract.
Chen, S. et al. "1,25 Dihydroxyvitamin D Amplifies Type a Natriuretic Peptide Receptor Expression and Activity in Target Cells" J Am Soc Nephrol, 2005, 16:329-339.
Chen, X. et al. "Human bone marrow stromal cell cultures" J Neurosci Res, 2002, 69:687-691.
Chen, X. et al. "Ischemic rat brain extracts induce human marrow stromal cell growth factor production" Neuropathology, 2002, 22:275-279.
Chengalvala, M.V. et al. "Gene Expression Profiling and its Practice in Drug Development" Current Genomics, 2007, 8(4):262-270.
Chin, L. et al. "Malignant melanoma: modern black plague and genetic black box" Genes & Development, 1998, 12(22):3467-3481.
Chin, L. et al. "Malignant melanoma: genetics and therapeutics in the genomic era" Genes & Development, 2006, 20:2149-2182.
Chiu, Y.L. et al. "RNAi in Human Cells: Basic Structural and Functional Features of Small Interfering RNA" Molecular Cell, Sep. 2002, 10(3):549-561.
Chopp, M. et al. "Spinal cord injury in rat: treatment with bone marrow stromal cell transplantation" Neuroreport, 2000, 11:3001-3005.
Chow, W.H. et al. "Rising Incidence of Renal Cell Cancer in the United States" JAMA, May 1999, pp. 1628-1631, vol. 281, No. 17.
Clark, A.R. "Mechanisms of steroid action and resistance in inflammation: MAP kinase phosphatase 1: a novel mediator of biological effects of glucocorticoids" Journal of Indocrinology, 2003, 178:5-12.
Clark, J.I. et al. "Adjuvant High-Dose Bolus Interleukin-2 for Patients With High-Risk Renal Cell Carcinoma: A Cytokine Working Group Randomized Trial" Journal of Clinical Oncology, Aug. 15, 2003, pp. 3133-3140, vol. 21, No. 16.
Clemens, J.C. et al. "Use of double-stranded RNA interference in Drosophila cell lines to dissect signal transduction pathways" PNAS, 2000, 97:6499-6503.
Clusel, C. et al. "Ex vivo regulation of specific gene expression by nanomolar concentration of double-stranded dumbbell oligonucleotides" Nucleic Acids Research 1993, 21(15):3405-3411.
Cohen, H.T. et al. "Medical Progress: Renal-Cell Carcinoma" The New England Journal of Medicine, Dec. 8, 2005, pp. 2477-2490, vol. 353, No. 23.
Collins, F.S. et al. "Generation and initial analysis of more than 15,000 full-length human and mouse cDNA sequences" Proc Natl Acad Sci, 2002:99:16899-16903.
Cookson, W.O.C. "Asthma Genetics" Chest, 2002, 121:7S-13S.
Costello, J.M. et al. "A review of the natriuretic hormone system's diagnostic and therapeutic potential in critically ill children" Pediatr. Crit. Care Med., 2006, 7(4):308-318.
Curtis, J.L. et al. "The Immunopathogensis of Chronic Obstructive Pulmonary Disease" Proc, Am. Thorac. Soc., 2007, 4:512-521.
Daggubati, S. et al. "Adrenomedullin, endothelin, neuropeptide Y, atrial, brain, and C-natriuretic prohormone peptides compared as early heart failure indicators" Cardiovascular Research, 1997, pp. 246-255, vol. 36.
Damascelli, B., et al. "First Clinical Experience with a High-Capacity Implantable Infusion Pump for Continuous Intravenous Chemotherapy." CardioVascular and Interventional Radiology. 1999, 22: 37-43.
De Palo, E.F. et al. "Circulating Immunoreactive proANP(1-30) and proANP(31-67) in Sedentary Subjects and Athletes" Clinical Chemistry, 2000, pp. 843-847, vol. 46, No. 6.
De Wit, N.J.W. et al. "Analysis of differential gene expression in human melanocytic tumour lesions by custom made oligonucleotide arrays" British Journal of Cancer, 2005, 92:2249-2261.

(56) References Cited

OTHER PUBLICATIONS

Delporte, C. et al. "Discovery of a potent atrial natriuretic peptide antagonist for ANPA receptors in the human neuroblastoma NB-OK-1 cell line" European Journal of Pharmacology, 1992, 224:183-188.
Dermer, G.B. "The Last Word: Another Anniversary for the War on Cancel" Bio/Technology, Mar. 1994, p. 320, vol. 12.
Dietz, J.R. et al. "Evidence supporting a physiological role for proANP-(1-30) in the regulation of renal excretion" Am J Physiol Regul Integr Comp Physiol, 2001, pp. R1510-R1517, vol. 280.
Doczi, T.P. et al. "Atrial natriuretic peptide (ANP) attenuates brain oedema accompanying experimental subarachnoid haemorrhage" Acta Neurochir (Wien), 1995, 132:87-91.
Dorn, G. et al. "siRNA relieves chronic neuropathic pain" Nucleic Acids Research, 2004, 32:e49.
Drewett, J.G. et al. "The family of guanylyl cyclase receptors and their ligands" Endocrine Reviews, 1994, 15(2):135-162.
Eichelbaum, E.J. et al. "Cardiac and kidney hormones cure up to 86% of human small-cell lung cancers in mice" Eur J Clin Invest, 2008, 38(8):562-570.
El-Ayoubi, R. et al. "Urinary responses to acute moxonidine are inhibited by natriuretic peptide receptor agonist" British Journal of Pharmacology, 2005, 145:50-56.
Elbashir, S.M. et al. "Duplexes of 21-nucleotide RNAs mediate RNA interference in cultured mammalian cells" Nature, May 24, 2001, 411:494-498.
Elbashir, S.M. et al. "RNA interference is mediated by 21- and 22-nucleotide RNAs" Genes and Development, 2001, 15:188-200.
Ernst, P. "Review article: the role of inflammation in the pathogenesis of gastric cancer" Aliment Pharmacol Ther., 1999, pp. 13-18, vol. 13, No. 1.
Fattal, E. et al. "Biodegradable polyalkylcyanoacrylate nanoparticles for the delivery of oligonucleotides" Journal of Controlled Release, 1998, 53:137-143.
Filomeni, G. et al. "Pro-apoptotic Activity of Novel Isatin-Schiff Base Copper(II) Complexes Depends on Oxidative Stress Induction and Organelle-selective Damage" Journal of Biological Chemistry, 2007, 282(16)12010-12021.
Fiscus, R.R. "Involvement of Cyclic GMP and Protein Kinase G in the Regulation of Apoptosis and Survival in Neural Cells" NeuroSignals, 2002, 11:175-190.
Fisher, E. et al. "Comparative Histopathologic, Histochemical, Electron Microscopic and Tissue Culture Studies of Bronchial Carcinoids and Oat Cell Carcinomas of Lung" Am J Clin Pathol, 1978, pp. 165-172, vol. 69.
Fluge, T. et al. "Bronchodilation using combined urodilatin—albuterol administration in asthma: a randomized, double-blind, placebo-controlled trial" European Journal of Medical Research, 1999, 4(10):411-415.
Fonarow, G.C. et al. "Combining natriuretic peptides and necrosis markers in determining prognosis in heart failure" Rev. Cardiovasc. Med., 2003, 4(suppl 4):S20-S28.
Forssmann, W.G. et al. "The renal urodilatin system: clinical implications" Cardiovascular Research, 2001, 51:450-462.
Franz, M. et al. "N-terminal fragments of the proatrial natriuretic peptide in patients before and after hemodialysis treatment" Kidney International, 2000, pp. 374-383, vol. 58.
Franz, M. et al. "Plasma concentration and urinary excretion of N-terminal proatrial natriuretic peptides in patients with kidney diseases" Kidney International, 2001, pp. 1928-1934, vol. 59.
Freshney, R.I. "Culture of Animal Cells: A Manual of Basic Technique" Alan R. Liss, Inc.: New York, 1983, pp. 3-4.
Friedman, H.S. et al. "Glioblastoma Multiforme and the Epidermal Growth Factor Receptor" N Engl J Med, Nov. 2005, pp. 1997-1999, vol. 353, No. 19.
Fujiseki, Y. et al. "Natriuretic Peptide Receptors, NPR-A and NPR-B, in Cultured Rabbit Retinal Pigment Epithelium Cells" Japanese Journal of Pharmacology, 1999, 79:359-368.

Furst, R. et al. "Atrial natriuretic peptide induces mitogen-activated protein kinase phosphatase-1 in human endothelial cells via Rac1 and NAD(P)H oxidase/Nox2-activation" Circ. Res., 2005, 96:43-53.
Gabellini, C. et al. "Involvement of RB gene family in tumor angiogenesis" Oncogene, 2006, 25:5326-5332.
Gaiger, A. et al. "Immunity to WT1 in the animal model and in patients with acute myeloid leukemia" Blood, 2000, 96:1480-1489.
Garrett, M.D. et al. "Discovering Novel Chemotherapeutic Drugs for the Third Millennium" European Journal of Cancer, 1999, pp. 2010-2030, vol. 35, No. 14.
Glover, V. et al. "Isatin: Identity with the Purified Endogenous Monamine Oxidase Inhibitor Tribulin" Journal of Neurochemistry, 1988, 51(2):656-659.
Gogas, H. et al. "Biomarkers in melanoma" Annals of Oncology, Aug. 2009, 20(Supplement 6):vi8-vi13.
Gopalakrishnan, M. et al. "Stable expression and pharmacological properties of the human α7 nicotinic acetylcholine receptor" European Journal of Pharmacology: Molecular Pharmacology Section, 1995, 290(3):237-246.
Gower, W.R. et al. "Four Peptides Decrease Human Colon Adenocarcinoma Cell Number and DNA Synthesis via Cyclic GMP" International Journal of Gastrointestinal Cancer, 2005, pp. 77-88, vol. 36, No. 2.
Gower, W.R. et al. "Regulation of atrial natriuretic peptide secretion by cholinergic and PACAP neurons of the gastric antrum" Am. J. Physiol. Gastrointest, Liver Physiol., 2003, 284:G68-G74.
Gratzner, H.G., "Monoclonal Antibody to 5-Bromo- and 5-Iododeoxyuridine: A New Reagent for Detection of DNA Replication" Science, Oct. 29, 1982, pp. 474-475, vol. 218.
Greenberg, B.D. et al. "Nucleotide sequence of the gene encoding human atrial natriuretic factor precursor" Nature, 1984, 312(5995):656-658.
Greenfeder, S. et al. "Th2 cytokines and asthma The role of interleukin-5 in allergic eosinophilic disease" Respitory Research, 2001, 2:71-79.
Greten, F.R. et al. "IKKβ links inflammation and tumorigenesis in a mouse model of colitis-associated cancer" Cell, 2004, 118:285-296.
Gunning, M.E. et al. "Atrial Natriuretic Peptide(31-67) Inhibits Na+ Transport in Rabbit Inner Medullary Collecting Duct Cells: Role of Prostaglandin E2" Journal of Clinical Investigation, May 1992, pp. 1411-1417, vol. 89.
Gura, T. "Cancer Models: Systems for Identifying New Drugs are Often Faulty" Science, 1997, 278(5340):1041-1042, pp. 1-5.
Haagerup, A. et al. "Asthma and atopy—a total genome scan for susceptibility genes" Allergy, 2002, 57:680-686.
Haberman, A.B. "Strategies to Move Beyond Target Validation" Genetic Engineering News, Dec. 2005, 25(21):36.
Halder, J. et al. "Focal Adhesion Kinase Targeting Using in vivo Short Interfering RNA Delivery in Neutral Liposomes for Ovarian Carcinoma Therapy" Clinical Cancer Research, 2006, 12:4916-4924.
Hamad, A. et al. "Guanylyl cyclases, nitric oxide, natriuretic peptides, and airway smooth muscle function" Am. J. Physiol. Lung Cell. Mol. Physiol., 2003, 285:L973-L983.
Hamet, P. et al. "Aspects physiologiques et physiopathologiques du facteur natriuretique auriculaire" Nephrologie, 1987, 8:7-12, abstract.
Hammond, S.M. et al. "Argonaute2, a Link Between Genetic and Biochemical Analyses of RNAi" Science, Aug. 10, 2001, 293:1146-1150.
Harborth, J. et al. "Identification of essential genes in cultured mammalian cells using small interfering RNAs" Journal of Cell Science, 2001, 114:4457-4565.
Haseloff, J. et al. "Simple RNA enzymes with new and highly specific endoribonuclease activities" Nature, 1988, 334(6183):585-591.
He, Q. et al. "Inducible regulation of human brain natriuretic peptide promoter in transgenic mice" Am. J. Physiol. Heart Circ, Physiol., 2001, 280:H368-H376.

(56) References Cited

OTHER PUBLICATIONS

Heim, J.M. et al. "Urodilatin and β-ANF: Binding Properties and Activation of Particulate Guanylate Cyclase" Biochemical and Biophysical Research Communications, Aug. 30, 1989, pp. 37-41, vol. 163, No. 1.
Helene, C. et al. "Control of Gene Expression by Triple Helix-Forming Oligonucleotides: The Antigene Strategy" Annals of the New York Academy of Sciences, 1992, 660(1):27-36.
Hirata, Y. "Heterologus Down-Regulation of Vascular Atrial Natriuretic Peptide Receptors by Phorbol Esters" Biochemical and Biophysical Research Communications, May 16, 1988, 152(3)1097-1103.
Ho, R.J.Y. et al. "Interactions of Target-sensitive Immunoliposomes with Herpes Simplex Virus" The Journal of Biological Chemistry,1987, 262(29):13979-13984.
Ho, R.J.Y. et al. "Target-sensitive immunoliposomes as an efficient drug carrier for antiviral activity" The Journal of Biological Chemistry, 1987, 262(29):13973-13978.
Ho, R.J.Y. et ar"Target-sensitive immunoliposomes: preparation and characterization" Biochemistry, 1986, 25:5500-5506.
Holloway, J.W . et al. "Identifying novel genes contributing to asthma pathogenesis" *Current Opinion in Allergy and Clinical Immunology*, 2007, 7:69-74.
Hong, K.U. et al. "Clara Cell Secretory Protein-Expressing Cells of the Airway Neuroepithelial Body Microenvironment Include a Label-Retaining Subset and Are Critical for Epithelial Renewal after Progenitor Cell Depletion" *Am. J. Respir. Cell Mol. Biol.*, 2001, 24:671-681.
Howard, K.A. et al."RNA Interference in Vivo and in Vitro Using a Chitosan/siRNA Nanoparticle System" Molecular Therapy, 2006, 14(4):476-484.
Hulks, G. et al. "Bronchodilator effect of atrial natriuretic peptide in asthma" Br Med J, Oct. 28, 1989, 299:1081-1082.
Hulks, G. et al. "Influence of elevated plasma levels of atrial natriuretic factor on bronchial reactivity in asthma" Am. Rev. Respir. Dis., 1991, 143:778-782, abstract.
Hulks, G. et al. "Effect of atrial natriuretic factor on bronchomotor tone in the normal human airway" Clin Sci, 1990, 79:51-55.
Hulks, G. et al. "Inhaled atrial natriuretic peptide and asthmatic airways" Br. Med J, 1992, 304:1156.
Hulks, G. et al. High dose inhaled atrial natriuretic peptide is a bronchodilator in asthmatic subjects Eur Respir J., 1994, 7:1593-1597.
Hunter, E.F.M. et al. "Analysis of peptides derived from Pro Atrial Natriuretic Peptide that circulate in man and increase in heart disease" Scandinavian Journal of Clinical and Laboratory Investigation, 1998, pp. 205-216, vol. 58.
Hutvagner, G. et al. "RNAi: nature abhors a double-strand" Current Opinion in Genetics & Development, 2002, 12:225-232.
Igosheva, N. et al. "Isatin, an endogenous monamine oxidase inhibitor, triggers a dose- and time-dependent switch from apoptosis to necrosis in human neuroblastoma cells" Neurochemistry International, 2005, 47(3):216-224.
Inoue, J.I. et al. "NF-$_K$B activation in development and progression of cancer" Cancer Science, 2007, 98:268-274.
Ishii, Y. et al. "Effects of atrial natriuretic peptide on Type II alveolar epithelial cells of the rat lung. Autoradiographic and morphometric studies" J Anat., 1989, 166:85-95.
Ivanova, K. et al. "Differential Expression of Functional Guanylyl Cyclases in Melanocytes: Absence of Nitric-Oxide-Sensitive lsoform in Metastatic Cells" Journal of Investigative Dermatology, Mar. 2001, 116(3):409-416.
Izumi, T. et al. "Blockade of the natriuretic peptide receptor guanylyl cyclase-A inhibits NF-$_K$B activation and alleviates myocardial ischemia/reperfusion injury" J Clin Invest, 2001, 108:203-213.
Jacque, J.M. et al. "Modulation of HIV-1 replication by RNA interference" Nature, Jul. 25, 2002, 418(6896):435-438.
Jain, R.K. "Barriers to Drug Delivery in Solid Tumors" Scientific American, Jul. 1994, 58-65.

Jemal, A. et al. "Cancer Statistics. 2005" CA: A Cancer Journal for Clinicians, 2005, pp. 10-30, vol. 55.
Jensen, K.T. et al. "A new, fast and reliable radioimmunoassay of brain natriuretic peptide in human plasma. Reference values in healthy subjects and in patients with different diseases" Scand J Clin Lab Invest, 1997, 57:529-540.
Jin, H, et al. "Novel analog of atrial natriuretic peptide selective for receptor-A produces increased diuresis and natriuresis in rats" J. Clin. Invest., 1996, 98:969-976.
Kaiser, J. et al. "CANCER: First Pass at Cancer Genome Reveals Complex Landscape" Science, Sep. 8, 2006, p. 1370, vol. 313.
Kaneko, T. et al. "C-type natriuretic peptide (CNP) is the major natriuretic peptide in human cerebrospinal fluid" Brain Res, 1993, 612:104-109.
Kanwal, S. et al. "Intracellular fragments of the natriuretic peptide receptor-C (NPR-C) attenuate dopamine efflux" Endocrinology, 1999, 140(3)1118-1124.
Karin, M. "Mitogen activated protein kinases as targets for development of novel anti-inflammatory drugs" Annals of the Rheumatic Diseases, 2004, 63(Suppl. 2):ii62-ii64.
Katas, H. et al. "Development and characterisation of chitosan nanoparticles for siRNA delivery" Journal of Controlled Release, 2006, 115(2):216-225.
Kato, N. et al. "Genetic analysis of the atrial natriuretic peptide gene in essential hypertension" *Clinical Science*, 2000, 98:251-258.
Kelly, R. et al. "Are natriuretic peptides clinically useful as markers of heart failure?" Ann. Clin. Biochem., 2001, 38:94-102.
Khurana, M.L. et al. "Receptor-mediated stimulatory effect of atrial natriuretic factor, brain natriuretic peptide, and C-type natriuretic peptide on testosterone production in purified mouse Leydig cells: activation of cholesterol side-chain cleavage enzyme" Endocrinology, 1993, 133:2141-2149.
Kiemer, A. and Vollmar, A. "Autocrine regulation of inducible nitric-oxide synthase in macrophages by atrial natriuretic peptide" J Biol Chem, 1998, 273:13444-13451.
Kiemer, A. et al. "cGMP-mediated inhibition of TNF-α production by the atrial natriuretic peptide in murine macrophages" J Immunol, 2000, 165:175-181.
Kim, J.W. et al. "Effect of phosphorylation and S—S bond-induced dimerization on DNA binding and transcriptional activation by C/EBPβ" Proc Natl Acad Sci USA, 2007, 104:1913-1918.
Kisielow, M. et al."Isoform-specific knockdown and expression of adaptor protein ShcA using small interfering RNA" Biochem J., 2002, 363(1):1-5.
Klibanov, A.L. et al. "Amphipathic polyethyleneglycols effectively prolong the circulation time of liposomes" FEBS Letters, 1990, 268:235-237.
Knaapen, A.M. et al. "Inhaled particles and lung cancer. Part A: Mechanisms" International Journal of Cancer, 2004, 109:799-809.
Kojima, M. et al. "Cloning and sequence analysis of cDNA encoding a precursor for rat brain natriuretic peptide" Biochem. Biophys. Res. Commun., 1989, 159(3):1420-1426.
Kong, X. et al. "Mice Deficient in Atrial Natriuretic Peptide Receptor A (NPRA) Exhibit Decreased Lung Inflammation: Implication of NPRA Signaling in Asthma Pathogenesis" Journal of Allergy and Clinical Immunology, Jan. 2007, 119(1):5127, abstract 501.
Krontiris, T.G. "Molecular and Cellular Biology of Cancer" In: Internal Medicine, 4th Edition, Ed. Jay Stein, Elsevier Science, 1994, pp. 699-707.
Kumar, M. et al. "Intranasal IFN-γ gene transfer protects BALB/c mice against respiratory syncytial virus infection" Vaccine, 2000: 18:558-567.
Kumar, R. et al. "Expression of Guanylyl Cyclase-A/Atrial Natriuretic Peptide Receptor Blocks the Activation of Protein Kinase C in Vascular Smooth Muscle Cells: Role of cGMP and cGMP-Dependent Protein Kinase" Hypertension, 1997, 29:414-421.
Kumar, R. et al. "Stimulation of atrial natriuretic peptide receptor/ guanylyl cyclase—A signaling pathway antagonizes the activation of protein kinase C-α in murine Leydig cells" Biochimica et Biophysica Acta, 1997, pp. 221-228, vol. 1356.

(56) References Cited

OTHER PUBLICATIONS

Kurihara, M. et al. "Lower No. Of atrial natriuretic peptide receptors in thymocytes and spleen cells of spontaneously hypertensive rats" Biochemical and Biophysical Research Communications, 1987,149:1132-1140.
La Vecchia, C. et al. "Smoking and Renal Cell Carcinoma" Cancer Research, Sep. 1, 1990, pp. 5231-5233, vol. 50.
Lambert, G. et al. Nanoparticulate systems for the delivery of antisense oligonucleotides Advanced Drug Delivery Reviews, Mar. 2001, 47:99-112.
Landen, C.N. et al. "Intraperitoneal Delivery of Liposomel siRNA for Therapy of Advanced Ovarian Cancer" Cancer Biology & Therapy, 2006, 5(12):1708-1713.
Leckie, M.J. etal. "Effects of an interleukin-5 blocking monoclonal antibody on eosinophils, airway hyper-responsiveness, and the late asthmatic response" Lancet, Dec. 2000, 356:2144-2148.
Lee, N.S. et al. "Expression of small interfering RNAs targeted against HIV-1 rev transcripts in human cells" Nature Biotechnology, May 2002, 20:500-505.
Lelievre V. et al. "Proliferative Actions of Natriuretic Peptides on Neuroblastoma Cells" The Journal of Biological Chemistry, Nov. 23, 2001, pp. 43668-43676, vol. 276, No. 47.
Lenz, A. et al. "Cardiac Hormones Eliminate some Human Squamous Lung Carcinomas in Athymic Mice" European Journal of Clinical Investigation, 2010 in press, p. 1-13.
Levin, E.R. et al. "Mechanisms of Disease: Natriuretic Peptides" New England Journal of Medicine, 1998, 339:321-328.
Levy, J.A. et al. "Inactivation of Murine RNA Tumor Viruses by Isatin Beta-Thiosemicarbazone" Virology, Oct. 15, 1976, 74(2):426-431.
Li, Y. et al. "Human marrow stromal cell therapy for stroke in rat: Neurotrophins and functional recovery" Neurology, 2002, 59:514-523.
Li, Y. et al. "Intrastriatal transplantation of bone marrow nonhematopoietic cells improves functional recovery after stroke in adult mice" Journal of Cerebral Blood Flow & Metabolism, 2000, 20:1311-1319.
Liang, F. et al. "Sp1 dependence of natriuretic peptide receptor A gene transcription in rat aortic smooth muscle cells" Endocrinology, 1999, 140(4)1695-1701.
Lieberman, J. et al. "Interfering with disease: opportunities and roadblocks to harnessing RNA interference" Trends in Molecular Medicine, Sep. 2003, 9(9):397-403.
Lima, J.J. et al. "A polymorphism in the *NPP4* gene associated with asthma" *Clinical and Experimental Allergy*, 2008, 38:117-1123.
Lin, K-F. et al. "Atrial natriuretic peptide gene delivery attenuates hypertension, cardiac hypertrophy, and renal injury in salt-sensitive rats" Human Gene Therapy, 1998, 9:1429-1438.
Lin, K-F. et al. "Human atrial natriuretic peptide gene delivery reduces blood pressure in hypertensive rats" Hypertension, 1995, 26:847-853.
Linder, M.W. et al. "Pharmacogenetics: a laboratory tool for optimizing therapeutic efficiency" Clinical Chemistry, 1997, pp. 254-266, vol. 43, No. 2.
Liu, X. et al. "The influence of polymeric properties on chitosan/siRNA nanoparticle formulation and gene silencing" Biomaterials, 2007, 28:1280-1288.
Liu, Y. et al. "Discovery of Inhibitors that Elucidate the Role of UCH-L1 Activity in the H1299 Lung Cancer Cell Line" Chemistry & Biology, 2003, 10(9):837-846.
Lobbezoo, M.W. et al. "Signal Transduction Modulators for Cancer Therapy: From Promise to Practice?" The Oncologist, 2003, 8:210-213.
Louzier, V. et al. "Adenovirus-mediated atrial natriuretic protein expression in the lung protects rats from hypoxia-induced pulmonary hypertension" Hum Gene Ther, 2001, 12:503-513.
Lu, D. et al. "Adult bone marrow stromal cells administered intravenously to rats after traumatic brain injury migrate into brain and improve neurological outcome" NeuroReport, 2001, 12:559-563.

Mahmood, A. et al. "Intracerebral transplantation of marrow stromal cells cultured with neurotrophic factors promotes functional recovery in adult rats subjected to traumatic brain injury" J Neurotrauma, 2002, 19:1609-1617.
Mahmood, A. et al. "Intracranial bone marrow transplantation after traumatic brain injury improving functional outcome in adult rats" Journal of Neurosurgery, 2001, 94:589-595.
Mahmood, A. et al. "Treatment of traumatic brain injury in female rats with intravenous administration of bone marrow stromal cells" Neurosurgery, 2001, 49:1196-1204.
Mailand, N. et al. "Deregulated human Cdc14a phosphatase disrupts centrosome separation and chromosome segregation" Nature Cell Biology, 2002, 4(4):317-322.
Maisel, A.S. etal. "Cardiac natriuretic peptides: A proteomic window to cardiac function and clinical management" Rev. Cardiovasc. Med., 2003, 4(suppl 4):53-812.
Malebra, G. et al. "A review of asthma genetics: gene expression studies and recent candidates" *Journal of Applied Genetics*, 2005, 46(1):93-104.
Martey, C.A. et al. "Cigarette smoke induces cyclooxygenase-2 and microsomal prostaglandin E2 synthase in human lung fibroblasts: implications for lung inflammation and cancer" Am J Physiol Lung Cell Mol Physiol, 2004, 287:L981-991.
Martin, D.R. et al. "Three peptides from the ANF prohormone NH2 are natriuretic and/or kaliuretic" Am J Physio Renal Physiol, Dec. 1990, pp. F1401-1408, vol. 258, abstract.
Martin, J. et al. "Modulation by biologic response modifiers of hepatitis C virus antigen-independent cytokine secretion in blood mononuclear cells" Cytokine, 1999, 11:267-273.
Martinez, S.R. et al. "Molecular Markers in Malignant Cutaneous Melanoma: Gift Horse or One-Trick Pony?" Journal of Cellular Biochemistry, 2005, 96:473-483.
Massion, P.P. et al. "The molecular basis of lung cancer: molecular abnormalities and therapeutic implications" Respiratory Research, 2003, 4(1):12.1-12.15.
Matanić, D. et al. "Cytokines in patients with lung cancer" Scand J Immunol, 2003, 57;173-178.
Matsukawa, N. et al. "The natriuretic peptide clearance receptor locally modulates the physiological effects of the natriuretic peptide system" Proc. Natl. Acad. Sci. USA, 1999, 96:7403-7408.
Matsuse, H. et al, "Recurrent Respiratory Syncytial Virus Infections in Allergen-Sensitized Mice Lead to Persistent Airway Inflammation and Hyperresponsiveness" The Journal of Immunology, 2000, 164:6583-6592.
Matzke, M. et al. "RNA: Guiding Gene Silencing" Science, 2001, 293:1080-1083.
McCaffrey, A.P. et al. "Gene expression: RNA interference in adult mice" Nature, Jul. 2002, 418(6893):38-39.
McLaughlin, J.K. et al. "A Population-Based Case-Control Study of Renal Cell Carcinoma", J Natl Cancer Inst, Feb. 1984, pp. 275-284, vol. 72.
Mellinghoff, I.K. et al. "Molecular Determinants of the Response of Glioblastomas to EGFR Kinase Inhibitors" The New England Journal of Medicine, Nov. 2005, pp. 2012-2024, vol. 353, No. 19.
Meyer, E.H. et al. "Glycolipid activation of invariant T cell receptor$^+$ NK T cells is sufficient to induce airway hyperreactivity independent of conventional CD4$^+$ T cells" *Proc. Natl. Acad. Sci.*, Feb. 21, 2006, 103(8):2782-2787.
Misono, K.S. "Natriuretic peptide receptor: Structure and signaling" Molecular and Cellular Biochemistry, 2002, 230:49-60.
Mizuguchi, M. et al. "Bronchoprotective effects of atrial natriuretic peptide against propanolol-induced bronchoconstriction after allergic reaction in guinea pigs" Clinical and Experimental Allergy, 2000, 30:439-444.
Mohapatra, S. etal. "Intranasal atrial natriuretic peptide (ANP) gene transfer attenuates airway reactivity in a mouse model of allergic asthma" *Journal of Clinical Immunology*, Feb. 1, 2003, 111(2):S309, abstract.
Morita, R. et al. "Atrial Natriuretic Peptide Polarizes Human Dendritic Cells Toward a Th2-Promoting Phenotype Through Its Receptor Guanylyl Cyclase-Coupled Receptor A1" The Journal of Immunology, 2003, 170:5869-5875.

(56) References Cited

OTHER PUBLICATIONS

Morstyn, G. et al. "Immunohistochemical Identification of Proliferating Cells in Organ Culture Using Bromodeoxyuridine and a Monoclonal Antibody" The Journal of Histochemistry and Cytochemistry, 1986, pp. 697-701, vol. 34, No. 6.

Motohashi, S. et al. "Preserved IFN-α production of circulating Vα24 NKT cells in primary lung cancer patients" Int J Cancer, 2002, 102:159-165.

Mueller, C. et al. "B-type natriuretic peptide (BNP): can it improve our management of patients with congestive heart failure?" Swiss Med Wkly, 2002, 132:618-622.

Nafee, N. et al. "Chitosan-coated PLGA nanoparticles for DNA/RNA delivery: effect of the formulation parameters on complexation and transfection of antisense oligonucleotides" Nanomedicine: Nanotechnology, Biology, and Medicine, 2007, 3(3):173-183.

Nakagawa, K. et al. "Plasma concentrations of atrial and brain natriuretic peptides in a case with hypertensive encephalopathy" Neurol. Res., 2002, 24:627-630.

Nakao, N. et al. "Effect of atrial natriuretic peptide on ischemic brain edema: Changes in brain water and electrolytes" Neurosurgery, 1990, 27:39-44.

Nannipieri, M. et al. "Association between polymorphisms of the Atrial Natriuretic peptide gene and proteinuria: a population-based study" Diabetologia, 2003, 46:429-432.

Nannipieri, M. et al. "Polymorphisms in the nANP (Human Atrial Natriuretic Peptide) Gene, Albuminuria, and Hypertension" *Hypertension*, Jun. 2001, 37:1416-1422.

Naruse, S. et al. "Effects of atrial natriuretic peptide on brain oedema: The change of water, sodium, and potassium contents in the brain" Acta Neurochir Suppl (Wien), 1990, 51:118-121.

Nazario, B. et al. "Atrial and brain natriuretic peptides stimulate the production and secretion of C-type natriuretic peptide from bovine aortic endothelial cells" J. Clin. Invest., 1995, 95:1151-1157.

Needleman, P. et al. "Atriopeptin: a cardiac hormone intimately involved in fluid, electrolyte, and blood-pressure homeostasis" N Engl J Med, 1986, 314:828-834.

Neidle, S. editor, "Failure Modes in the Discovery Process" Cancer Drug Design and Discovery, 2008, Elsevier/Academic Press, pp. 427-431.

Ngo, J.T. et al. "Computational Complexity, Protein Structure Prediction, and the Levinthal Paradox" The Protein Folding Problem and Tertiary Structure Prediction, 1994, Birkhauser Boston, Le Grand Edition, pp. 491-495.

Nguyen, T.D. et al. "Citrus Flavonoids Stimulate Secretion by Human Colonic T84 Cells" The Journal of Nutrition, 1993, pp. 259-268, vol. 123.

Nocera, R. et al. "Novel strategies of neuroprotection against pathologic consequences of stroke in the aged brain" Society for Neurosci. Abstracts, 2001, 27(2):2302, Meeting date Nov. 10-15, 2001.

Novina, C.D. et al. "The RNAi revolution" Nature, 2004, 430:161-164.

Nuglozeh, E. et al. "Gene expression of natriuretic peptide receptors in rats with DOCA-salt hypertension" Am J Physiol Cell Physiol, 1997, 273:1427-1434.

Nykanen, A. et al. "ATP Requirements and small Interfering RNA Structure" Cell, Nov. 2001, 107:300-321.

Nyormoi, O. et al. "Transcriptional regulation of metastasis-related genes in human melanoma" Clinical and Experimental Metastasis, 2003, 20:251-263.

Office Action dated Apr. 1, 2010 in U.S. Appl. No. 11/799,225, filed Apr. 30, 2007.

Office Action dated Apr. 25, 2008 in U.S. Appl. No. 11/059,814, filed Feb. 17, 2005.

Office Action dated Apr. 30, 2012 in U.S. Appl. No. 11/998,792, filed Nov. 30, 2007.

Office Action dated Aug. 20, 2010 in U.S. Appl. No. 11/799,225, filed Apr. 30, 2007.

Office Action dated Aug. 9, 2007 in U.S. Appl. No. 11/059,814, filed Feb. 17, 2005.

Office Action dated Dec. 11, 2009 in U.S. Appl. No. 11/998,792, filed Nov. 30, 2007.

Office Action dated Feb. 1, 2011 in U.S. Appl. No. 12/259,110, filed Feb. 1, 2011.

Office Action dated Jun. 1, 2009 in U.S. Appl. No. 11/998,792, filed Nov. 30, 2007.

Office Action dated May 18, 2010 in U.S. Appl. No. 11/998,792, filed Nov. 30, 2007.

Office Action dated Nov. 17, 2011 in U.S. Appl. No. 11/998,792, filed Nov. 30, 2007.

Office Action dated Oct. 13, 2010 in U.S. Appl. No. 11/998,792, filed Nov. 30, 2007.

Office Action dated Sep. 2, 2009 in U.S. Appl. No. 11/799,225, filed Apr. 30, 2007.

Ogata, A. et al. "Isatin, an endogenous MAO inhibitor, improves bradykinesia and dopamine levels in a rat model of Parkinson's disease induced by Japanese encephalitis virus" Journal of the Neurological Sciences, 2003, 206(1):79-83.

Ogawa, Y. et al. "Molecular cloning of the complementary DNA and gene that encode mouse brain natriuretic peptide and generation of transgenic mice that overexpress the brain natriuretic peptide gene" J. Clin. Invest., 1994, 93(5):1911-1921.

Ohbayashi, H. et al. "Compared effects of natriuretic peptides on ovalbumin-induced asthmatic model" Eur. J. Pharmac., 1998, 346:55-64.

Ohsaki, Y. et al. "Human small cell lung cancer cell lines express functional atrial natriuretic peptide receptors" Cancer Res, 1993, 53:3165-3171.

Ohsaki, Y. et al. "Human small cell lung cancer cells produce brain natriuretic peptide" Oncology, 1999, 56:155-159.

Ohyama, Y. et al. "Stable expression of natriuretic peptide receptors: Effects of HS-142-1, a non-peptide ANP antagonist" Biochemical and Biophysical Research Communications, 1992, 189:336-342.

Oka, D. et al. "Sesquiterpene lactone parthenolide suppresses tumor growth in a xenograft model of renal cell carcinoma by inhibiting the activation of NF-$_\kappa$B" International Journal of Cancer, 2007, 120:2576-2581.

Oliveira, A.M. et al. "Tumor Suppressor Genes in Breast Cancer: The Gatekeepers and the Caretakers" American Society for Clinical Pathology, 2005, 124:S16-S28.

Paddison, P.J, et al. "Short hairpin RNAs (shRNAs) induce sequence-specific silencing in mammalian cells" Genes & Development, 2002, 15:948-958.

Palaparti, A. et al. "Inhibition of atrial natriuretic peptide (ANP) C receptor expression by antisense oligodeoxynucleotides in A10 vascular smoth-muscle cells is associated with attenuation of ANP-C-receptor-mediated inhibition of adenylyl cyclase" Biochem J, 2000, 346:313-320.

Palmer, L.J. et al. "Using single nucleotide polymorphisms as a means to understanding the pathophsiology of asthma" *Respitory Research*, 2001, 2:102-112.

Pan, E. et al, "Central Nervous System: Primary Neoplasms of the Central Nervous System" In: Kufe, D.W., Pollock, R.F., Weichselbaum, R.R., Bast, R.C., Jr., Gensler, I.S., Holland, J.F., and Frei, E., III (Eds.), Cancer Medicine, 6th Edition, 2003, pp. 1193-1226, London: BC Decker.

Pandey, K.N. "Dynamics of internalization and sequestration of guanylyl cyclase/atrial natriuretic peptide receptor-A" Canadian Journal of Physiology and Pharmacology, 2001, 79(8):631-639.

Pandey, K.N. "Intracellular trafficking and metabolic turnover of ligand-bound guanylyl cyclase/atrial natriuretic peptide receptor-A into subcellular compartments" Molecular and Cellular Biochemistry, 2002, 230(1-2):61-72.

Pandey, K.N. et al. "Internalization and trafficking of guanylyl (guanylate) cyclase/natriuretic peptide receptor a is regulated by an acidic tyrosine-based cytoplasmic motif GDAY" Biochemical Journal, 2005, 388:103-113.

Pandey, K.N. et al. "Ligand-regulated Internalization, Trafficking, and Down-regulation of Guanylyl Cyclase/Atrial Natriuretic Peptide Receptor-A in Human Embryonic Kidney 293 Cells" The Journal of Biological Chemistry, 2002, 277:4618-4627.

(56) References Cited

OTHER PUBLICATIONS

Pandey, K.N. et al. "Molecular Cloning and Expression of Murine Guanylate Cyclase/Atrial Natriuretic Factor Receptor cDNA" The Journal of Biological Chemistry, Jul. 25, 1990, 265(21):12342-12348.

Pandey, K.N. et al. "Natriuretic Peptide Receptor-A Negatively Regulates Mitogen-Activated Protein Kinase and Proliferation of Mesangial Cells: Role of cGMP-Dependent Protein Kinase" Biochemical and Biophysical Research Communications, 2000, 271:374-379.

Pandey, K.N. et al. "Functional domains and expression of truncated atrial natriuretic peptide receptor-A: The carboxyl-terminal regions direct the receptor internalization and sequestration in COS-7 cells" Molecular Pharmacology, 2000, 57:259-267.

Pandey, K.N. "Internalization and trafficking of guanylyl cyclase/natriuretic peptide receptor-A" Peptides, 2005, 26:985-1000.

Park, H.S. et al. "The role of novel genes in modifying airway responses in asthma" Current Allergy and Asthma Reports, 2006, 6(2):112-116, abstract.

Paul, C.P. et al. "Effective expression of small interfering RNA in human cells" Nature Biotechnology, May 2002, 20:505-508.

Pedram, A. et al. "Natriuretic Peptides Inhibit G Protein Activation. Mediation Through Cross-Talk Between Cyclic GMP-Dependent Protein Kinase and Regulators of G Protein-Signaling Proteins" J. Biol. Chem., 2000, 275:7365-7372.

Pikarsky, E. et al. "NF-$_K$B functions as a tumour promoter in inflammation-associated cancer" Nature, 2004, 431: 461-466.

Pitari, G.M. et al. "Guanylyl cyclase C agonists regulate progression through the cell cycle of human colon carcinoma cells" PNAS, Jul. 3, 2001, pp. 7846-7851, vol. 98, No. 14.

Plasterk, R.H.A., "RNA Silencing: The Genome's Immune System" Science, 2002, 296:1263-1265.

Popp, F.D. "Synthesis of potential antineoplastic agents. XX, Compounds related to the 3-o-nitrophenylhydrazone of isatin" Journal of Medicinal Chemistry, 1969, 12(1):182-184.

Porter, J.G. et al. "Cloning of a cDNA encoding porcine brain natriuretic peptide" J. Biol. Chem., 1989, 264(12):6689-6692.

Prins, B.A. et al. "Atrial natriuretic peptide inhibits mitogen-activated protein kinase through the clearance receptor" J. Biol. Chem., 1996, 271(24):14156-14162.

Racila, E., et al. "Detection and characterization of carcinoma cells in the blood." Proceedings of the National Academy of Sciences, 1998, 95:4589-4594.

Rahmanto, Y.S. et al, "Identification of distinct changes in gene expression after modulation of melanoma tumor antigen p97 (melanotransferrin) in multiple models in vitro and in vivo" Carcinogenesis, 2007, 28(10):2172-2183.

Rankin, S.M. "Impact of bone marrow on respiratory disease" Curr. Opin. Pharmacol., 2008, 8:236-241.

Rashed, H.M. et al. "Atrial Natriuretic Peptide Inhibits Growth of Hepatoblastoma (HEP G2) Cells by Means of Activation of Clearance Receptors" Hepatology, Apr. 1993, pp. 677-684, vol. 17, No. 4.

Reich, S.J. et al. "Small interfering RNA (siRNA) targeting VEGF effectively inhibits ocular neovascularization in a mouse model" Molecular Vision, 2003, 9:210-216.

Ropper, A.H. and Brown, R.H. (eds) "Intracranial Neoplasms and Paraneoplastic Disorders" In: Adams and Victor's Principles of Neurology, 8th Edition, 2005, New York: McGraw-Hill, pp. 546-591.

Rosenzweig, A. et al. "Atrial Natriuretic Factor and Related Peptide Hormones" Annual Review of Biochemistry, 1991, pp. 229-255, vol. 60.

Rouleau, N. et al. "Development of a Non-radioactive Homogenous HTS Platform to Measure the Activity of Guanylate Cyclase", Poster #P10144, Presented at 10th Annual SBS Conference and Exhibition, Orlando, FL, Sep. 11-15, 2004, Perkinelmer Biosignal Inc., Canada.

Roussel, R. et al. "Investigation of the Human ANP Gene in Type I Diabetic Nephropathy: CaseControl and Follow-up Studies" Diabetes, 2004, 53:1394-1398.

Roy, K. et al. "Oral gene delivery with chitosan? DNA nanoparticles generates immunologic protection in a murine model of peanut allergy" Nature Medicine, 1999, 5(4):387-391.

Roy, R.N. et al. "Organization of the gene for iso-rANP, a rat B-type natriuretic peptide" Biochem. Biophys. Res. Commun., 1990, 171(1):416-423.

Rubattu, S. et al., "Atrial Natriuretic Peptide and Type a Natriuretic Peptide Receptor Gene Polymorphisms with Left Ventricular Mass in Human Essential Hypertension" Journal of the American College of Cardiology, 2006, 48:499-505.

Rubattu, S. et al. "Atrial Natriuretic Peptide Gene Polymorphisms and Risk of Ischemic Stroke in Humans" Stroke, 2004, 35:814-818.

Rudinger, J. "Characteristics of the amino acids as components of a peptide hormone sequence" Peptide Hormones, Biological Council: The Co-ordinating Committee for Symposia on Drug Action; J.A. Parsons, editor; Baltimore: University Park Press, Jun. 1976, pp. 1-7.

Rutherford, R.A.D. et al. "Identification of renal natriuretic peptide receptor subpopulations by use of the non-peptide antagonist, HS-142-1" British Journal of Pharmacology, 1994, 113(3):931-939.

Saba, S.R. et al. "Immunocytochemical Localization of Atrial Natriuretic Peptide, Vessel Dilator, Long-acting Natriuretic Peptide, and Kaliuretic Peptide in Human Pancreatic Adenocarcinomas" Journal of Histochemistry & Cytochemistry, 2005, pp. 989-995, vol. 53, No. 8.

Saccani, A. et al. "p50 Nuclear Factor-$_K$B Overexpression in Tumor-Associated Macrophages Inhibits M1 Inflammatory Responses and Antitumor Resistance" Cancer Research, Dec. 2006, 66(23):11432-11440.

Sakamoto, M. et al. "The Lung as a Possible Target Organ for Atrial Natriuretic Polypeptide Secreted from the Heart" Biochemical and Biophysical Research Communications, May 13, 1986, 135(2):515-520.

Salani, D. et al. "Endothelin-1 Induces an Angiogenic Phenotype in Cultured Endothelial Cells and Stimulates Neovascularization In Vivo" American Journal of Pathology, Nov. 2000, pp. 1703-1711, vol. 157, No. 5.

Sanchez-Ramos, J.R. "Neural cells derived from adult bone marrow and umbilical cord blood" J. Neurosci. Res., 2002, 69;880-893.

Saxenhofer, H. et al. "Urodilatin: binding properties and stimulation of cGMP generation in rat kidney cells" Am J Physiol Renal Physiol. 1993, pp. F267-273, vol. 264, abstract.

Scadden, A.D.J. "RNAi is antagonized by A→I hyper-editing" EMBO Reports, 2001, 11(2):1107-1111.

Scherr, M. et al. "Inhibition of GM-CSF Receptor Function by Stable RNA Interference in a NOD/SCID Mouse Hematopoietic Stem Cell Transplantation Model" Oligonucleotides, Oct. 2003, 13(5): 353-363.

Schinzel, R. et al. "The phosphate recognition site of Escherichia coli maltodextrin phosphorylase" FEBS Letters, Jul. 1991, 286(1 and 2):125-128.

Schipper, N.G.M. et al. "Chitosans as Absorption Enhancers for Poorly Absorbable Drugs. 1: Influence of Molecular Weight and Degree of Acetylation on Drug Transport Across Human Intestinal Epithelial (Caco-2) Cells" Pharmaceutical Research, 1996, 13(11):1686-1692.

Schmidt, D. et al. "Critical role for NF-$_K$B-induced JunB in VEGF regulation and tumor angiogenesis" The EMBO Journal, 2007, 26:710-729.

Schubert, S. et al. "Local RNA Target Structure Influences siRNA Efficacy: Systematic Analysis of Intentionally Designed Binding Regions" J Mol Biol, 2005, 348:883-893.

Schubert, S. et al. "Oligonucleotide-Based Antiviral Strategies" Handbook Exp Pharmacol, 2006, 173:261-287.

Schulz-Knappe, P. et al. "Isolation and Structural Analysis of "Urodilatin", a New Peptide of the Cardiodilatin-(ANP)-Family, Extracted from Human Urine" Klinische Woctienschrift, 1988, pp. 752-759, vol. 66.

(56) References Cited

OTHER PUBLICATIONS

Schwab, G. et al. "An approach for new anticancer drugs: Oncogene-targeted antisense DNA" Ann Oncol, 1994, 5(Supplement 4):S55-S58.

Schwartz, A.G. et al. "The molecular epidemiology of lung cancer" Carcinogenesis, 2007, 28:507-518.

Schwarze, J. et al. "Respiratory Syncytial Virus Infection Results in Airway Hyperresponsiveness and Enhanced Airway Sensitization to Allergen" J Clin Invest, 1997, 99:226-233.

Schwede, F. et al. "Cyclic nucleotide analogs as biochemical tools and prospective drugs" Pharmacology & Therapeutics, 2000, pp. 199-226, vol. 87.

Schweitz, H. et al. "A New Member of the Natriuretic Peptide Family is Present in the Venom of the Green Mamba (Dendroaspis angusticeps)" The Journal of Biological Chemistry, Jul. 1992, pp. 13928-13932, vol. 267, No. 20.

Scott, D.A. et al. "The Pendred syndrome gene encodes a chloride-iodide transport protein" Nature Genetics, Apr. 1999, pp, 440-443, vol. 21.

Seftor, E.A. et al. "Expression of multiple molecular phenotypes by aggressive melanoma tumor cells: role in vasculogenic mimicry" Critical Reviews in Oncology/Hematology, 2002, 44:17-27.

Seidman, C. et al. "Nucleotide sequences of the human and mouse atrial natriuretic factor genes" Science, 1984, 226:1206-1209.

Seidman, C.E. et al. "The structure of rat preproatrial natriuretic factor as defined by a complementary DNA clone" Science, 1984, 225:324-326.

Seilhamer, J.J. et al. "Human and canine gene homologs of porcine brain natriuretic peptide" Biochem. Biophys. Res. Commun., 1989, 165(2):650-658.

Sekiguchi, T. et al. "Molecular cloning of natriuretic peptide receptor a from Bullfrog (Rana catesbeiana) brain and its functional expression" Gene, 2001, 273(2):251-257.

Senger, D. et al. "Long-Term Survivors of Glioblastoma: Statistical Aberration or Important Unrecognized Molecular Subtype?" The Cancer Journal, May/Jun. 2003, pp. 214-221, vol. 9, No. 3.

Shapiro, J.A. et al. "Body Mass Index and Risk of Renal Cell Carcinoma" Epidemiology, Mar. 1999, pp. 188-191, vol. 10, No. 2.

Sharma, G.D. et al. "Expression of atrial natriuretic peptide receptor-A antagonizes the mitogen-activated protein kinases (Erk2 and P38MAPK) in cultured human vascular smooth muscle cells" Molecular and Cellular Biochemistry, 2002, 233(1-2):165-173.

Sharp, P.A. "RNA interference—2001" Genes & Development, 2001, 15:485-490.

Sharp, P.A. "RNAi and double-strand RNA" Genes & Dev., 1999, 13:139-141.

Shi, S-J. et al. "Natriuretic peptide receptor a mediates renal sodium excretory responses to blood volume expansion" Am. J. Physiol. Renal Physiol., 2003, 285:F694-F702.

Shimizu, K. et al. "Ectopic atrial natriuretic peptide production in small cell lung cancer with the syndrome of inappropriate antidiuretic hormone secretion" Cancer, 1991, 68:2284-2288.

Silberbach, M. and Roberts, Jr., C. "Natriuretic peptide signalling molecular and cellular pathways to growth regulation" Cell Signalling, 2001, 13:221-231.

Simkins, J. "Nesiritide (Natrecor®) for Decompensated CHF" in The University of Montana's School of Pharmacy and Allied Health Sciences Drug Information Service, Apr. 2002, vol. 6 No. 4.

Singam, R.V. et al. "Chitosan nanoparticle-mediated de novo synthesis of a novel natriuretic hormone peptide reverses established asthma in mice" *Journal of Allergy and Clinical Immunology*, Feb. 2004, 113(2):S325, abstract.

Skubitz. A.P.N. et al. "Differential gene expression identifies subgroups of ovarian carcinoma" Translational Research, Nov. 2006, 148(5):223-248.

Song, E. et al. "RNA interference targeting Fas protects mice from fulminant hepatitis" Nature Medicine, 2003, 9(3):347-351.

Song, S. et al. "Expression of brain natriuretic peptide by human bone marrow stromal cells" Society for Neurosci. Abstracts, 2002, Abstract No. 824.3, Meeting date Nov. 2-7, 2002.

Song, S. et al. "Expression of brain natriuretic peptide by human bone marrow stromal cells" Experimental Neurology, 2004, 185:191-197.

Song, S. et al. "Nerve growth factor and retinoic acid induce development of neuronal cells from bone marrow stromal cells of both young and old mice" Society for Neurosci. Abstracts, 2001, 27(1):940, Meeting date Nov. 10-15, 2001.

Song, S. et al. "Preparation of Neural Progenitors from Bone Marrow and Umbilical Cord Blood" in Protocols for Neural Stem Cell Methods, Zigova, T. et al., Eds., 2002, pp. 79-88.

Soutschek, J. et al. "Therapeutic silencing of an endogenous gene by systemic administration of modified siRNAs" Nature, Nov. 2004, 432:173-178.

Sporn, M.B. et al. "Chemoprevention of cancer" Carcinogenesis, 2000, 21(3):525-530.

Sprenger, H. et al. "The lack of receptors for atrial natriuretic peptides on human monocytes prevents a rise of cGMP and induction of tumor necrosis factor-alpha synthesis" Immunobiology, Sep. 1991, 183(1-2):94-101.

Steinhelper, M.E. "Structure, expression, and genomic mapping of the mouse natriuretic peptide type-B gene" Circ. Res., 1993, 72(5):984-992.

Sudoh, T. et al. "C-Type Natriuretic Peptide (CNP): A New Member of Natriuretic Peptide Family Identified in Porcine Brain" Biochemical and Biophysical Research Communications, Apr. 30, 1990, pp. 863-870, vol. 168, No. 2.

Sudoh, T. et al. "Brain natriuretic peptide-32: N-terminal six amino acid extended form of brain natriuretic peptide identified in porcine brain" Biochem Biophys Res Commun, 1988, 155:726-732.

Suenobu, N. et al. "Natriuretic peptides and nitric oxide induce endothelial apoptosis via a cGMP-dependent mechanism" Arterioscler Thromb Vasc Biol., 1999, 19:140-146.

Sumpter, W.C. "The Chemistry of Isatin" Chemical Reviews, 1944, 34(3):393-434.

Suric-Lambic, L. et al. "Vasoactive natriuretic peptides and kidney" Facta Universitatis: Medicine and Biology, 1998, 5(1):6-11.

Svoboda, P. et al. "Selective reduction of dormant maternal mRNAs in mouse oocytes by RNA interference" Development, Oct. 2000, 127:4147-4156.

Tannock, I.F. et al. "The Basic Science of Oncology, Second Edition" McGraw-Hill, Inc., New York, 1992, Chapter 19, Experimental Chemotherapy, pp. 338 and 352-359.

Tolentino, M.J. et al. "intravitreal Injection of Vascular Endothelial Growth Factor Small Interfering RNA Inhibits Growth and Leakage in a Nonhuman Primate, Laser-Induced Model of Choroidal Neovascularization" Retina, 2004, 24:132-138.

Tremblay, J. et al. "Biochemistry and physiology of the natriuretic peptide receptor guanylyl cyclases" Molecular and Cellular Biochemistry, 2002, 230:31-47.

True, D. et al. "Comparison of Kinase Assay Technologies for High Throughput Screening" poster presented at Society for Biomolecular Screening (SBS), 8th Annual Conference, Sep. 22-26, 2002.

Tunny, T.J. et al. "Association of Restriction Fragment Length Polymorphism at the Atrial Natriuretic Peptide Gene Locus with Aldosterone Responsiveness to Angiotensin in Aldosterone-Producing Adenoma" Biochemical and Biophysical Research Communications, 1994, 204:1312-1317.

Turner, G.A. et al. "Urine cyclic nucleotide concentrations in cancer and other conditions; cyclic GMP: a potential marker for cancer treatment" J Clin Pathol, 1982, pp. 800-806, vol. 35.

Tuschl, T. "Expanding small RNA interference" Nature Biotechnology, 2002, 20:446-448.

Tuschl, T. "RNA Interference and Small Interfering RNAs" Chembiochem, 2001, 2:239-245.

Tuschl, T. et al. "Targeted mRNA degradation by double-stranded RNA in vitro" Genes & Development, Dec. 1999, 13:3191-3197.

Valentin, J.P. et al. "Urodilatin Binds to and Activates Renal Receptors for Atrial Natriuretic Peptide" Hypertension, 1993, pp. 432-438, vol. 21.

Van Meir, E.G. et al. "Release of an inhibitor of angiogenesis upon induction of wild type p53 expression in glioblastoma cells" Nature Genetics, Oct. 1994, pp. 171-176, vol. 8.

(56) References Cited

OTHER PUBLICATIONS

Vellaichamy, E. et al. "Reduced cGMP signaling activates NF-$_K$B in hypertrophied hearts of mice lacking natriuretic peptide receptor-A" Biochemical and Biophysical Research Communications, 2005, 327:106-111.

Verma, I.M. et al. "Gene Therapy—promises, problems and prospects" Nature, 1997, 389:239-242.

Vesely, B.A. et al. "Urodilatin and four cardiac hormones decrease human renal carcinoma cell numbers" European Journal of Clinical Investigation, 2006, pp. 810-819, vol. 36.

Vesely, B.A. et al. "Four cardiac hormones cause cell death in 81% of human ovarian adenocarcinoma cells" Cancer Therapy, 2007, pp. 97-104, vol. 5, Issue A.

Vesely, B.A. et al. "Four Cardiac Hormones Cause Cell Death of Melanoma Cells and Inhibit Their DNA Synthesis" Am J Med Sci, 2007, 334(5):342-349.

Vesely, B.A. et al. "Four peptide hormones decrease the number of human breast adenocarcinoma cells" European Journal of Clinical Investigation, 2005, 35:60-69.

Vesely, B.A. et al. "Four cardiac hormones eliminate 4-fold more human glioblastoma cells than the green mamba snake peptide" Cancer Letters, 2007, 254:94-101.

Vesely, B.A. et al. "Four peptides decrease the number of human pancreatic adenocarcinoma cells" Eur. J. Clin. Invest., 2003, 33:998-1005.

Vesely, B.A. et al. "Primary Malignant Tumors of the Heart: Four Cardiovascular Hormones Decrease the number and DNA Synthesis of Human Angiosarcoma Cells" Cardiology, 2006, pp. 226-233, vol. 105.

Vesely, B.A. et al. "Vessel dilator: Most potent of the atrial natriuretic peptides in decreasing the number and DNA synthesis of human squamous lung cancer cells" Cancer Letters, 2006, pp. 226-231, vol. 233.

Vesely, D.L. "Aprotinin blocks the binding of pro atrial natriuretic peptides 1 to 30, 31 to 67, and 99-126 to human placental membranes" Am J Obstet Gynecol, 1991, 165(3)567-573.

Vesely, D.L. "Atrial Natriuretic Hormones Originating from the N-Terminus of the Atrial Natriuretic Factor Prohormone" Clin Exp Pharmacol Physiol, 1995, 22(2):108-114.

Vesely, D.L. "Atrial natriuretic peptides: anticancer agents" J Investig Med., 2005, 53(7):360-365.

Vesely, D.L. "Atrial natriuretic peptides in pathophysiological diseases" Cardiovascular Res., 2001, 51:647-658.

Vesely, D.L. et al. "Atrial Natriuretic Hormone, Vessel Dilator, Long-Acting Natriuretic Hormone, and Kaliuretic Hormone Decrease the Circulating Concentrations of CRH, Corticotropin, and Cortisol" J Clin Endocrinol Metab, 2001, 86:4244-4249.

Vesely, D.L. et al. "Atrial Natriuretic Hormone, Vessel Dilator, Long Acting Natriuretic Hormone, and Kaliuretic Hormone Decrease Circulating Prolactin Concentrations" Horm Metab Res, 2002, 34:245-249.

Vesely, D.L. et al. "Atrial natriuretic peptides negatively and positively modulate circulating endothelin in humans" Metabolism, 1996, 45:315-319.

Vesely, D.L. et al. "Elimination of Up to 80% of Human Pancreatic Adenocarcinomas in Athymic Mice by Cardiac Hormones" In Vivo, 2007, 21:445-452.

Vesely, D.L. et al. "Four Cardiac Hormones Eliminate up to Two-Thirds of Human Breast Cancers in Athymic Mice" In Vivo, 2007, 21:973-978.

Vesely, D.L. et al. "Long-Acting Natriuretic Peptide, Vessel Dilator, and Kaliuretic Peptide Enhance the Urinary Excretion Rate of β2-Microglobulin" Metabolism, Dec. 2000, 49(12):1592-1597.

Vesely, D.L. et al. "The N-Terminus of the Atrial Natriuretic Factor Prohormone in the Pleural Fluid of Congestive Heart Failure Patients" Chest, 1990, 97(6):1295-1298.

Vesely, D.L. et al. "Atrial Natriuretic Peptide Increases Urodilatin in the Circulation", American Journal of Nephrology, 1996, pp. 204-213, vol. 18, abstract.

Vesely, D.L. et al. "Atrial Natriuretic Prohormone Peptides 1-30, 31-67, and 79-98 Vasodilate the Aorta" Biochemical and Biophysical Research Communications, Nov. 13, 1987, pp. 1540-1548, vol. 148, No. 3.

Vesely, D.L. et al. "Increased Release of the N-Terminal and C-Terminal Portions of the Prohormone of Atrial Natriuretic Factor During Immersion-Induced Central Hypervolemia in Normal Humans" Proc Soc Exp Biol Med, 1989, pp. 230-235, vol. 192.

Vesely, D.L. et al. "Negative Feedback of Atrial Natriuretic Peptides" Journal of Clinical Endocrinology and Metabolism, 1994, pp. 1128-1134, vol. 78, No. 5.

Vesely, D.L. et al. "Novel, therapeutic approach for cancer using four cardiovascular hormones" European Journal of Clinical Investigation, 2004, pp. 674-682, vol. 34.

Vesely, D.L. et al. "Three Peptides From the Atrial Natriuretic Factor Prohormone Amino Terminus Lower Blood Pressure and Produce Diuresis, Natriuresis, and/or Kaliuresis in Humans" Circulation, 1994, pp. 1129-1140, vol. 90.

Vesely, D.L. et al. "Vessel Dilator Enhances Sodium and Water Excretion and Has Beneficial Hemodynamic Effects in Persons With Congestive Heart Failure" Circulation, 1998, pp. 323-329, vol. 98.

Vesely, D.L., "Natriuretic peptides and acute renal failure" Am J Physiol Renal Physiol, 2003, pp. F167-F177, vol. 285.

Vilimas, T. et al. "Targeting the NF-$_K$B signaling pathway in Notch1-induced T-cell leukemia" Nature Medicine, 2007, 13:70-77.

Villarreal, D. et al. "Hemodynamic and Renal Effects of ProANF31-67 in Hypertensive Rats (44399)" Proceedings of the Society for Experimental Biology and Medicine, 1999, pp. 166-170, vol. 221, No. 3.

Wong, H.H. et al. "Pancreatic cancer: molecular pathogenesis and new therapeutic targets" *Nat Rev Gastroenterol Hepatol*, 2009, 6:412-422.

Woodle, M.C. et al. "Sterically stabilized liposomes" Biochimica et Biophysica Acta: Reviews on Biomembranes, 1992, 1113:171-199.

Xia, H. et al. "siRNa-mediated gene silencing in vitro and in vivo" Nature Biotechnology, Oct. 2002, 20(10):1006-1010.

Xie, F.Y. et al. "Harnessing in vivo siRNA delivery for drug discovery and therapeutic development" *Drug Discovery Today*, Jan. 2006, 11(1/2):67-73.

Yagoda, A. et al. "Chemotherapy for Advanced Renal-Cell Carcinoma: 1983-1993" Seminars in Oncology, Feb. 1995, pp. 42-60, vol. 22, No. 1.

Yang, J. et al. "Conditional ablation of Ikkb inhibits melanoma tumor development in mice" The Journal of Clinical Investigation, Jul. 2010, 120(7):2563-2574.

Yang, J.C. et al. "Randomized Study of High-Dose and Low-Dose Interleukin-2 in Patients With Metastatic Renal Cancer" Journal of Clinical Oncology, Aug. 15, 2003, pp. 3127-3132, vol. 21, No. 16.

Yu, C.C.W. et al. "The assessment of cellular proliferation by immunohistochemistry: A review of currently available methods and their applications" The Histochemical Journal, Mar. 1992, pp. 121-131, vol. 24, No. 3.

Yu, J.Y. et al. "RNA interference by expression of short-interfering RNAs and hairpin RNAs in mammalian cells" PNAS USA, Apr. 2002, 99(9):6047-6052.

Yu, M.C. et al. "Cigarette Smoking, Obesity, Diuretic Use, and Coffee Consumption as Risk Factors for Renal Cell Carcinoma" J Natl Cancer Inst, Aug. 1986, pp. 351-356, vol. 77.

Yuhas, J.M. et al. "Specific and Nonspecific Stimulation of Resistance to the Growth and Metastasis of the Line 1 Lung Carcinoma" Cancer Research, 1975, 35:242-244.

Zamore, P.D. "Ancient Pathways Programmed by Small RNAs" Science, 2002, 296(5571):1265-1269.

Zamore, P.D. "RNA interference: listening to the sound of silence" Nature Structural Biology, Sep. 2001, 8(9):746-750.

Zamore, P.D. et al. "RNAi: Double-Stranded RNA Directs the ATP-Dependent Cleavage of mRNA at 21-23 Nucleotide Intervals" Cell, Mar. 31, 2000, 101(1):25-33.

Zeidel, M.L., "Regulation of Collecting Duct Na+ Reabsorption by ANP 31-67" Clinical and Experimental Pharmacology and Physiology, 1995, pp. 121-124, vol. 22, abstract.

(56) References Cited

OTHER PUBLICATIONS

Zellner, A. et al. "Disparity in Expression of Protein Kinase C α in Human Glioma versus Glioma-derived Primary Cell Lines: Therapeutic Implications" Clinical Cancer Research, Jul. 1998, pp. 1797-1802, vol. 4.
Zeng, Y. et al. "Both Natural and Designed Micro RNAs Can Inhibit the Expression of Cognate mRNAs When Expressed in Human Cells" Molecular Cell, Jun. 2002, 9:1327-1333.
Zhang, X. et al. "Small Interfering Rna Targeting Heme Oxygenase-1 Enhances Ischemia-Reperfusion-induced Lung Apoptosis" The Journal of Biological Chemistry, Mar. 2004, 279(11):10677-10684.
Zhou, Y. et al. "Th2 cytokines and asthma Interleukin-9 as a therapeutic target for asthma" Respiratory Research, 2001, 2:80-84.
Zimmerman, T.S. et al. "RNAi-mediated gene silencing in non-human primates" Nature, May 2006, 441:111-114.
Zips, D. et al. "New Anticancer Agents: In Vitro and In Vivo Evaluation" In Vivo, Jan./Feb. 2005, pp. 1-7, vol. 19, No. 1.
Zivin, R.A. et al. "Molecular cloning and characterization of DNA sequences encoding rat and human atrial natriuretic factors" Proc. Natl. Acad. Sci, USA, 1984, 81(20):6325-6329.
Beebe-Dimmer, J.L., et al. "Features of the Metabolic Syndrome and Prostate Cancer in African-American Men" American Cancer Society, 2007, 109:875-881.
Bell, E.N., et al. "Atrial Natriuretic Peptide Attenuates Hypoxia Induced Chemoresistance in Prostate Cancer Cells" Journal of Urology, 2007, 177:751-756.
Borsellino, N., et al. "Endogenous Interleukin 6 is a Resistance Factor for cis-Diamminedichloroplatinum and Etoposide-mediated Cytotoxicity of Human Prostate Carcinoma Cell Lines" Cancer Research, 1995, 55:4633-4639.
Cao, L., et al. "Atrial Natriuretic Peptide Suppresses the Transcription of Its Guanylyl Cyclase-linked Receptor" Journal of Biological Chemistry, 1995, 270:24891-24897.
De Marzo, A. M., et al. "Inflammation, atrophy, and prostate carcinogenesis." Urologic Oncology, 2007, 25:398-400.
De Marzo, A. M., et al. "Inflammation in prostate earcinogenesis" Nature Reviews Cancer, 2007, 7:256-269.
Foster, B.A., et al. "Characterization of Prostatic Epithelial Cell Lines Derived from Transgenic Adenocarcinoma of the Mouse Prostate (TRAMP) Model" Cancer Research. 1997, 57:3325-3330.
Goggins, W. B. and Wong. G. K.C. "Poor Survival for US Pacific Islander Cancer Patients: Evidence From the Surveillance, Epidemiology, and End Results Database: 1991 to 2004" Journal of Clinical Oncology, 2007, 25:5738-5741.
Gower, W.R., et al. "Identification, regulation and anti-proliferative role of the NPR-C receptor in gastric epithelial cells" Molecular and Cellular Biochemistry, 2006, 293:103-118.
Hamatake, M., et al. "Entratumoral Expression of Macrophage Migration Inhibitory Factor is Correlated with Serum C-Reactive Protein and Interleukin-6 in Patients with Non-Small Cell Lung Cancer" Surgery Today, 2008, 38:921-925.
He, Z., et al. "Progranulin is a mediator of the wound response" Nature Medicine, 2003, 9:225-229.
Hellermann, G., et al. "Mechanism of bronchoprotective effects of a novel natriuretic hormone peptide" Journal of Allergy and Clinical Immunology, 2004, 113:79-85.
Jiao, J., et al. "Murine Cell Lincs Derived from Pten Null Prostate Cancer Show the Critical Role of PTEN in Hormone Refractory Prostate Cancer Development" Cancer Research, 2007, 67:6083-6091.
Kawada, M., et al. "Establishment of a highly tumorigenic LNCaP cell line having inflammatory cytokine resistance" Cancer Letters, 2006, 242:46-52.
Kelloff, G.J., et al. "Agents, Biomarkers, and Cohorts for Chemopreventative Agent Development in Prostate Cancer" Urology, 2001, 57:46-51.
Kiemer, A.K. and Vollmar, A.M. "The atrial natriuretic peptide regulates the production of inflammatory mediators in macrophages," Annals of the Rheumatic Diseases, 2001, 60:iii68-iii70.
Kong, X., et al. "Natriuretic Peptide Receptor A as a Novel Anticancer Target" Cancer Research, 2008, 68:249-256.
Kumar, M., et al. "Atrial natriuretic peptide gene transfer by means of intranasal administration attenuates airway reactivity in a mouse model of allergic sensitization,"Journal of Allergy and Clinical Immunology, 2002, 110:879-882.
Le, N.T., et al. "The dual personalities of matrix metalloproteinases in inflammation" Frontiers in Bioscience, 2007, 12;1475-1487.
Liu, X.H., et al. "Prostaglandin $E_2$ Stimulates Prostatic Intraepithelial Neoplasia Cell Growth through Activation of the Interleukin-6/ GP130/STAT-3 Signaling Pathway" Biochemical and Biophysical Research Communications, 2002, 290:249-255.
Lopez, M.J., et al. "Salt-resistant hypertension in mice lacking the guanylyl cyclase-A receptor for atrial natriuretic peptide" Letters to Nature, 1995, 378:65-68.
Mentor-Marcel, R., et al. "Genistein in the Dict Reduces the Incidence of Poorly Differentiated Prostatic Adenocarcinoma in Transgcnic Mice (TRAMP)." Cancer Research, 2001, 61:6777-6782.
Meyer-Siegler, K.L., et al. "Further evidence for increased macrophage migration inhibitory factor expression in prostate cancer" BMC Cancer, 2005, 5:73.
Meyer-Siegler, K.L., et al. "Inhibition of Macrophage Migration Inhibitory Factor or Its Receptor (CD74) Attenuates Growth and Invasion of DU-145 Prostate Cancer Cells" Journal of Immunology, 2006; 177:8730-8739.
Meyer-Siegler, K.L., et al. "Macrophage migration inhibitory Factor (MIF) gene polymorphisms arc associated with increased prostate cancer incidence" Genes and Immunity, 2007, 8:646-652.
Michalaki, V., et al. "Scrum levels of IL-6 and TNF-α correlate with clinicopathological features and patient survival in patients with prostate cancer." British Journal of Cancer, 2004, 90:2312-2316.
Miller, B. A., et al. "Cancer Incidence and Mortality Patterns among, Specific Asian and Pacific Islander Populations in the U.S." Cancer Causes and Control, 2008, 19(3):227-258.
Mohapatra, S., et al. "Accumulation of p53 and Reductions in XIAP Abundance Promote the Apoptosis of Prostate Cancer Cells" Cancer Research, 2005, 65:7717-7723.
Mohapatra, S.S. "Role of natriuretic peptide signaling in modulating asthma and inflammation." Canadian Journal of Physiology and Pharmacology, 2007, 85:754-759.
Mohapatra, S.S., et al. "Natriuretic peptides and genesis of asthma: An emerging paradigm?" Journal of Allergy and Clinical Immunology, 2004, 114:520-526.
Nelson, J.E. and Harris, R.E. "Inverse association of prostate cancer and non-steroidal anti-inflammatory drugs (NSAIDs): results of a case-control study" Oncology Reports, 2000, 7:169-170.
Nelson, W. G. "Prostate cancer prevention" Current Opinion in Urology, 2007, 17:157-167.
Patel, J. B., et al. "Cardiac-specific attenuation of natriuretic peptide a receptor activity accentuates adverse cardiac remodeling and mortality in response to pressure overload" American Journal of Physiology, Heart and Circulatory Physiology, 2005, 289:H777-H784.
Paule, B., et al. "The NF-KB/IL-6 pathway in metastatic androgen-independent prostate cancer: new therapeutic approaches?" World Journal of Urology, 2007, 25:477-489.
Rodriguez, C., et al. "Use of blood-pressure-lowering medication and risk of prostate cancer in the Cancer Prevention Study II Nutrition Cohort" Cancer Causes Control, 2009, 20(5):671-9.
Salama, I., et al. "A review of the S100 proteins in cancer" European Journal of Surgical Oncology, 2008, 34:357-364.
Smith, P.C. and Keller, E.T., "Anti-Interleukin-6 Monoclonal Antibody Induces Regression of Human Prostate Cancer Xenografts In Nude Mice" The Prostate, 2001, 48:47-53.
Smith, P.C., et al. "Mini Review, Interleukin-6 and prostate cancer progression" Cytokine and Growth Factor Reviews, 2001, 12:33-40.
Stark, J.R., et al. "Circulating Pre-Diagnostic haerleukin-6 and C-Reactive Protein and Prostate Cancer Incidence and Mortality" International Journal of Cancer, 2009, 124(11):2683-2689.
Sun, Y., et al. "Atrial Natriuretic Peptide and Long Acting Natriuretic Peptide Inhibit ERK 1/2 in Prostate Cancer Cells" Anticancer Research, 2006, 26: 4143-4148.

(56) References Cited

OTHER PUBLICATIONS

Sun, Y., et al. "Vessel Dilator and Kaliuretie Peptide Inhibit ERK 1/2 Activation in Human Prostate Cancer Cells" *Anticancer Research*, 2006, 26:3217-3222.

Sun, Y., et al. "Vessel Dilator and Kaliuretic Peptide Inhibit MEK 1/2 Activation in Human Prostate Cancer Cells" *Anticancer Research*, 2007, 27:1387-1392.

Teiun, M.J., et al. "Nonsteroidal Anti-inflammatory Drugs as Anticancer Agents: Mechanistic, Pharmacologic, and Clinical Issues" *Journal of the National Cancer Institute*, 2002, 94:252-266.

Tumminello, F.M., et al. "Serum interleukin-6 in patients with metastatic bone disease: correlation with cystatin C" *Medical Oncology*, 2009, 26:10-15.

Vesely, B.A., et al. "Five cardiac hormones decrease the No. Of human small-cell lung cancer cells" *European Journal of Clinical Investigation*, 2005, 35:388-398.

Vesely, B.A., et al. "Four peptide hormones' specific decrease (up to 97%) of human prostate carcinoma cells" *European Journal of Clinical Investigation*, 2005, 35:700-710.

Vesely, D.L. "Atrial Natriuretic Peptide Prohormone Gene Expression: Hormones and Diseases That Upregulate its Expression" TUBMB Life, 2002, 53: 153-159.

Vesely, D.L., et al. "Vessel Dilator, Long Acting Natriuretic Peptide, and Kaliuretic Peptide Increase Circulating Prostaglandin $E_2$" *Life Sciences*, 2000, 66(10): 905-913.

Wang, X., et al. "Natriuretic Peptide Receptor A as a Novel Target for Prostate Cancer" *Molecular Cancer*, 2011, 10:56.

Wang, X., et al. "Prevention of airway inflammation with topical cream containing imiquimod and small interfering RNA for natriuretic peptide receptor" *Genetic Vaccines and Therapy*, 2008, 6:7.

Wang, X., et al. "Modulation of lung inflammation by vessel dilator in a mouse model of allergic asthma" *Respiratory Research*, 2009, 10:66.

Office Action dated Jan. 22, 2013 in U.S. Appl. No. 12/679,630, filed Jun. 28, 2010.

Bradfute SB et al., "Roles of Sca-1 in hematopoietic stem/progenitor cell function" *Experimental Hematology*, 2005, 33:836-843.

Delorme B and Charbord P, "Culture and Characterization of Human Bone Marrow Mesenchymal Stem Cells" *Methods in Molecular Medicine*, 2007, 140:67-81.

Hattan N et al., "Purified cardiomyocytes from bone marrow mesenchymal stem cells produce stable intracardiac grafts in mice" *Cardiovascular Research*, 2005, 65:334-344.

Lu Y et al., "Human Bone Marrow Mesenchymal Stem Cells Transfected with Human Insulin Genes Can Secrete Insulin Stably" *Annals of Clinical & Laboratory Science*, 2006, 36(2):127-136.

Nadri S et al., "An efficient method for isolation of murine bone marrow mesenchymal stem cells" *International Journal of Developmental Biology*, 2007, 51:723-729.

Zahabi A et al., "Expression of Constitutively Active Guanylate Cyclase in Cardiomyocytes Inhibits the Hypertrophic Effects of Isoproternol and Aortic Constriction on Mouse Hearts" *The Journal of Biological Chemistry*, 2003, 278(48):47694-47699.

Office Action dated Jun. 12, 2013 in U.S. Appl. No. 11/998,972, filed Nov. 30, 2007.

Wang X et al., "Natriuretic Peptide Receptor a as a Novel Target for Prostate Cancer" *Molecular Cancer*, 2011, 10:56, pp. 1-12.

Opalinska JB et al., "Nucleic-acid therapeutics: Basic principles and recent applications" *Nature Reviews Drug Discovery*, 2002, 1:503-514.

Office Action dated Sep. 6, 2013 in U.S. Appl. No. 12/679,630, filed Jun. 28, 2010.

Wang X et al., "The Role of Sca-1+/CD31_ Cardiac Progenitor Cell Population in Postinfarction Left Ventricular Remodeling" 2006, *Stem Cells*, 24:1779-1788.

Gojo S et al., "In vivo cardiovasculogenesis by direct injection of isolated adult mesenchymal stem cells" *Experimental Cell Research*, 2003, 288:51-59.

"Clinical Aspects of Cancer, Diagnosis" from Merck Manual; http://www.merck.com/mmpe/sec11/ch147/ch147c.html; accessed Jul. 25, 2007, 5 pages.

"Introduction to Cancer" from Merck Manual; http://www.merck.com/mmpe/sec11/ch147/ch147a.html?qt=cancer&alt=sh; accessed Jul. 25, 2007, last modified Nov. 2005, 1 page.

"Peptide hormones" http://web.indstate.edu/thcme/mwking/peptide-hormones.html; accessed Jul. 23, 2007, 15 pages; from "The Medical Biochemistry Page" of Dr. Michael W. King of Indiana University.

GenBank Accession No. AAA37670; version AAA37670.1, GI:309246 (Jun. 12, 1993), pp. 1-2.

GenBank Accession No. AAD14112; version AAD14112.1, GI:4261812 (Feb. 10, 1999), pp. 1-2.

GenBank Accession No. AAF01340; version AAF01340.1, GI:6013455 (Oct. 6, 1999), pp. 1-3.

GenBank Accession No. CAI13613.1; version CAI13613.1, GI:55962127 (Jan. 13, 2009), 1-3.

GenBank Accession No. AAI10660; version AAI10660.1, GI:83404966 (Sep. 8, 2006), pp. 1-3.

GenBank Accession No. AAA66945, version AAA66945.1, GI:473634 (May 18, 1995), pp. 1-2.

GenBank Accession No. NM_000906; version NM_000906.3, GI:167830410 (Jul. 21, 2012), pp. 1-6.

\* cited by examiner

NATRIURETIC PEPTIDE RECEPTOR AS A BIOMARKER FOR DIAGNOSIS AND PROGNOSIS OF CANCER

CROSS-REFERENCE TO RELATED APPLICATIONS

The present application claims the benefit of U.S. Provisional Application Ser. No. 61/453,646, filed Mar. 17, 2011, which is hereby incorporated by reference herein in its entirety, including any figures, tables, or drawings.

BACKGROUND OF THE INVENTION

Advances in the fields of genomics and proteomics have helped to advance basic knowledge of cancer biology leading to identification of cancer biomarkers and development of new methods of diagnosis and disease prognosis. Biomarkers are biological molecules that are indicators of physiologic state and also of change during a disease process.

The utility of a biomarker lies in its ability to provide an early indication of the disease, to monitor disease progression, to provide ease of detection, and to provide a factor measurable across populations. The sequencing of the human genome has set the pace for biomarker discovery and provided the impetus for the next level of molecular inquiry, which is represented by functional genomics or proteomics. These approaches have led to the identification of numerous molecular signatures for either prognosis or prediction of a diverse array of cancers linked to specific disease phenotypes. However, only a limited number of these have been validated, commercialized and brought forward to the clinic. To be clinically useful, a molecular signature should have independent predictive value superior to pathological staging. An alternative method of detecting biomarkers is referred to candidate approach, whereby a selected protein is tested as candidate biomarker by its expression levels and its physiological role in the cancer pathogenesis.

It has been reported that NPRA expression and signaling is important for tumor growth (3). NPRA-deficient mice showed significantly reduced antigen-induced pulmonary inflammation. NPRA deficiency also substantially protected C57BL/6 mice from lung, skin, and ovarian cancers. Furthermore, a nanoparticle-formulated interfering RNA for NPRA attenuated B16 melanoma tumors in mice. Ectopic expression of a plasmid encoding NP73-102, the NH(2)-terminal peptide of the ANP prohormone, which down-regulates NPRA expression, also suppressed lung metastasis of A549 cells in nude mice and tumorigenesis of Line 1 cells in immunocompetent BALB/c mice. The antitumor activity of NP73-102 was in part attributed to apoptosis of tumor cells. Western blot and immunohistochemistry staining indicated that the transcription factor, nuclear factor-kappaB, was inactivated, whereas the level of tumor suppressor retinoblastoma protein was up-regulated in the lungs of NPRA-deficient mice. Furthermore, expression of vascular endothelial growth factor was down-regulated in the lungs of NPRA-deficient mice compared with that in wild-type mice. These results suggest that NPRA is involved in tumor angiogenesis.

It was also reported that atrial natriuretic peptide receptor A (NPRA) protein is expressed in various tumor cell lines, including the androgen-independent human prostate cancer (PCa) cell line DU145, but not in NIH 3T3, a normal mouse fibroblast cell line, and NHBE, a normal human bronchial epithelial cell line. Further, NPRA protein is also detectable in the human PCa cell line PC3. However, to date the expression levels of NPRA in human tumor tissues is largely unknown and the clinical relevance of NPRA is unclear.

Prostate cancer (PCa) is the third leading cause of death among men in America [1, 2]. The mortality from PCa results from metastases to bones and lymph nodes and progression from androgen-dependent to androgen-independent disease. While androgen deprivation has been effective in treating androgen-dependent PCa, it is ineffective in treating advanced PCas, the primary cause of mortality. Epidemiological and histopathological studies have implicated inflammation in the pathogenesis of PCa [3-5]. Studies have consistently shown a decreased risk of PCa among men who regularly take aspirin or other non-steroidal anti-inflammatory drugs (NSAIDs) [6-8]. Despite beneficial effects, the side effects from using high doses of COX-2 inhibitors for cancer prevention are a major concern. These observations emphasize the need for development of new effective treatments for advanced PCa.

The family of natriuretic peptide hormones has broad physiologic effects. In addition to vasodilation, cardiovascular homeostasis, sodium excretion and inhibition of aldosterone secretion, they have been implicated in immunity and inflammation [9-18]. The effects of atrial natriuretic peptide (ANP) are mediated by its interaction with the cell surface natriuretic peptide receptor A (NPRA; high affinity) and natriuretic peptide receptor C (NPRC; low affinity). In patients with prostate tumors, the immune response plays a large part in the progression of the disease and it is likely that the NPRA system is involved; but the role of NPRA in human cancers remains unknown. The peptide $NP_{73-102}$ [14], whose sequence is immediately N-terminal to the ANP peptide, is an inhibitor of NPRA (iNPRA). $NP_{73-102}$ does not bind to NPRA but blocks its expression, and it has been shown that it possesses bronchodilatory, anti-inflammatory [14, 16, 19, 20] and anti-tumor activity [19].

It was previously reported that mice deficient in NPRA (NPRA-knockout, KO) exhibit significantly decreased inflammation [16, 19-21]. Furthermore, it was found that NPRA-KO mice do not permit growth of implanted human lung cancer, melanoma and ovarian cancer cells [19], suggesting that NPRA may be a novel therapeutic candidate.

BRIEF SUMMARY OF THE INVENTION

The invention pertains to biomarkers for clinical detection of a number of malignancies, especially for early detection of cancers. More specifically, this invention pertains to the role of Natriuretic Peptide Receptor A (NPRA) in cancer (e.g., tumor) progression, as its expression has been examined in a number of contexts, such as in benign prostatic hyperplasia (BPH), high grade PIN (prostatic intraepithelial neoplasm) and prostatic adenocarcinoma. NPRA expression was examined in a human PCa tissue microarray (TMA) containing 240 samples. The TMA samples included BPH, regular prostatic intraepithelial neoplasm (PIN-R), high PIN (PIN-H), prostate carcinoma (PC) with a Gleason score of 6, PC with a Gleason score of 7, PC with a Gleason score of 8 and up and androgen-independent (AI) PC. The TMA slide was stained using an in-house human NPRA antibody in a Ventana Discovery XT automated system and the data statistically analyzed. Epithelial cell NPRA staining was weak for the majority of BPH and PIN-R samples, weak to moderate in PIN-H, moderate to strong in Gleason-6 and uniformly strong in epithelial tumors of Gleason-7 and -8 and in AI samples. Moderate staining was seen in stromal and inflammatory cells. Analyses of medians by chi-square and P-K test showed a strong association between intensity of NPRA staining and PCa stage. In other embodiments of this invention the expression of NPRA was associated with early detection of colon cancer, detection of breast cancer, detection of pancreatic cancer, detection of markell cell carcinoma, GIST tumors and melanoma. Although NPRA expression was found not to be associated with ovarian cancer or melanoma, NPRA may constitute a diagnostic and prognostic marker in many other cancers. The contents of Wang et al., "Natriuretic Peptide Receptor A as a Novel Target for Prostate Cancer," *Molecular Cancer*, 2011, 10:56, is incorporated herein by reference in its entirety.

One aspect of the invention provides a method of detecting a malignancy in a subject, comprising obtaining a sample of cells from the subject, and determining whether the expression level (abundance) or activity of NPRA in cells of the sample is elevated relative to an appropriate control (comparing the determined NPRA expression level to an appropriate control). NPRA expression levels can be determined by determining the amount of genetic material encoding NPRA (e.g., DNA or mRNA transcripts) or the amount NPRA protein.

The appropriate control may be, for example, an NPRA expression level or activity in normal cells of the individual, an NPRA expression level or activity in normal cells of another individual or a group of individuals, or other reference NPRA expression level or activity. Preferably, the normal cells are normal cells of the same cell type under study in the sample. A case in which NPRA level or activity is elevated (e.g., over-expressed) relative to NPRA level or activity in the normal control cells is indicative of cancer.

The appropriate control may be NPRA level or activity in one or more types of cancer cells. The appropriate control may be NPRA level or activity in one or more stages of a cancer, in order to accurately stage cancer in the sample for diagnosis and/or prognosis of the disease. The NPRA expression level or activity in cancer cells may be from cells of the individual (e.g., obtained from the individual at a prior time, such as before treatment or earlier in a treatment regimen), or before or after the cancer diagnosis. In some embodiments, the NPRA expression level or activity of the sample is compared to that of normal cells, cancer cells, or both. In some embodiments, the control cells are primary cells and not a cell line. In some embodiments, the control cells are cells of a cell line.

Cancers that may be detected include, but are not limited to, prostate cancer, colon cancer, breast cancer, pancreatic cancer, Merkell cell carcinoma, and GIST.

The sample may be any biological sample comprising the cells of interest, or genetic material (e.g., DNA or RNA) encoding NPRA or NPRA protein obtained from sample cells of interest. For example, the sample may comprise tumor cells from the subject. In some embodiments, the sample comprises tissue or cells adjacent to a tumor in the subject. In some embodiments, the mammalian subject is a human and the cells are human cells. In some embodiments, the cells are primary cells, and not cells of a cell line.

Optionally, the methods of the invention further comprise carrying out at least one confirmatory test for the cancer if NPRA is determined to be over-expressed. Confirmatory tests for cancer vary with the cancer type. For example, confirmatory tests for colorectal cancer include, but are not limited to, a blood test, test for blood in a stool sample, test for a target microorganism in a stool sample, colonoscopy, sigmoidoscopy, X-ray with barium, computerized axial tomography, and capsule tomography, or a combination of two or more of the foregoing.

Another aspect of the invention concerns a method of treating a malignancy in a subject from whom a sample of cells (e.g., tumor cells) has been determined to have elevated NPRA level or activity. In some embodiments, the method comprises obtaining a sample comprising cells from the subject; determining whether NPRA is over-expressed in the cells (e.g., relative to an appropriate control), wherein NPRA over-expression is indicative of the cancer; and treating the subject with a therapy for the cancer if NPRA is over-expressed. Optionally, the determined NPRA expression level can be compared to a control known to have one or more cancers. Optionally, the method further comprises carrying out at least one confirmatory test for the cancer if NPRA is determined to be over-expressed.

The therapy or therapies used for treating the subject determined to have a malignancy can be selected by a clinician (such as an oncologist) and will depend upon the cancer type. For example, in the case of colorectal cancer, the therapy may comprise bowel diversion therapy, a chemotherapeutic, and radiation therapy, or a combination of two or more of the foregoing. These and other appropriate treatment regimens and procedures that may used for treatment of cancer are known to those of ordinary skill in the art.

Normally, cancer progression is generally unpredictable, with cancer diagnosis providing little guidance as to whether the cancer will progress aggressively or spontaneously regress in an individual. The present invention provides diagnostic methods for differentiating low grade cancers (e.g., low grade tumors) from high grade cancers (e.g., high grade tumors) by correlating the level of NPRA to favorable or unfavorable prognosis. The basic method involves (a) obtaining a sample of cells suspected of containing cancer cells; (b) analyzing the sample for NPRA level or activity; (c) correlating the NPRA level or activity with a control or standard NPRA level or activity; and (d) relating a high NPRA level or activity relative to said standard NPRA level or activity as an indication of unfavorable cancer prognosis, and a low NPRA level or activity relative to said standard NPRA level or activity equal to said standard level or activity as an indication of favorable cancer prognosis. The standard value can be a predetermined level obtained from assaying cells known to have low NPRA level or activity. Alternatively the standard value can be determined from a range of NPRA levels or activities known to be associated with the different clinical outcomes of cancer progression.

Another aspect of the invention concerns a method of monitoring cancer in a subject diagnosed with cancer, comprising obtaining a sample comprising cells from the subject; determining the NPRA level or activity in the cells; comparing the determined NPRA level or activity to an NPRA level or activity in a sample of cells previously obtained from the subject.

Another aspect of the invention concerns a method of determining the expression of NPRA in cells of subject that has been diagnosed with cancer, comprising obtaining a sample comprising cells from the subject, and determining the amount of NPRA expression (e.g., the amount of NPRA messenger RNA or protein) in cells of the sample. In some embodiments, the method comprises obtaining a series of samples from the subject over time and determining the amount of NPRA expression in the samples to monitor NPRA expression over time. The NPRA expression levels determined can be compared to an appropriate control and compared to one another to determine the status of the cancer and/or the subject's responsiveness to a treatment.

Another aspect of the invention concerns an immunoassay for determining whether a subject has a malignancy by detecting elevated NPRA, and a kit for conducting the immunoassay, the kit comprising a first container comprising an anti-NPRA antibody of the invention.

Another aspect of the invention concerns an in vitro polymerase chain reaction (PCR) assay kit for determining whether a subject has a cancer by detecting over-expression of NPRA, the kit comprising a first container comprising PCR primers that amplify an NPRA transcript or cDNA generated therefrom; and a second container comprising a nucleic acid marker, said marker being and labeled and able to hybridize to said transcript or cDNA. Optionally, the kit further comprises printed instructions for determining over-expression of NPRA.

Another aspect of the invention is a purified or isolated immunological reagent, such as an antibody or antibody fragment, that binds to NPRA protein. Preferably, the immunological reagents binds to human NPRA. In some embodiments, the immunological reagent binds to both human and mouse NPRA. In some embodiments, the immunological reagent is a monoclonal antibody or polyclonal antibody. In some embodiments, the immunological reagent binds to an epitope within the amino acid sequence of SEQ ID NO:1, SEQ ID NO:2, or SEQ ID NO:3. In some embodiments, the immunological reagent binds to an epitope comprising or consisting of the amino acid sequence SEQ ID NO:1, 2, or 3.

Another aspect of the invention is a method for inhibiting the growth of a malignant cell in vitro or in vivo, comprising administering an agent to the cell, wherein the agent inhibits the function of migration inhibitor factor (MIF) in the malignant cell. In some embodiments, the agent is administered in vivo to a human or non-human mammal. The agent may be administered in vivo systemically or locally, directly at the site of the malignant cells. For example, if the mammal has tumor comprising malignant cells, the agent may be administered directly to the tumor (e.g., intra-tumorally).

In some embodiments, the agent targets a nucleic acid sequence within the MIF gene or transcript and reduces expression of MIF in the malignant cell (e.g., complete silencing of gene expression or partial knockdown). In some embodiments, the malignant cell is a cancer cell selected from the group consisting of prostate cancer, colon cancer, breast cancer, pancreatic cancer, Merkell cell carcinoma, and gastrointestinal stromal tumor (GIST). In some embodiments, the agent is a nucleic acid inhibitor selected from an RNA interference (RNAi) molecule (e.g., siRNA, shRNA), microRNA (miRNA), antisense oligonucleotide, or ribozyme that targets a target nucleic acid sequence within the MIF gene or transcript and reduces expression of MIF in the malignant cell. In some embodiments, the nucleic acid inhibitor comprises a nucleic acid sequence that is complementary with a target sequence within the MIF gene or transcript.

In each aspect of the invention, the subject may be one that has been diagnosed with the malignancy (for example, prostate cancer, colon cancer, breast cancer, pancreatic cancer, Merkell cell carcinoma, GIST), or may be a subject that has not yet been diagnosed with the malignancy.

Another aspect of the invention includes a method for providing an NPRA expression profile useful for detecting and/or prognosing cancer.

The terms "CaP" and "PCa" are used interchangeably herein to refer to cancer of the prostate.

BRIEF DESCRIPTION OF THE DRAWINGS

In FIG. 1A, cell lysates were subjected to SDS-PAGE/immunoblot analysis with rabbit polyclonal antibody specific for human NPRA (top) and β-actin (bottom). FIG. 1B shows Western blotting for NPRA expression. β-actin expression was used as loading control. In FIGS. 1C and 1D, whole cell lysates of TRAMP-C1, C2 and C3 cell lines (FIG. 1C) and CaP2 and P2 cells (FIG. 1D) were analyzed by western blotting for NPRA expression.

FIG. 9A shows that NPRA-deficiency impaired engraftment of TRAMP-C1 cells. Three groups of mice (wild type (WT), heterozygous (Het) and homozygous (NPRA-KO), (n=5 per group) were injected s.c. in the left and right flanks with $5 \times 10^6$ TRAMP-C1 cells per site. Mice were euthanized ten weeks after injection. Tumors were excised and weighed. Mean tumor weights ±SEM are shown in FIG. 9A. NPRA deficiency induced apoptosis of PCa cells. TRAMP-C1 cells were transiently transfected with psiNPRA (si1 and si2) and control plasmid (pU6). Cells were harvested 72 hrs later and whole cell lysates were analysed for NPRA and PARP by Western blotting. Results are shown in FIG. 9B. TRAMP-C1 cells were transfected with pU6 or psi-2 plasmids. Forty-eight hours after transfection, apoptosis was monitored by TUNEL assay. Results are shown in FIG. 9C.

Figure 11A:
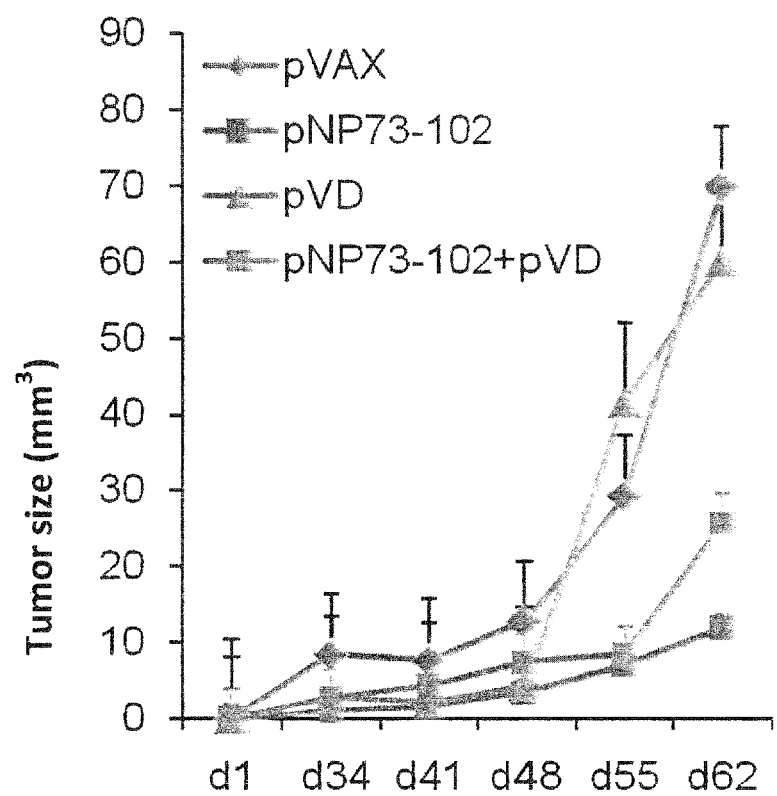
FIGS. 11A-C show effects of iNPRA in TRAMP-C1 inoculated xenografts in immunocompetent mice, and correlation of NPRA expression with MIF expression. Four groups of C57BL/6 mice (n=7 per group) were injected s.c.
Figure 11B:
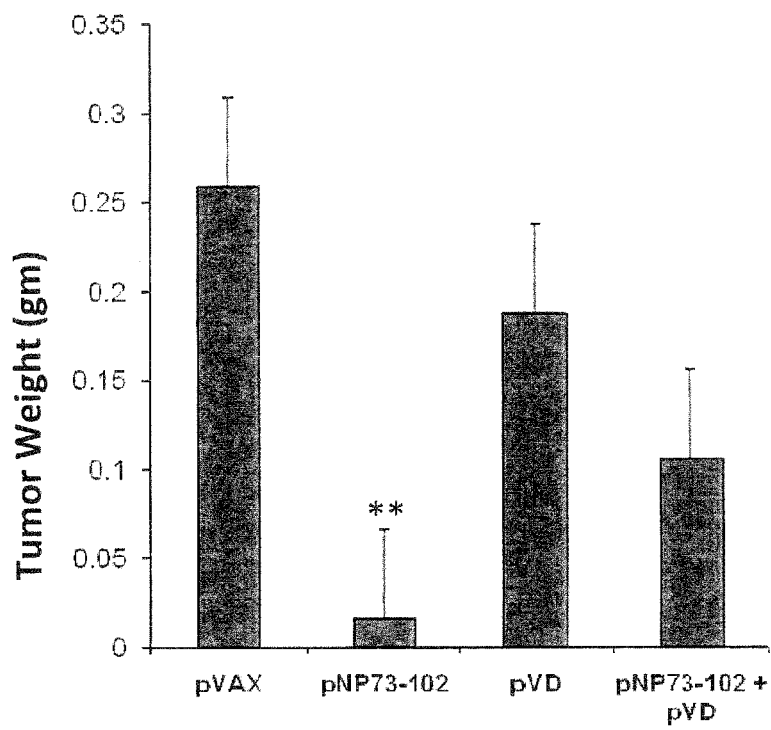

in the right flank with 5×10⁶ TRAMP-C1 cells. Two weeks later, tumor inoculated mice were treated with CNPs encapsulated with pVAX, pNP$_{73-102}$, pVD or a combination of pNP$_{73-102}$ and pVD i.p. twice a week until euthanized. The tumor size (FIG. 11A) was measured at the indicated days, and the weight was recorded after tumor resection (FIG. 11B). NPRA expression correlates with MIF expression in tumor lysates. Tumor lysates from B were analysed for NPRA and MIF by Western blotting. Results are shown in FIG. 11A. pVAX (lanes 1-3) and pNP$_{73-102}$ (lanes 4-6). β-actin was used as a loading control.

Figure 12A:
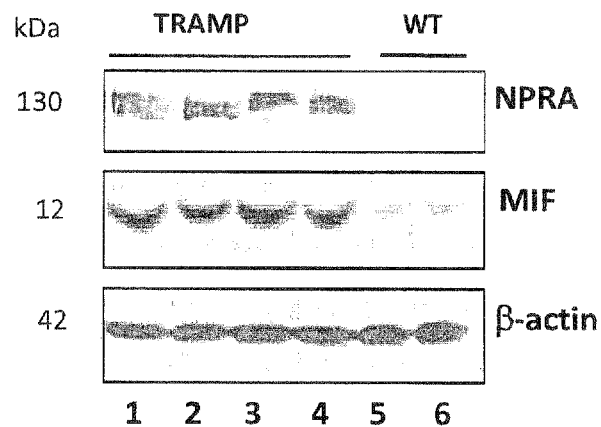
Figure 12B:
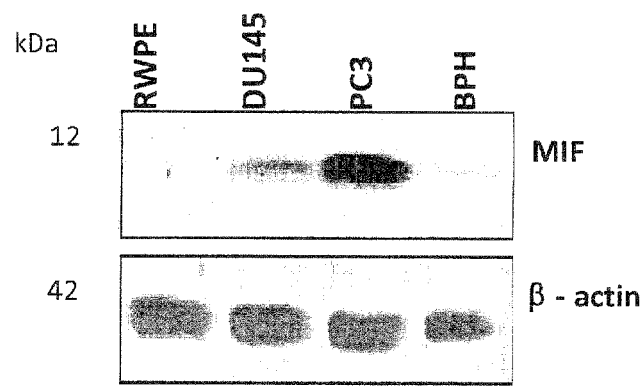

FIGS. 12A-B show NPRA and MIF expression in primary prostate tumors. Prostate tissues were homogenized using a polytron and cell lysates were analyzed for NPRA and MIF by Western blotting. Results are shown in FIG. 12A. Lanes 1-4: lysates of TRAMP prostates. Lanes 5-6: lysates of C57BL/6 prostates. Whole cell lysates of tumor cell lines and control (normal) cells were analysed by Western blotting. Results are shown in FIG. 12B.

Figure 13A:
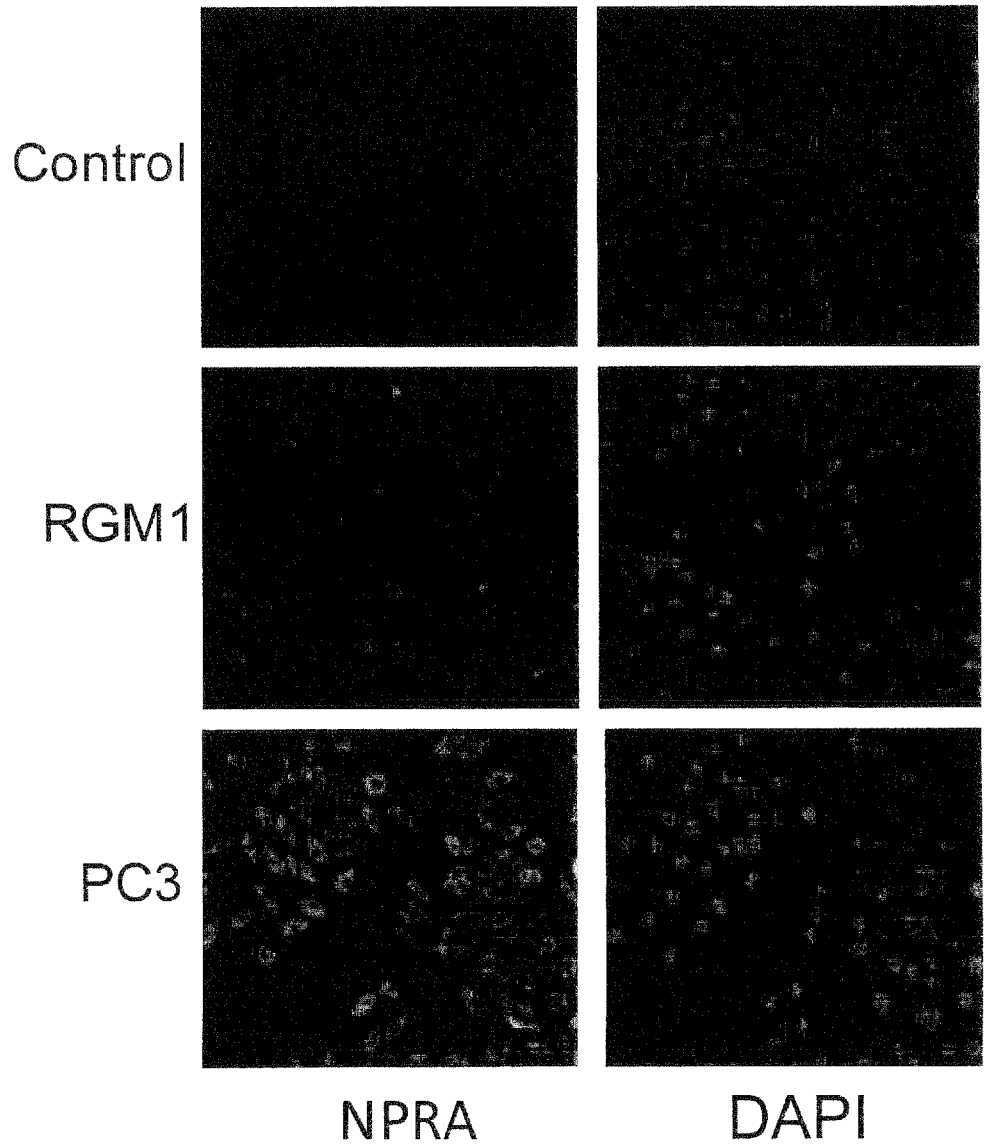
Figure 13B:
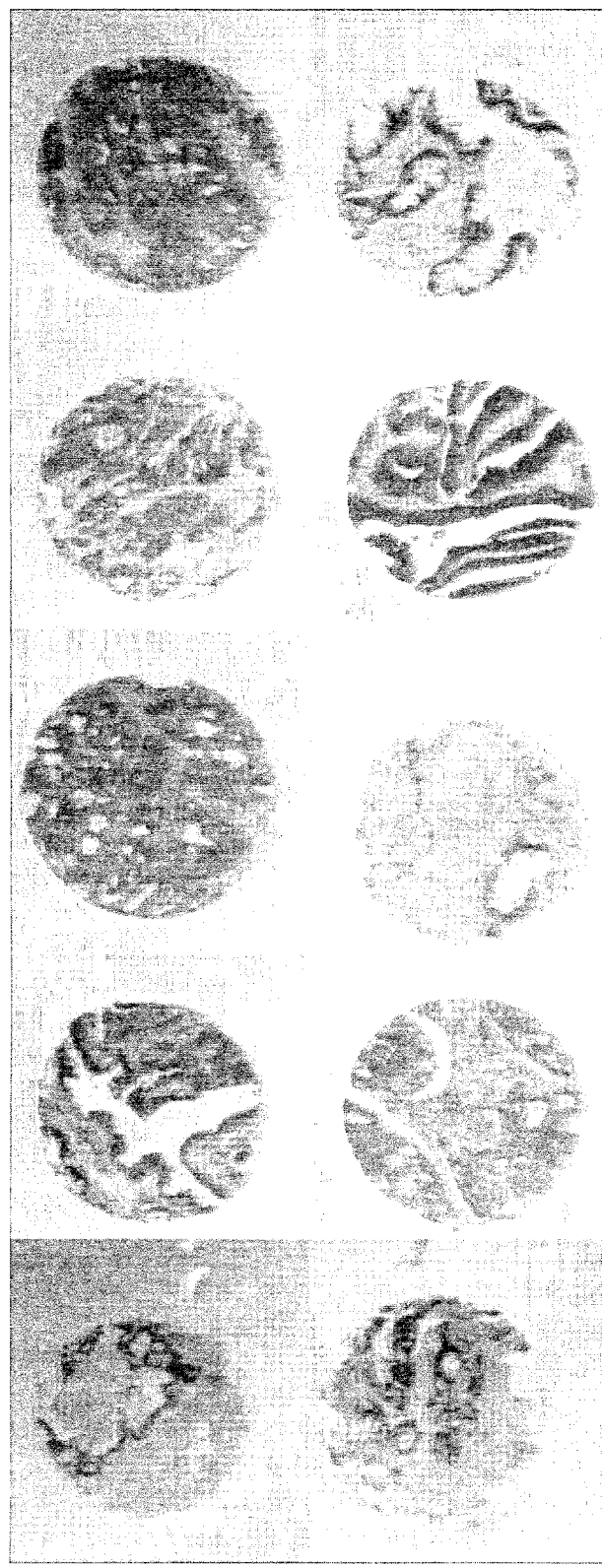
Figure 13C:
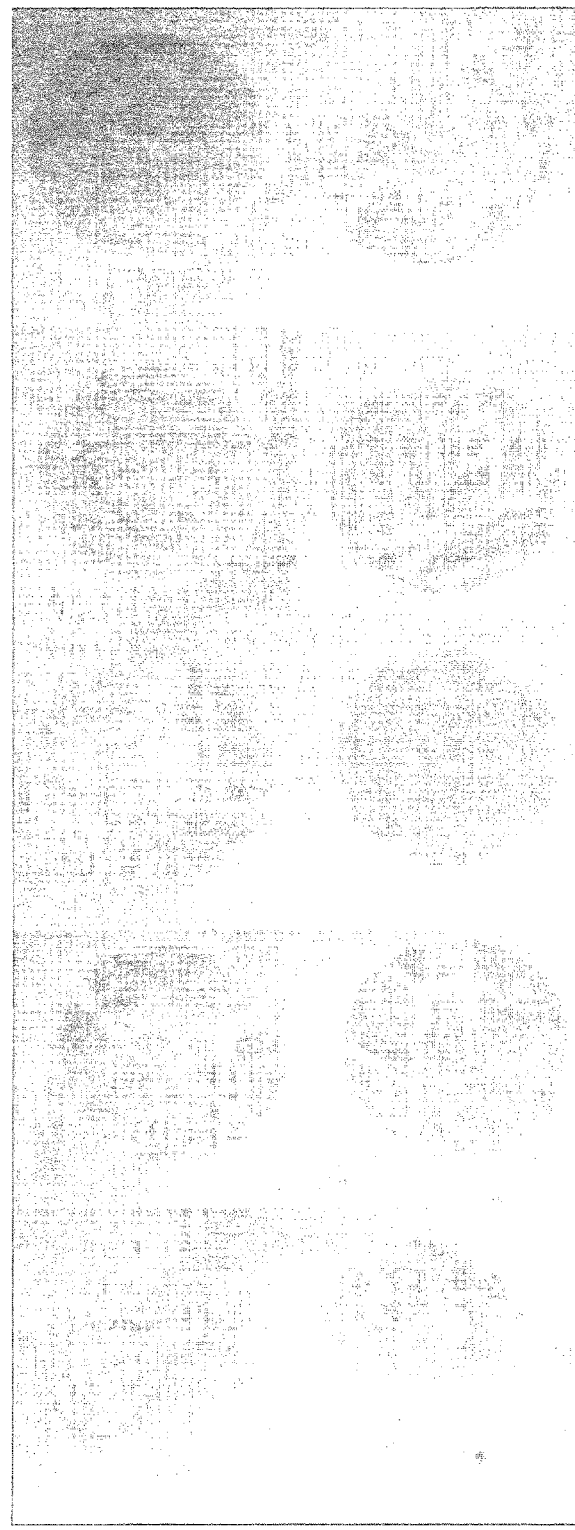

FIGS. 13A-C show immunofluorescence (A), and immunohistochemistry (B-C) with an anti-NPRA antibody. In FIG. 13A, the indicated cell lines were cultured on chamber slide and immunostained using anti-NPRA Ab. As a negative control, PC3 cells were incubated with secondary Ab alone (Control). In FIGS. 13B and 13C, two identical multi-tissue TMA slides containing colon, prostate, breast, and pancreas tumor tissues were used to optimize immunostaining. The slide in FIG. 13C was incubated with secondary Ab only.

Figure 14A:
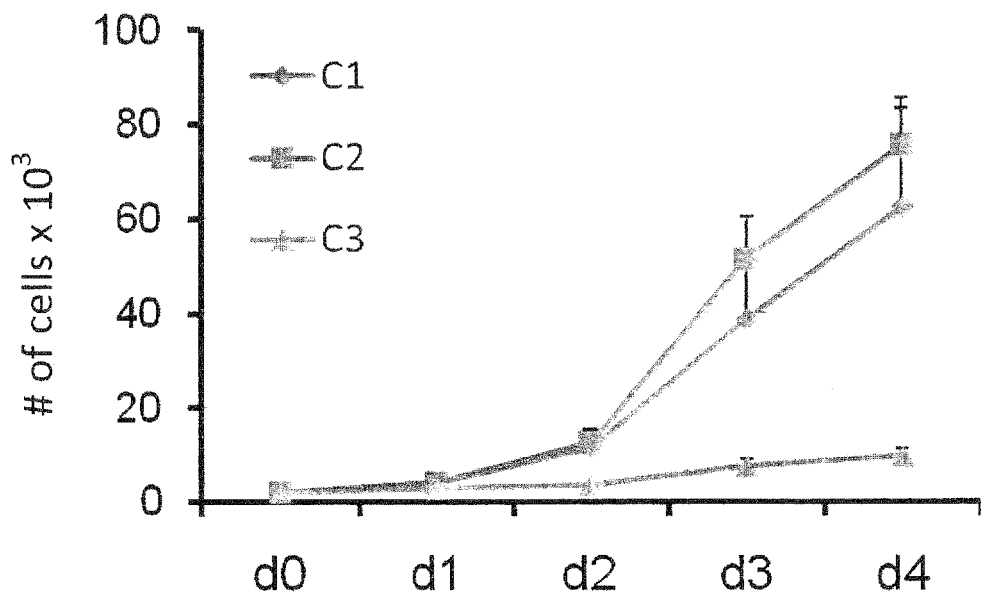
Figure 14B:
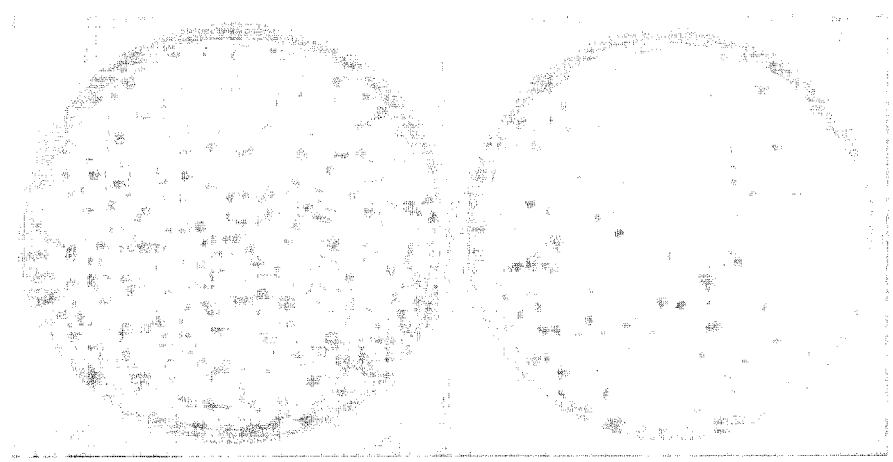
Figure 14C:
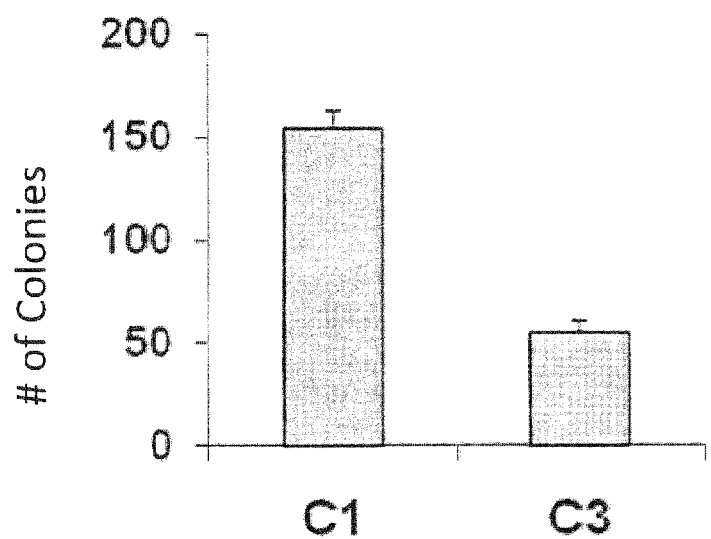

FIGS. 14A-C show results of analysis of TRAMP-C1 (TR-C1), TRAMP-C2 (TR-C2), and TRAMP-C3 (TR-C3) cells. In FIG. 14A, TRAMP-C1, -C2 and -C3 cells were plated at 10⁵ cells per plate for 4 days and viable cell numbers were enumerated at the indicated days by trypan blue dye-exclusion. In FIGS. 14B and 14C, TRAMP-C1 or TR-C3 cells were plated in 100 mm dishes at 1000 cells/ dish. After 3 weeks, the colonies were stained, photographed (FIG. 14B) or counted (FIG. 14C).

Figure 15:
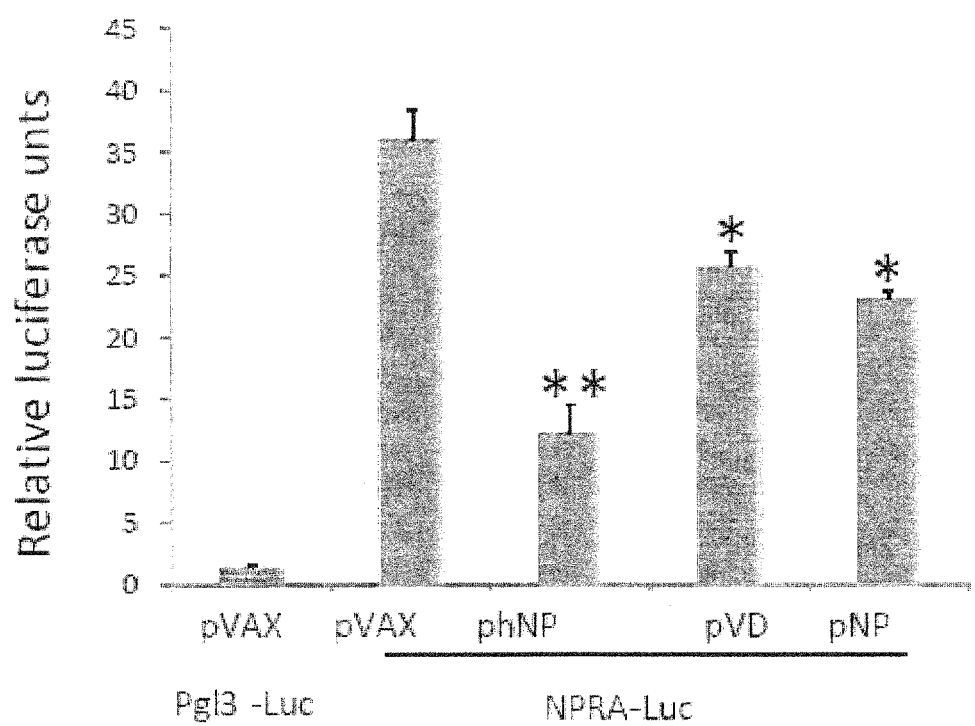

FIG. 15 shows that pNP$_{73-102}$ inhibits NPRA luciferase reporter activity. PC3 cells were co-transfected with pVAX, phNP73-102, pVD or pmNP73-102 and pNPRA-luc plasmid and pRenilla-luc plasmids. Forty-eight hrs after transfection, lysates were analysed for luciferase reporter activity. Relative luciferase activity ±SD is shown.

Figure 16:
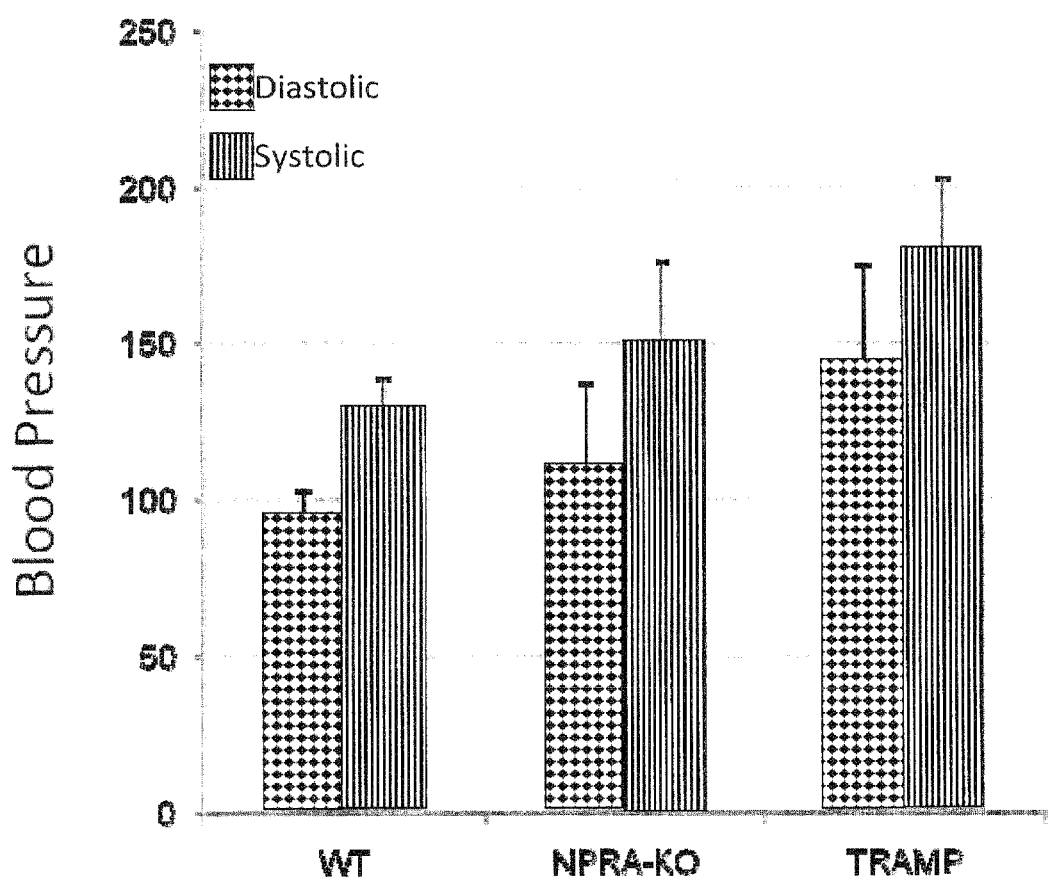

FIG. 16 shows results of blood pressure measurement in mice. Diastolic and systolic pressure of age matched wt (n=3), NPRA-KO (n=4) and TRAMP (n=4) male mice were measured using the CODA non-invasive blood pressure system (Kent Scientific). Data is presented as mean pressure ±SD.

Figure 17A:
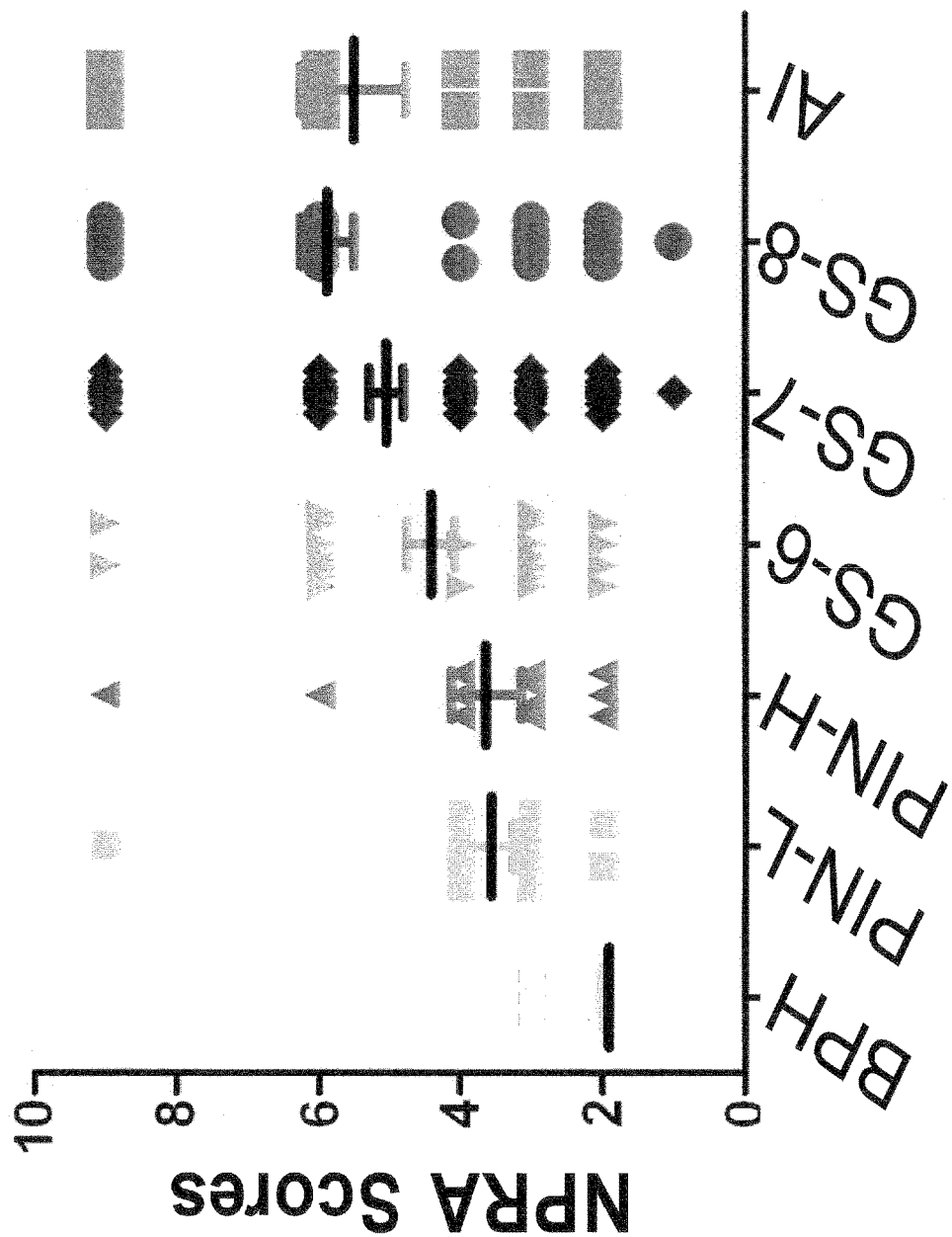
Figure 17B:
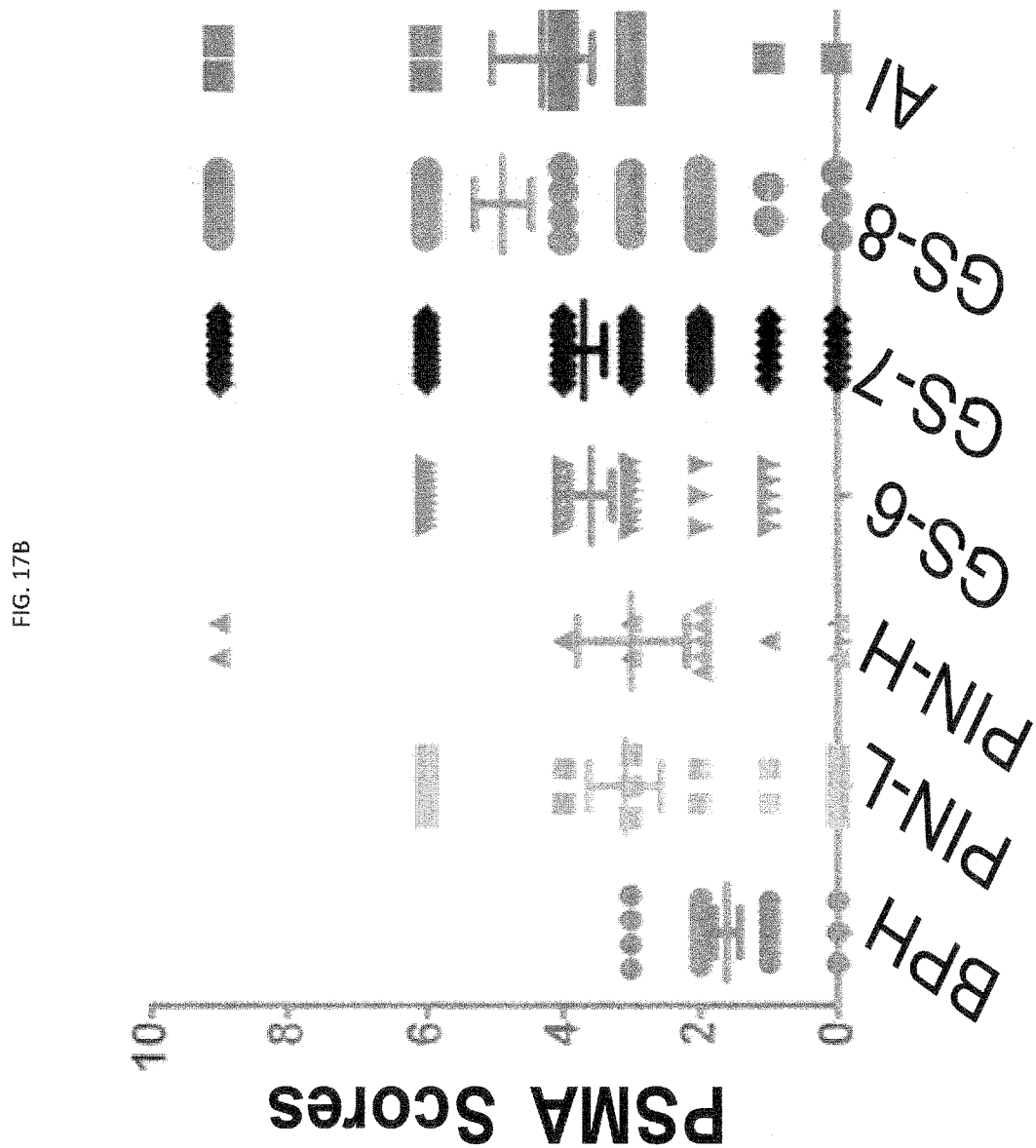
Figure 17C:
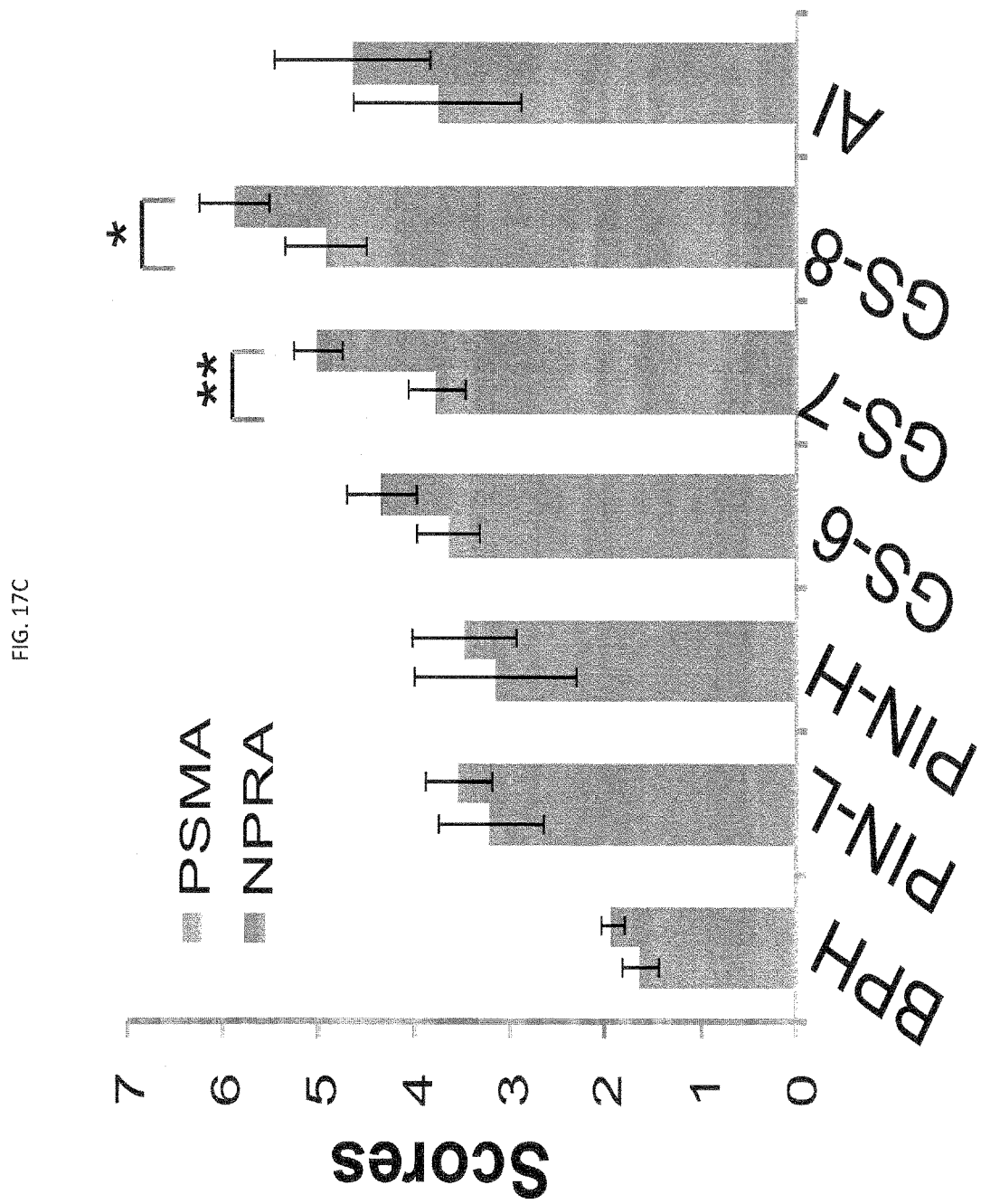

FIGS. 17A-C show results of examination of NPRA and prostate specific membrane antigen (PSMA) expressions using a human PCa (tissue microarray (TMA) containing 240 samples, including BPH (n=24), low grade prostatic intraepithelial neoplasm (PIN-L; n=21), high grade PIN (PIN-H; n=14), AI PCa (n=15) and prostate carcinoma (GS 6, n=33; GS 7, n=82; GS 8 to 10; n=51). TMA slide was stained for NPRA (FIG. 17AA) and PSMA (FIG. 17B) using a Ventana Discovery XT automated system. Slides were scored for intensity and cellularity. The distribution of scores in each disease stage of PCa is shown. The bar represents the mean sample score. FIG. 17C is graph comparing PSMA and NPRA scores at different PCA disease states.

BRIEF DESCRIPTION OF THE SEQUENCES

SEQ ID NO: 1 is the NPRA target sequence of antibody 1 (CWAEDPQERPPFQQIR).

SEQ ID NO: 2 is the NPRA target sequence of antibody 2 (CSELWRVRWEDLQPSSLERHLRS).

SEQ ID NO: 3 is the NPRA target sequence of antibody 3 (IHLSSETKAVLEEFDGFELELR); ID: 1010.

SEQ ID NO: 4 is the amino acid sequence of mouse NPRA protein.

SEQ ID NO: 5 is the amino acid sequence of human NPRA protein.

SEQ ID NO: 6 is a nucleic acid sequence encoding human NPRA protein.

DETAILED DISCLOSURE OF THE INVENTION

The methods of the invention are particularly applicable to the diagnosis and prognosis (staging, i.e., determining the stage) of malignancies (e.g., cancer), such as prostate cancer, colon cancer, breast cancer, pancreatic cancer Merkell cell carcinoma, and gastrointestinal stromal tumor (GIST). The sample on which the assay is performed is preferably of body tissue and/or body fluid from a subject, but may be isolated primary cells from a subject, or cells cultured in vitro (e.g., from a cell line). In some embodiments, the cells in the sample are obtained from a subject and not derived from a cell line. The sample may be a piece of tissue or a fine needle aspirate (FNA) of cells from a subject, for example. In some embodiments, the biological sample is a sample of cells or tissue suspected to be cancer, or a tumor. The subject may be presenting with symptoms of cancer at the time the sample is taken from the subject and/or NPRA expression determined, or the subject may be asymptomatic. In the methods of the invention, analysis of a sample for NPRA level or activity can carried out at the nucleic acid or protein level. Depending upon the sample and the method of analysis selected, analysis may involve isolation of the nucleic acid (DNA or RNA) or protein, and other preparatory steps.

NPRA cDNA may be detected by use of one or more labeled specific oligonucleotide probes, the probes being chosen so as to be capable of annealing to part of the amplified cDNA sequence. Alternatively, labeled oligonucleotide primers and/or labeled mononucleotides could be used. There are a number of suitable detectable labels, which can be employed, including radiolabels.

The level of gene expression of NPRA can be determined by RT-PCR, or by using labeled antibodies that bind to NPRA protein, or other methods known in the art for determination of messenger RNA or protein. For example, labeled antibodies that bind to NPRA (anti-NPRA antibodies) can be used to stain cells expressing the proteins. If the cells normally express the NPRA protein but the antibodies to NPRA do not bind to the cells as indicated by the lack of production of the desired stain or other label (or diminished stain or other label), or the antibodies bind to the cells to the same extent as normal control cells as indicated by the production of stain or other label, this indicates that NPRA is not expressed or not over-expressed by the sample cells and that the subject does not have cancer (a negative result). Conversely, if the antibodies to NPRA bind to the cells as indicated by the production of the desired stain or other label to a greater extent than normal control cells, this indicates that NPRA is over-expressed by the sample cells and that the subject has cancer (a positive result).

Detecting a Cancer

According to the present invention, a cancer can be detected by determining whether or not NPRA is expressed in a tissue type that may or may not normally express NPRA, and to what extent. There are a number of ways to determine this including the use of antibodies to detect the presence of the proteins or by determining the presence and amount mRNA coding for NPRA. Gene expression analysis can be performed at the mRNA or protein level to detect differences in NPRA gene expression between populations of target cells of a subject and reference cells (e.g., an appropriate control) to determine whether or not NPRA is being expressed and to what extent. NPRA expression can be determined in multiple samples taken at different time points to monitor NPRA expression.

The methods of detecting cancer of the invention are preferably performed using human biological samples. Samples may be obtained directly from a subject (e.g., by biopsy) or the subject's sample may be obtained from a third party. The target cell population may include one or more subpopulations of cells. Appropriate isolation steps may be taken, and/or pretreatments carried out, to determine NPRA expression in the target cell type or types. The samples may be preserved or pre-treated, or prepared for histological and immunohistochemical analysis. In the case of blood samples, red blood cells can by lysed by treatment with hypotonic solutions from nucleated cells, and separation can be achieved by differential centrifugation and other methods known in the art. For example, a Ficoll-step-gradient procedure can be utilized. PBMC-enriched cell populations can be obtained using the buffy coat method. Biological samples may be cryopreserved prior to determination of NPRA expression.

Prognosis of Cancer

Another aspect of the invention comprises a method for predicting progression of a malignancy (e.g., a tumor) and prognosing the malignancy, comprising: (a) obtaining a sample suspected of containing malignant cells; (b) analyzing the sample for NPRA level or activity; (c) correlating the level or activity with a control NPRA level or activity; and (d) correlating a high NPRA level or activity with an indication of unfavorable prognosis and a low NPRA level or activity with a favorable prognosis. In some embodiments, the method comprises a method for prognosing cancer in mammalian subjects, comprising: (a) obtaining a sample suspected of containing cancer cells; (b) analyzing the sample for NPRA level or activity; (c) correlating the NPRA level or activity with a control NPRA level of activity; and (d) correlating a high NPRA level or activity with an indication of unfavorable prognosis and a low NPRA level or activity with a favorable prognosis. In some embodiments, the analyzing in step (b) comprises preparing a cell extract. In some embodiments, the analyzing in step (b) is under conditions selected to detect any NPRA level or activity, and the method further comprises analyzing a second aliquot of the sample for NPRA level or activity under conditions selected to detect NPRA level or activity only above the control NPRA level or activity; and associating high NPRA level or activity to the presence of NPRA in both the first and second aliquots and low NPRA level or activity to the presence of NPRA only in the first aliquot. In some embodiments, the analyzing step further comprises amplifying any NPRA genetic material in the reaction mixture by a polymerase chain reaction using at least one primer complementary to a NPRA sequence. In some embodiments, the analyzing step comprises detecting NPRA protein using an immunological reagent such as a monoclonal or polyclonal antibody. In some embodiments, the sample comprises tumor cells from the subject. In some embodiments, the sample comprises tissue or cells adjacent to a tumor in the subject. Samples may be obtained directly from a subject (e.g., by biopsy) or the subject's sample may be obtained from a third party.

A favorable prognosis can be tumor regression, which may be indicative of longer survival rates relative to patients with unfavorable prognosis. Optionally, the favorable or unfavorable prognosis is communicated to the subject. The communication may be given on a tangible medium or communicated verbally or by other methods.

Another aspect of the invention includes a method for providing an NPRA expression profile useful for detecting and/or prognosing cancer. The method comprises analyzing a biological sample (e.g., sample that may or may not contain malignant cells) from a subject for NPRA level or activity, wherein an elevated NPRA level or activity (relative to a reference NPRA level or activity, such as a normal control or less aggressive stage of the malignancy) is indicative of the presence of a malignancy or a more advanced stage of the malignancy. Optionally, the method further comprises communicating the results of the analysis to a health care provider. For example, the communication may involve providing a report containing the results of the analysis to the health care provider. In some embodiments, the report is transmitted to the health care provider electronically (e.g., via the internet) or on a tangible medium (e.g., paper or tangible electronic storage medium).

Use of Immunological Reagents to Detect the Expression of NPRA

For the purposes of this invention, the term "immunological reagents" is intended to encompass antisera and antibodies, particularly monoclonal and polyclonal antibodies, as well as fragments thereof (including F(ab), $F(ab)_2$, F(ab)' and $F_v$ fragments) that bind to NPRA. Also included in the definition of immunological reagent are chimeric antibodies, humanized antibodies, and recombinantly-produced antibodies and fragments thereof, as well as aptamers (i.e., oligonucleotides capable of interacting with target molecules such as peptides). Immunological methods used in conjunction with the reagents of the invention include direct and indirect (for example, sandwich-type) labeling techniques, immunoaffinity columns, immunomagnetic beads, fluorescence activated cell sorting (FACS), enzyme-linked immunosorbent assays (ELISA), and radioimmune assay (RIA), most preferably FACS. For use in these assays, the immunological reagents can be labeled, using fluorescence, antigenic, radioisotopic or biotin labels, among others, or a labeled secondary or tertiary immunological detection reagent can be used to detect binding of the immunological reagents (e.g., in secondary antibody (sandwich) assays) used in determining the presence of NPRA. Examples of immunological reagents useful in the practice of this invention include antibodies, such as monoclonal antibodies that recognize NPRA. The immunological reagent may be specific to one or more isoforms of NPRA (e.g., one or more splice variants). Preferably, the immunological reagent is not specific with respect to NPRA isoform (i.e., binding to all NPRA isoforms, or at least the major NPRA isoforms). In some embodiments, the antibody detects (binds to) both human and mouse NPRA proteins or peptides.

The immunological reagents employed in the invention are preferably detectably-labeled, most preferably using fluorescent labels that have excitation and emission wavelengths adapted for detection using commercially-available instruments such as and most preferably fluorescence activated cell sorters. Examples of fluorescent labels useful in the practice of the invention include phycoerythrin (PE), fluorescein isothiocyanate (FITC), rhodamine (RH), Texas Red (TX), Cy3, Hoechst 33258, and 4',6-diamidino-2-phenylindole (DAPI). Such labels can be conjugated to immunological reagents, such as antibodies and most preferably monoclonal antibodies using standard techniques.

In addition to the use of immunological methods for detection and determination of NPRA protein (e.g., ELISA, Western blots, immunoprecipitation), other detection methods for proteins that can be utilized to determine NPRA expression include, but are not limited to, mass spectrometry, protein array, and 2-D gel electrophoresis. For example, surface-enhanced laser desorption/ionization time-of-flight mass spectrometry (SELDI-TOF MS) allows rapid generation of high-throughput protein profiles from a large number of samples (see, for example, Liu et al., *Cancer Invest.* 2006, 24:747-753; Munro et al., *Int. J. Cancer.* 2006, 119:2642-2650; Simpkins et al., *Pharmacogenomics.* 2005, 6(6):647-653; Oh et al., *Genome Inform.* 2005, 16:195-204; Lakhan S. E., *Diagn Pathol.* 2006, 1:11; Novikova et al., *Neurobiol Dis.* 2006, 23:61-76; Lewczuk et al., *Biol Psychiatry.* 2004, 55:524-530; and Sanchez et al., *Proteomics.* 2004, 4:2229-2233, which are each incorporated herein by reference in its entirety).

SEQ ID NO:4 is the amino acid sequence of mouse NPRA protein:

```
mprsrrvrpr lrallllppl lllrsghasd ltvavvlpvt ntsypwswar vgpavelalg
rvkarpdllp gwtvrmvlgs senaagvcsd taaplaavdl kwehspavfl gpgcvysaap
vdrftahwrl plltagapal gigvkdeyal ttrtgpshvk lgdfvtalhr rlgwehqalv
lyadrlgddr pcffivegly mrvrerinit vnhqefvegd pdhytkllrt vqrkgrviyi
csspdafrnl mllaldaglt gedyvffhld vfgqslqgaq gpvpekpwer ddgqdrrarq
rfqaakiity kepdnpeyle flkqlkllad kkfnftmedg lkniipasfh dglllyvqav
tetlaqggtv tdgenitqrm wnrsfqgvtg ylkidrngdr dtdsplwdmd petgafrvvl
nfngtsqelm aysehrlywp lgypppdipk cgfdnedpac nqdhfstlev lalvgslslv
sflivsffiy rkmqlekelv selwrvrwed lqpsslerhl rsagsrltls grgsnygsll
ttegqfqvfa ktayykgnlv avkrvnrkri eltrkvlfel khmrdvqneq ltrfvgactd
ppniciltey cprgslqdil enesitldwm frysltndiv kgmlflhnga icshgnlkss
ncvvdgrfvl kitdyglesf rdpepeqght lfakklwtap ellrmasppa rgsqagdvys
fgiilqeial rsgvfyvegl dlspkeiier vtrgeqppfr psmdlqshle elgqlmqrcw
aedpqerppf qqirlalrkf nkenssnild nllsrmeqya nnleelveer tqpyleekrk
aeallyqilp hsvaeqlkrg etvqaeafds vtiyfsdivg ftalsaestp mqvvtllndl
ytcfdavidn fdvykvetig daymvvsglp vrngqlhare varmalalld avrsfrighr
pqeqlrlrig ihtgpvcagv vglkmprycl fgdtvntasr mesngealri hlssetkavl
eefdgfelel rgdvemkgkg kvrsywllgd rgcssra
```

(GenBank Accession Number AAA37670; version AAA37670.1, GI: 309246; which is incorporated herein by reference)

SEQ ID NO:5 is the amino acid sequence of human NPRA protein:

```
mfrysltndi vkgmlflhng aicshgnlks sncvvdgrfv lkitdygles frdldpeqgh
tvyakklwta pellrmaspp vrgsqagdvy sfgiilqeia lrsgvfhveg ldlspkeiie
rvtrgeqppf rpslalqshl eelgllmqrc waedpqerpp fqqirltlrk fnrenssnil
dnllsrmeqy annleelvee rtqayleekr kaeallyqil phsvaeqlkr getvqaeafd
svtiyfsdiv gftalsaest pmqvvtllnd lytcfdavid nfdvykveti gdaymvvsgl
pvrngrlhac evarmalall davrsfrirh rpqeqlrlri gihtgpvcag vvglkmpryc
lfgdtvntas rmesngealk ihlssetkav leefggfele lrgdvemkgk gkvrt
```

(GenBank Accession Number AAD14112; version AAD14112.1, GI: 4261812; which is incorporated herein by reference)
Other versions of the human mouse NPRA protein sequences include:
GenBank Accession Number AAF01340 (version AAF01340.1, GI: 6013455);
GenBank Accession Number CAI3613 (version CAI13613.1, GI: 55962127);
GenBank Accession Number AAI10660 (version AAI10660.1, GI: 83404966); and
GenBank Accession Number AAA66945 (version AAA66945, GI: 473634), which are each incorporated herein by reference.

Detection of NPRA Using Nucleic Acid Hybridization Techniques

The expression of NPRA can be determined using nucleic acids and associated hybridization methods to detect the presence of mRNA within a cell of interest. For example, a nucleic acid that is complementary to and hybridizes under stringent conditions to the mRNA of a portion of NPRA can be detectably labeled. Such a detectably labeled nucleic acid molecule can be contacted with a cell or an extract of a cell to detect the presence and amount of the mRNA that encodes NPRA. The amount of nucleic acids that encode NPRA is assumed to correlate with the expression of the NPRA in a cell. The selection of an appropriate nucleic acid molecule for use as a probe can be made by studying the nucleic acid sequences of human NPRA and determining an appropriate length. A unique sequence should be determined that selectively hybridizes under stringent conditions to the mRNA of NPRA. The probe may be specific to one or more isoforms of NPRA. Preferably, the probe is not specific with respect to NPRA isoform (i.e., detecting all NPRA isoforms, or at least the major NPRA isoforms).

The term "stringent conditions" as used herein refers to parameters with which the art is familiar. Nucleic acid hybridization parameters may be found in references which compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. More specifically, stringent conditions, as used herein, refers, for example, to hybridization at 65 degrees C. in hybridization buffer (3.5×SSC, 0.02% Ficoll, 0.02% polyvinyl pyrrolidone, 0.02% Bovine Serum Albumin, 2.5 mM $NaH_2 PO_4$ (pH7), 0.5% SDS, 2 mM EDTA). SSC is 0.15 M sodium chloride/0.015 M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1×SDS at temperatures up to 68 degrees C.

There are other conditions, reagents, and so forth which can be used, which result in a similar degree of stringency. The skilled artisan will be familiar with such conditions, and thus they are not provided here. It will be understood, however, that the skilled artisan will be able to manipulate the conditions in a manner to permit the clear identification of NPRA (e.g., by using lower stringency conditions). The skilled artisan also is familiar with the methodology for screening cells and libraries for expression of such molecules which then are routinely isolated, followed by isolation of the pertinent nucleic acid molecule and sequencing.

One method for detecting the NPRA transcripts in genetic material derived from a subject's cells uses polymerase chain reaction (PCR) technology. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990). Applications of PCR technology are disclosed in "Polymerase Chain Reaction" Erlich, H. A., et al., Eds. Cold Spring Harbor Press, Cold Spring Harbor, N.Y. (1989). U.S. Pat. No. 4,683,202, U.S. Pat. No. 4,683,195, U.S. Pat. No. 4,965,188 and U.S. Pat. No. 5,075,216 describe methods of performing PCR. PCR may be routinely practiced using Perkin Elmer Cetus GENE AMP RNA PCR kit.

PCR technology allows for the rapid generation of multiple copies of DNA sequences by providing 5' and 3' primers that hybridize to sequences present in an RNA or DNA molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the same small fragment of nucleic acid, exponential amplification of a specific double-stranded size product results. If only a single primer hybridizes to the nucleic acid fragment, linear amplification produces single-stranded products of variable length.

PCR primers can be designed routinely by those having ordinary skill in the art using sequence information. The nucleotide sequences of NPRA transcripts are known in the art. To perform this method, RNA is extracted from cells in a sample and tested or used to make cDNA using well known methods and readily available starting materials.

Those having ordinary skill in the art can readily prepare PCR primers. A set of primers generally contains two primers. When performing PCR on extracted mRNA or cDNA generated therefrom, if the NPRA transcript or cDNA generated therefrom is present, multiple copies of the mRNA or cDNA will be made. If it is not present, PCR will not generate a discrete detectable product. Primers are generally 8-50 nucleotides, preferably about 15-35 nucleotides, more preferably 18-28 nucleotides, which are identical or complementary to and therefor hybridize to the NPRA transcript or cDNA generated therefrom. In preferred embodiments, the primers are each 15-35 nucleotides in length, and more preferably 18-28 nucleotides in length. The primer must hybridize to the sequence to be amplified.

Typical primers are 18-28 nucleotides in length and generally have 500 to 60% G+C composition. The entire primer is preferably complementary to the sequence to which it must hybridize. Preferably, primers generate PCR products 100 base pairs to 2000 base pairs. However, it is possible to generate products of 50 to up to 10 kb and more. If mRNA is used as a template, the primers must hybridize to mRNA sequences. If cDNA is used as a template, the primers must hybridize to cDNA sequences.

The mRNA or cDNA is combined with the primers, free nucleotides and enzyme following standard PCR protocols. The mixture undergoes a series of temperature changes. If the NPRA transcript or cDNA generated therefrom is present, that is, if both primers hybridize to sequences on the same molecule, the molecule comprising the primers and the intervening complementary sequences will be exponentially amplified. The amplified DNA can be easily detected by a variety of well known means. If no NPRA transcript or cDNA generated therefrom is present, no PCR product will be exponentially amplified. The PCR technology therefore provides an extremely easy, straightforward and reliable method of detecting the NPRA transcript in a sample.

PCR product may be detected by several well known means. The preferred method for detecting the presence of amplified DNA is to separate the PCR reaction material by gel electrophoresis and stain the gel with ethidium bromide in order to visual the amplified DNA if present. A size standard of the expected size of the amplified DNA is preferably run on the gel as a control.

In some instances, such as when unusually small amounts of RNA are recovered and only small amounts of cDNA are generated therefrom, it is desirable to perform a PCR reaction on the first PCR reaction product. That is, if difficult to detect quantities of amplified DNA are produced by the first reaction, a second PCR can be performed to make multiple copies of DNA sequences of the first amplified DNA. A nested set of primers are used in the second PCR reaction. The nested set of primers hybridize to sequences downstream of the 5' primer and upstream of the 3' primer used in the first reaction.

SEQ ID NO:6 is a nucleic acid sequence encoding human NPRA.

```
acactccctg gggcaggcgc tcacgcacgc tacaaacaca cactcctctt tcctccctcg
cgcgccctct ctcatccttc ttcacgaagc gctcactcgc accctttctc tctctctctc
tctctctcta acacgcacgc acactcccag ttgttcacac tcgggtcctc tccagcccga
cgttctcctg gcacccacct gctccgcggc gccctgcgcg cccccctcgg tcgcgcccct
tgcgctctcg gcccagaccg tcgcagctac aggggcctc gagcccggg gtgagcgtcc
ccgtcccgct cctgctcctt cccataggga cgcgcctgat gcctgggacc ggccgctgag
cccaagggga ccgaggaggc catggtagga gcgctcgcct gctgcggtgc ccgctgaggc
catgccgggg ccccggcgcc ccgctggctc ccgcctgcgc ctgctcctgc tcctgctgct
gccgccgctg ctgctgctgc tccggggcag ccacgcgggc aacctgacgg tagccgtggt
actgccgctg gccaatacct cgtaccctg gtcgtgggcg cgcgtgggac ccgccgtgga
gctggccctg gcccaggtga aggcgcgccc cgacttgctg ccgggctgga cggtccgcac
ggtgctgggc agcagcgaaa acgcgctggg cgtctgctcc gacaccgcag cgcccctggc
cgcggtggac ctcaagtggg agcacaaccc cgctgtgttc ctgggccccg gctgcgtgta
cgccgccgcc ccagtggggc gcttcaccgc gcactggcgg gtcccgctgc tgaccgccgg
cgccccggcg ctgggcttcg gtgtcaagga cgagtatgcg ctgaccaccc gcgcggggcc
cagctacgcc aagctggggg acttcgtggc ggcgctgcac cgacggctgg gctgggagcg
ccaagcgctc atgctctacg cctaccggcc gggtgacgaa gagcactgct tcttcctcgt
ggagggctg ttcatgcggg tccgcgaccg cctcaatatt acggtggacc acctggagtt
cgccgaggac gacctcagcc actacaccag gctgctgcgg accatgccgc gcaaaggccg
agttatctac atctgcagct ccctgatgc cttcagaacc ctcatgctcc tggccctgga
agctggcttg tgtggggagg actacgtttt cttccacctg gatatctttg ggcaaagcct
gcaaggtgga cagggccctg ctccccgcag gccctgggag agaggggatg ggcaggatgt
cagtgcccgc caggcctttc aggctgccaa aatcattaca tataaagacc cagataatcc
cgagtacttg gaattcctga agcagttaaa acacctggcc tatgagcagt tcaacttcac
catggaggat ggcctggtga acaccatccc agcatccttc cacgacgggc tcctgctcta
tatccaggca gtgacggaga ctctggcaca tgggggaact gttactgatg gggagaacat
cactcagcgg atgtggaacc gaagctttca aggtgtgaca ggatacctga aaattgatag
cagtggcgat cgggaaacag acttctccct ctgggatatg gatccccgaga atggtgcctt
cagggttgta ctgaactaca atgggacttc ccaagagctg gtggctgtgt cggggcgcaa
actgaactgg cccctggggt accctcctcc tgacatcccc aaatgtggct ttgacaacga
agacccagca tgcaaccaag atcacctttc caccctggag gtgctggctt tggtgggcag
cctctccttg ctcggcattc tgattgtctc cttcttcata tacaggaaga tgcagctgga
gaaggaactg gcctcggagc tgtggcgggt gcgctgggag gacgttgagc ccagtagcct
tgagaggcac ctgcggagtg caggcagccg gctgaccctg agcgggagag gctccaatta
cggctccctg ctaaccacag agggccagtt ccaagtcttt gccaagacag catattataa
```

```
-continued
gggcaacctc gtggctgtga aacgtgtgaa ccgtaaacgc attgagctga cacgaaaagt cctgttttgaa ctgaagcata tgcgggatgt gcagaatgaa cacctgacca ggtttgtggg agcctgcacc gaccccccca atatctgcat cctcacagag tactgtcccc gtgggagcct gcaggacatt ctggagaatg agagcatcac cctggactgg atgttccggt actcactcac caatgacatc gtcaagggca tgctgtttct acacaatggg gctatctgtt cccatgggaa cctcaagtca tccaactgcg tggtagatgg gcgctttgtg ctcaagatca ccgactatgg gctggagagc ttcagggacc tggacccaga gcaaggacac accgtttatg ccaaaaagct gtggacggcc cctgagctcc tgcgaatggc ttcacccct gtgcggggct cccaggctgg tgacgtatac agctttggga tcatccttca ggagattgcc ctgaggagtg gggtcttcca cgtggaaggt ttggacctga gccccaaaga gatcatcgag cgggtgactc ggggtgagca gcccccttc cggccctccc tggccctgca gagtcacctg gaggagttgg ggctgctcat gcagcggtgc tgggctgagg acccacagga gaggccacca ttccagcaga tccgcctgac gttgcgcaaa tttaacaggg agaacagcag caacatcctg gacaacctgc tgtcccgcat ggagcagtac gcgaacaatc tggaggaact ggtggaggag cggacccagg catacctgga ggagaagcgc aaggctgagg ccctgctcta ccagatcctg cctcactcag tggctgagca gctgaagcgt ggggagacgg tgcaggccga agcctttgac agtgttacca tctacttcag tgacattgtg ggtttcacag cgctgtcggc ggagagcaca cccatgcagg tggtgaccct gctcaatgac ctgtacactt gctttgatgc tgtcatagac aactttgatg tgtacaaggt ggagacaatt ggcgatgcct acatggtggt gtcagggctc cctgtgcgga acgggcggct acacgcctgc gaggtagccc gcatggccct ggcactgctg gatgctgtgc gctccttccg aatccgccac cggccccagg agcagctgcg cttgcgcatt ggcatccaca caggacctgt gtgtgctgga gtggtgggac tgaagatgcc ccgctactgt ctctttgggg atacagtcaa cacagcctca agaatggagt ctaatgggga agccctgaag atccacttgt cttctgagac caaggctgtc ctggaggagt ttggtggttt cgagctggag cttcgagggg atgtagaaat gaagggcaaa ggcaaggttc ggacctactg gctccttggg gagagggga gtagcacccg aggctgacct gcctcctctc ctatccctcc acacctccct accctgtgcc agaagcaaca gaggtgccag gcctcagcct cacccacagc agcccatcg ccaaaggatg gaagtaattt gaatagctca ggtgtgctga ccccagtgaa gacaccagat aggacctctg agaggggact ggcatggggg gatctcagag cttacaggct gagccaagcc cacggccatg cacagggaca ctcacacagg cacacgcacc tgctctccac ctggactcag gccgggctgg gctgtggatt cctgatcccc tcccctcccc atgctctcct ccctcagcct tgctaccctg tgacttactg ggaggagaaa gagtcacctg aaggggaaca tgaaaagaga ctaggtgaag agagggcagg ggagcccaca tctggggctg gcccacaata cctgctcccc cgacccctc cacccagcag tagacacagt gcacagggga gaagagggt ggcgcagaag ggttgggggc ctgtatgcct tgcttctacc atgagcagag acaattaaaa tctttattcc agtgaaaaaa aaaaaaaaa a
```

(GenBank Accession Number NM_000906; Version NM_000906.3, GI: 67830410, which is incorporated herein by reference)

The present invention includes diagnostic kits comprising oligonucleotides which are useful as primers for performing PCR methods to amplify the NPRA transcript or cDNA generated therefrom.

According to the invention, diagnostic kits can be assembled which are useful to practice methods of detecting the presence of the NPRA transcript or cDNA generated therefrom in biological samples. Such diagnostic kits comprise oligonucleotides which are useful as primers for performing PCR methods. It is preferred that diagnostic kits according to the present invention comprise a container comprising a size marker to be run as a standard on a gel used to detect the presence of amplified DNA. The size marker is the same size as the DNA generated by the primers in the presence of the NPRA transcript or cDNA generated therefrom. Additional components in some kits include instructions for carrying out the assay. Additionally, the kit may optionally comprise depictions or photographs that represent the appearance of positive and negative results.

PCR assays are useful for detecting the NPRA transcript in homogenized tissue samples and cells in body fluid samples, such as blood.

Another method of determining whether a sample contains cells expressing NPRA is by branched chain oligonucleotide hybridization analysis of mRNA extracted from a sample. Branched chain oligonucleotide hybridization may be performed as described in U.S. Pat. No. 5,597,909, U.S. Pat. No. 5,437,977 and U.S. Pat. No. 5,430,138, which are each incorporated herein by reference. Reagents may be designed following the teachings of those patents and that sequence of the NPRA transcript.

Another method of determining whether a sample contains cells expressing NPRA is by Northern Blot analysis of mRNA extracted from a biological sample, such as blood. The techniques for performing Northern blot analyses are well known by those having ordinary skill in the art and are described in Sambrook, J. et al., (1989) Molecular Cloning: A Laboratory Manual, Cold Spring Harbor Laboratory Press, Cold Spring Harbor, N.Y. mRNA extraction, electrophoretic separation of the mRNA, blotting, probe preparation and hybridization are all well known techniques that can be routinely performed using readily available starting material.

The mRNA is extracted using poly dT columns and the material is separated by electrophoresis and, for example, transferred to nitrocellulose paper. Labeled probes made from an isolated specific fragment or fragments can be used to visualize the presence of a complementary fragment fixed to the paper. Probes useful to identify mRNA in a Northern Blot have a nucleotide sequence that is complementary to one or more sequences of the NPRA transcript. Those having ordinary skill in the art can use the sequence information included herein to design such probes or to isolate and clone the NPRA transcript or cDNA generated therefrom to be used as a probe. Such probes are at generally least 15 nucleotides, preferably 30-200, more preferably 40-100 nucleotide fragments and may be the entire NPRA transcript.

According to the invention, diagnostic kits can be assembled, which are useful to practice methods of detecting the presence of the NPRA transcript in biological samples by Northern blot analysis. Such diagnostic kits comprise oligonucleotides which are useful as probes for hybridizing to the mRNA. The probes may be radiolabeled. It is preferred that diagnostic kits according to the present invention comprise a container comprising a size marker to be run as a standard on a gel. It is preferred that diagnostic kits according to the present invention comprise a container comprising a positive control which will hybridize to the probe. Additional components in some kits include instructions for carrying out the assay (e.g., written or embossed on packaging or on one or more containers). Additionally, the kit may optionally comprise depictions or photographs that represent the appearance of positive and negative results. Northern blot analysis is useful for detecting the NPRA transcript in tissue samples and cells in body fluid samples.

Another method of detecting the presence of the NPRA transcript is by oligonucleotide hybridization technology. Oligonucleotide hybridization technology is well known to those having ordinary skill in the art. Briefly, detectable probes which contain a specific nucleotide sequence that will hybridize to nucleotide sequence of the NPRA transcript. RNA or cDNA made from RNA from a sample is fixed, usually to filter paper or the like. The probes are added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicate complementary sequences.

Probes useful in oligonucleotide assays at least 18 nucleotides of complementary DNA and may be as large as a complete complementary sequence to the NPRA transcript. In some preferred embodiments, the probes of the invention are 30-200 nucleotides, preferably 40-100 nucleotides.

One having ordinary skill in the art, using the human NPRA sequence information disclosed herein can design probes which are fully complementary to at least a portion of the NPRA transcript. Hybridization conditions can be routinely optimized to minimize background signal by non-fully complementary hybridization. In some preferred embodiments, the probes are full length clones. Probes are at least 15 nucleotides, preferably 30-200, more preferably 40-100 nucleotide fragments and may be the entire NPRA transcript.

The present invention includes labeled oligonucleotides which are useful as probes for performing oligonucleotide hybridization. That is, the binding portion of the probe can be fully complementary with the NPRA transcript. For example, the mRNA sequence includes portions encoded by different exons. The labeled probes of the present invention are labeled with radiolabeled nucleotides or are otherwise detectable by readily available nonradioactive detection systems.

According to the invention, diagnostic kits can be assembled which are useful to practice oligonucleotide hybridization methods of the invention. Such diagnostic kits comprise a labeled oligonucleotide which encodes portions of the NPRA transcript. It is preferred that labeled probes of the oligonucleotide diagnostic kits according to the present invention are labeled with a radionucleotide. The oligonucleotide hybridization-based diagnostic kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample. Additional components in some kits include instructions for carrying out the assay. Additionally the kit may optionally comprise depictions or photographs that represent the appearance of positive and negative results. Oligonucleotide hybridization techniques are useful for detecting the NPRA transcript in tissue samples (e.g., tissue homogenates) and cells in body fluid samples.

Thus, the present invention relates to in vitro kits for evaluating biological samples to determine the level of NPRA (e.g., NPRA cDNA, NPRA mRNA, NPRA protein, NPRA activity) and to reagents and compositions useful to practice the same. Techniques for determining the presence of mRNA of a polypeptide have resulted in the production of various microarrays, bioarray, biochips and biochip arrays, which may be employed with the invention. As used herein, the terms "microarray," "bioarray," "biochip" and "biochip array" refer to an ordered spatial arrangement of immobilized biomolecular probes arrayed on a solid supporting substrate. Preferably, the biomolecular probes are immobilized on second linker moieties in contact with polymeric beads, wherein the polymeric beads are immobilized on first linker moieties in contact with the solid supporting substrate. Biochips, as used in the art, encompass substrates containing arrays or microarrays, preferably ordered arrays and most preferably ordered, addressable arrays, of biological molecules that comprise one member of a biological binding pair. Typically, such arrays are oligonucleotide arrays comprising a nucleotide sequence that is complementary to at least one sequence of a nucleic acid that encodes NPRA. Alternatively, and preferably, proteins, peptides or other small molecules can be arrayed in such biochips for performing, inter alia, immunological analyses (wherein the arrayed molecules are antigens) or assaying biological receptors (wherein the arrayed molecules are ligands, agonists or antagonists of said receptors). Useful microarrays for detecting differential gene expression are described, for example, in U.S. Pat. No. 6,040,138 to Lockhart et al. (commercially-available from Affymetrix, Inc., Santa Clara, Calif.) and U.S. Pat. No. 6,004,755 to Wang (commercially-available from Incyte Inc., Palo Alto, Calif.) and are also commercially available, inter alia, from Research Genetics (Huntsville, Ala.).

Gene expression analysis can be performed to detect differences in gene expression between populations of target cells of a subject and reference cells (e.g., an appropriate control) to determine whether or not NPRA is being expressed and/or to what extent. The target cell population may include one or more subpopulations of cell types. Hybridization of gene expression microarrays can be used to produce patterns of gene expression of NPRA. Identification of genes and patterns of genes differentially expressed in the target cells is established by comparison of the gene expression pattern obtained by performing the microarray hybridization analysis on cDNA from target cells in comparison to that of normal cells.

In the methods of the invention, elevated NPRA level or activity can be used to diagnose or provide prognosis (predict progression of) a malignancy (e.g., cancer). Methods for determining NPRA activity are known in the art (Patel J. B. et al., *Am. J. Physiol. Heart Circ. Physiol.*, 2005, 289:H777-H784, which is incorporated herein by reference).

In some embodiments, various methodologies of the instant invention include a step that involves comparing NPRA level or activity in a sample obtained from a subject to a "suitable control," also referred to interchangeably herein as an "appropriate control." Thus, in accordance with the invention, it can be determined whether a subject has, or more likely to have, a cancer, based on NPRA expression in relevant cells from the subject (e.g., based on comparison to an appropriate control). A "suitable control" or "appropriate control" in this context is a predetermined value associated with NPRA useful for comparison purposes, which can take many different forms. Exemplary forms include, but are not limited to, for example, a transcription rate, mRNA level, translation rate, protein level, protein structure, biological activity, cellular characteristic or property, genotype, phenotype, receptor activity etc. associated with NPRA. In one embodiment, a "suitable control" is a predetermined NPRA activity, which is compared to NPRA activity in a sample obtained from a subject being identified as having or not having a cancer associated with (correlating with) NPRA over-expression as described herein. In another embodiment, a "suitable control" is a predetermined NPRA level, which is compared to an NPRA level in a sample obtained from a subject being identified as having or not having a cancer associated with (correlating with) NPRA over-expression as described herein. In another embodiment, a "suitable control" is a predetermined NPRA level, which is compared to an NPRA level in a sample derived from a subject in which a clinical measure was achieved, for example an NPRA level obtained from cells in a subject who reached, or failed to reach, a particular clinical outcome following treatment of the cancer.

In some embodiments, a "suitable control" or an "appropriate control" can be a single cut-off value, such as a median or mean. A single cut-off value can be established, for example, based upon comparative groups, such as in groups having an NPRA level or activity which correlates with lack of, or resistance to, a cancer, and groups having an NPRA level or activity which does not confer or correlate with resistance to lack of, or resistance to, a cancer. For example, samples can be obtained from various individuals or blood or tissue banks and an NPRA level or activity can be measured in each sample. Consequently, a single cut-off value can be based on the mean of an NPRA level or activity in samples which correlate with lack of, or resistance to, a cancer. Another comparative group can be, for example, an NPRA level or activity in a group of individuals with a family history of a cancer, or a family history with a lack of, resistance to, a cancer. Optionally, the determined NPRA can be compared to a control in which the control is an NPRA level or activity from a subject, or a mean NPRA level or activity from a group of subjects, known to have one or more cancers. In practice, the readout or output for determination of NPRA may be qualitative, quantitative, or semi-quantitative. Preferably, a quantitative value of NPRA level or activity is determined, which is compared to that of an appropriate control.

The terms "subject," "individual," and "patient", as used herein, refers to a human or non-human mammal, of any age or gender.

As used herein, the terms "treat," "treating," and "treatment" refer to both therapeutic treatment and prophylactic or preventative measures, wherein the object is to prevent or slow down (lessen) an undesired physiological change or disorder, such as the development or spread of cancer, in a subject. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. In some embodiments, the treatment includes one disclosed in U.S. Patent Publication Nos. 2009/0176706 (Mohapatra); 2008/0214437 (Mohapatra et al.); 2007/0265204 (Mohapatra et al.); and 20050272650 (Mohapatra), which are each incorporated herein by reference.

As used herein, the terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include, but are no limited to, breast cancer, prostate cancer, colon cancer, squamous cell cancer, small-cell lung cancer, non-small cell lung cancer, gastrointestinal cancer, pancreatic cancer, cervical cancer, ovarian cancer, liver cancer, e.g., hepatic carcinoma, bladder cancer, colorectal cancer, endometrial carcinoma, kidney cancer, and thyroid cancer. The terms "cancer" and "malignancy" are used interchangeably herein.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; GIST, intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); pancreatic cancer; retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas. In some embodiments of the invention, the cancer is not ovarian cancer or melanoma.

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site.

As used in this specification, including the appended claims, the singular "a", "an", and "the" include plural reference unless the contact dictates otherwise. Thus, for example, a reference to "an antibody" includes more than one such antibody. A reference to "a cell" includes more than one such cell, and so forth.

The terms "comprising", "consisting of" and "consisting essentially of" are defined according to their standard meaning. The terms may be substituted for one another throughout the instant application in order to attach the specific meaning associated with each term.

Without wishing to be bound by theory, it is contemplated that any suitable characteristic associated with NPRA such as, for example, mRNA level, polypeptide amount, NPRA activity, transcription rate, translation rate etc., may be used as an indicator for identifying subjects that are suffering from a cancer, and for prognosing cancer. In some embodiments, NPRA activity or level, for example, the amount of NPRA polypeptide present, is used as an indicator for identifying subjects suitable for a further diagnostic test for cancer. In other embodiments, NPRA level or activity is used as an indicator for identifying subjects suitable for treatment of a cancer.

EXEMPLIFIED EMBODIMENTS

Embodiment 1

A method of detecting a malignancy in a mammalian subject, comprising obtaining a sample comprising cells from the subject, and determining whether the level or activity of natriuretic peptide receptor A (NPRA) is elevated in the cells, wherein elevated NPRA level or activity is indicative of a malignancy.

Embodiment 2

The method of embodiment 1, wherein the malignancy is a cancer selected from the group consisting of prostate cancer, colon cancer, breast cancer, pancreatic cancer, Merkell cell carcinoma, and gastrointestinal stromal tumor (GIST).

Embodiment 3

The method of embodiment 1, wherein the malignancy is not ovarian cancer or melanoma.

Embodiment 4

The method of embodiment 1, further comprising carrying out one or more confirmatory tests for the malignancy if the level or activity NPRA is elevated.

Embodiment 5

The method of any preceding embodiment, wherein the sample is a tissue sample.

Embodiment 6

The method of any preceding embodiment, wherein the sample comprises tissue or cells that is adjacent a tumor in the subject.

Embodiment 7

The method of any preceding embodiment, wherein the sample comprises tumor cells.

Embodiment 8

The method of any preceding embodiment, further comprising advising the subject of treatment options for treating the malignancy if the level or activity of NPRA is elevated.

Embodiment 9

A method of treating a malignancy in a mammalian subject, comprising obtaining a sample comprising cells from the subject, determining whether the level or activity of natriuretic peptide receptor A (NPRA) is elevated in the cells, wherein elevated NPRA level or activity is indicative of a malignancy, and treating the subject with a therapy for the malignancy if the NPRA level or activity is elevated.

Embodiment 10

The method of embodiment 9, wherein the malignancy is selected from the group consisting of prostate cancer, colon cancer, breast cancer, pancreatic cancer, Merkell cell carcinoma, and GIST.

Embodiment 11

The method of embodiment 9 or 10, further comprising carrying out one or more confirmatory tests for the malignancy if the NPRA level or activity is elevated.

Embodiment 12

The method of any of one of embodiments 9 to 11, wherein the therapy comprises surgery, chemotherapy, radiation therapy, or a combination of two or more of the foregoing.

Embodiment 13

The method of any one of embodiments 9 to 12, wherein the sample is a tissue sample.

Embodiment 14

The method of any of one of embodiments 9 to 13, wherein the sample is a tumor cells.

Embodiment 15

The method of any one of embodiments 9 to 14, wherein the sample comprises tissue or cells that is adjacent a tumor in the subject.

Embodiment 16

A method of determining the level or activity of natriuretic peptide receptor A (NPRA) in cancer cells of a mammalian subject, comprising obtaining a sample of cancer cells from the subject, and determining the level or activity of NPRA in the cells.

Embodiment 17

The method of embodiment 16, wherein the cancer cells are selected from the group consisting of prostate cancer, colon cancer, breast cancer, pancreatic cancer, Merkell cell carcinoma, and GIST.

Embodiment 18

An in vitro polymerase chain reaction (PCR) assay kit for determining whether a subject has a malignancy by detecting elevated level or activity of natriuretic peptide receptor A (NPRA), said kit comprising a first container comprising polymerase chain reaction (PCR) primers that amplify an NPRA transcript or cDNA generated therefrom; and a second container comprising a nucleic acid marker, said marker being and labeled and able to hybridize to said transcript or cDNA.

Embodiment 19

A method for predicting progression of a malignancy and prognosing the malignancy in a mammalian subject, comprising: (a) obtaining a sample suspected of containing malignant cells; (b) analyzing the sample for NPRA level or activity; (c) correlating the level or activity with a control NPRA level or activity; and (d) correlating a high NPRA level or activity with an indication of unfavorable prognosis and a low NPRA level or activity with a favorable prognosis.

Embodiment 20

A method for prognosing cancer in mammalian subjects, comprising: (a) obtaining a sample suspected of containing cancer cells; (b) analyzing the sample for NPRA level or activity; (c) correlating the NPRA level or activity with a control NPRA level of activity; and (d) correlating a high NPRA level or activity with an indication of unfavorable prognosis and a low NPRA level or activity with a favorable prognosis.

Embodiment 21

The method of embodiment 20, wherein the analyzing in step (b) comprises preparing a cell extract.

Embodiment 22

The method of embodiment 20, wherein the analyzing in step (b) is under conditions selected to detect any NPRA level or activity, and the method further comprises analyzing a second aliquot of the sample for NPRA level or activity under conditions selected to detect NPRA level or activity only above the control NPRA level or activity; and associating high NPRA level or activity to the presence of NPRA in both the first and second aliquots and low NPRA level or activity to the presence of NPRa only in the first aliquot.

Embodiment 23

The method of embodiment 20, wherein the analyzing step further comprises amplifying any NPRA genetic material in the reaction mixture by a polymerase chain reaction using at least one primer complementary to a NPRA sequence.

Embodiment 24

The method of embodiment 20, wherein the analyzing step comprises detecting NPRA protein using an immunological reagent.

Embodiment 25

The method of embodiment 24, wherein the immunological agent is a monoclonal or polyclonal antibody.

Embodiment 26

The method of any one of embodiments 20 to 25, the sample comprises tumor cells from the subject.

Embodiment 27

The method of any one of embodiments 20 to 26, wherein the sample comprises tissue or cells adjacent to a tumor in the subject.

Embodiment 28

The method of any one of embodiments 20 to 27, wherein a favorable prognosis comprises tumor regression.

Embodiment 29

The method of any one of embodiments 18 to 28, wherein the favorable prognosis comprises longer survival rates relative to patients with unfavorable prognosis.

Embodiment 30

The method of any one of embodiments 20 to 29, further comprising communicating the favorable or unfavorable prognosis to the subject.

Embodiment 31

A purified or isolated antibody or antibody fragment that selectively binds to an epitope within the amino acid sequence comprising or consisting of SEQ ID NO:1, SEQ ID NO:2, or SEQ ID NO:3.

Embodiment 32

A purified or isolated antibody or antibody fragment that selectively binds to both human and mouse natriuretic peptide receptor A (NPRA).

Embodiment 33

The antibody or antibody fragment of embodiment 32, wherein the antibody or antibody fragment selectively binds to an epitope within the amino acid sequence comprising or consisting of SEQ ID NO:3.

Embodiment 34

A method for inhibiting the growth of a malignant cell in vitro or in vivo, comprising administering an agent to the cell, wherein the agent inhibits the function of migration inhibitor factor (MIF) in the malignant cell.

Embodiment 35

The method of embodiment 34, wherein the agent targets a nucleic acid sequence within the MIF gene or transcript and reduces expression of MIF in the malignant cell.

Embodiment 36

The method of embodiment 34 or 35, wherein the malignant cell is a cancer cell selected from the group consisting of prostate cancer, colon cancer, breast cancer, pancreatic cancer, Merkell cell carcinoma, and gastrointestinal stromal tumor (GIST).

Embodiment 37

The method of any one of embodiments 34-36, wherein the agent comprises an RNA interference (RNAi) molecule (e.g., siRNA or shRNA), microRNA (miRNA), antisense oligonucleotide, or ribozyme.

Embodiment 38

A method for providing an NPRA expression profile useful for detecting and/or prognosing cancer, comprising analyzing a biological sample (e.g., sample that may or may not contain malignant cells) from a subject for NPRA level or activity, wherein an elevated NPRA level or activity (relative to a reference NPRA level or activity, such as a normal control or less aggressive stage of the malignancy) is indicative of the presence of a malignancy or a more advanced stage of the malignancy.

Embodiment 39

The method of embodiment 38, further comprising communicating the results of the analysis to a health care provider.

Embodiment 40

The method of embodiment 39, wherein the communication includes transmitting a report to the health care provider electronically (e.g., via the internet) or on a tangible medium (e.g., paper or tangible electronic storage medium).

All patents, patent applications, provisional applications, and publications referred to or cited herein, supra or infra, are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Materials and Methods

Cells and Beta-Actin Antibody.

Normal prostate epithelial cell (PrEC) was purchased from Lonza (Allendale). RWPE, Tramp-C1 and -C3 cells were purchased from the American Type Culture Collection (Manassas, Va., USA). DU145, PC3, benign prostatic hyperplasia (BPH), LNCaP, C4-2, the rat gastric mucosa cell line (RGM1), P2 and CaP2 were described before [22-25]. The beta-actin antibody was obtained from Sigma, the PARP antibody from Santa Cruz Biotechnology, and the MIF antibody from Abcam. Lipofectamine 2000 reagent was obtained from Invitrogen.

NPRA Antibody Production and Purification.

Antibody against NPRA was generated by injecting rabbits (New Zealand white) with 400 µg of synthetic NPRA peptide (amino acid 1010-1031 of mouse NPRA protein, which is homologous to rat and human NPRA) conjugated to keyhole limpet hemocyanin (BioSynthesis, Inc., Lewisville Tex.). Antibody was purified by applying serum to a column of protein A/G agarose (Invitrogen, Carlsbad, Calif.) equilibrated with 20 mM Tris, pH 7.5, 150 mM NaCl, and eluting with 100 mM citrate, pH 3.0. The eluate was neutralized with 5 M NaOH, glycerol was added to 50% and the purified aliquots were stored at −20° C.

Tissue Microarray (TMA) Staining.

A human prostate cancer TMA containing 240 samples, prepared in the histology laboratory of the Moffitt Cancer Center Tissue Core Facility was used to test for expression of NPRA and MIF. The TMA slide was stained using a Ventana Discovery XT automated system (Ventana Medical Systems, Tucson, Ariz.), according to the manufacturer's protocol. Briefly, slides were deparaffinized on the automated system with EZ Prep solution (Ventana). Following heat-induced antigen retrieval, the slide was incubated with NPRA antibody (1:300) or MIF antibody (R&D System, MN) for 32 min and Ventana anti-rabbit or anti-goat secondary antibody for 20 min. The detection system used was the Ventana OmniMap kit, and the slide was then counterstained with hematoxylin and dehydrated.

Data Analysis.

The TMA slide was scored for intensity and cellularity by an expert pathologist. Positive staining for NPRA or MIF was scored into four grades, according to the intensity: 0, 1+, 2+ and 3+. The percentage of NPRA-positive cells was scored into three categories: 1 (0-33%), 2 (34-64%) and 3 (65-100%). The product of the intensity and percentage scores was used as the final score. The final score was classified as: 0, negative; 1-3, weak; 4-6, moderate; and 7-9, strong. Both the Kruskal-Wallis test and the Wilcoxon-Mann-Whitney test were used to compare the scores by groups. Comparisons were done for (1) PIN-L vs. BPH; (2) PIN-H vs. BPH; (3) Gleason-6 vs. BPH; (4) Gleason-7 vs. BPH; (5) Gleason-8 to 10 vs. BPH and (6) AI vs. BPH.

Spearman's correlation coefficient was used to analyze the relationship between NPRA or MIF expression and Gleason's grading score.

Animals.

Male C57BL/6 mice were purchased from the National Cancer Institute. Male C57BL/6 NPRA-KO or NPRA-het were described before [19]. All mice were maintained in a pathogen-free environment and all procedures were reviewed and approved by the University of South Florida Institutional Animal Care and Use Committee.

Preparation of Plasmid Nanoparticles and Administration to Mice.

Plasmids encoding $NP_{73-102}$, $hNP_{73-102}$ and VD were constructed as described previously [14, 19]. Plasmids encoding siRNAs against NPRA were described previously [19]. Plasmids encoding shNPRAs were purchased from Origene. For transfection, epithelial cells at 60% confluence (log phase) were incubated in complete medium at 37° C. with plasmid DNA (1 µg/$10^6$ cells) complexed with lipofectamine (GibcoBRL Life Technologies, Carlsbad, Calif.). For tumor cell inoculation, TRAMP-C1 cells were trypsinized, washed and resuspended in PBS at $5 \times 10^7$ cells per ml. Mice were injected s.c. in the flank with 100 uL of resuspended cancer cells. For evaluating the effects of iNPRA in modulating tumor progression, plasmids were encapsulated in chitosan nanoparticles (25 ug of plasmid plus 125 ug of chitosan), were administered i.p. twice a week until sacrificed. Tumor sizes were measured by calipers, and at the end of experiment (day 62), the mice were euthanized and the tumors were removed and weighed. Proteins from tumors were extracted and examined for NPRA and MIF expression by Western blotting.

Western Blot Analysis.

Western blot assay was performed as previously described [25]. Cells were lysed, total cellular protein (120 µg) was separated by SDS-PAGE, blotted to nitrocellulose, and incubated with antibodies to specific proteins. Bands were visualized by enhanced chemiluminescence (Amersham Life Sciences, Piscataway, N.J.) on Kodak X-OMAT-AR film.

SuperArray Analysis of Prostate Tissues.

NPRA-KO and WT C57BL/6 mice (n=4) were injected i.p. with LPS (1 mg/kg body weight) for 3 hrs, prior to prostate harvesting. Total RNA was isolated using an RNAeasy kit (QIAGEN, Valencia, Calif.) and a pool of total RNA by group hybridized to the mouse autoimmune and inflammatory response Oligo GEarray (SuperArray Frederick, Md.), according to the manufacturer's instructions. The X-ray films were scanned, and the spots were analyzed using SuperArray Software. The relative expression level was determined by comparing the signal intensity of each gene in the array after normalization to the signal of a set of housekeeping genes.

Statistics.

The number of mice used in each test group was a minimum of 4. Experiments were repeated at least once, and measurements were expressed as means±SD. Pairs of groups were compared through the use of Student's t tests. Differences between groups were considered significant at p=0.05.

Example 1—Development of Antibody Specific for Human NPRA

Figure 1A:
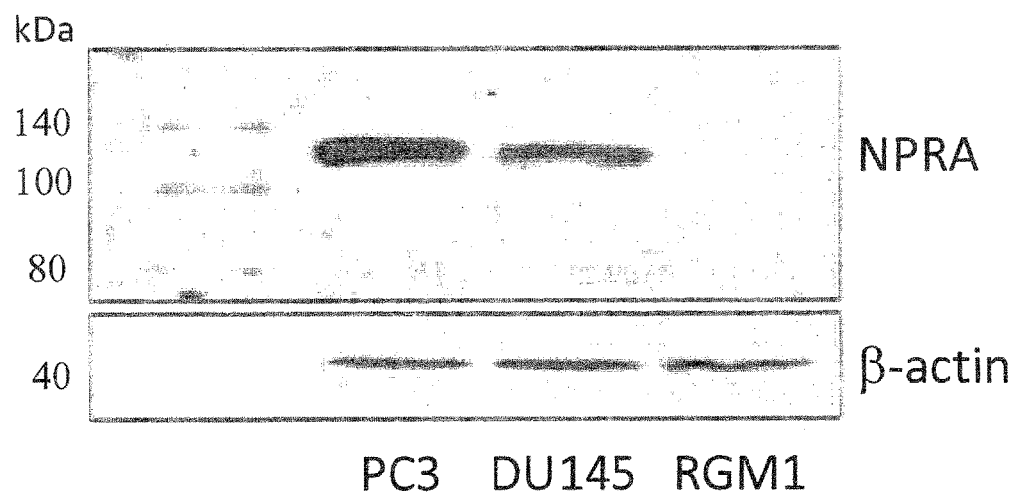
FIGS. 1A-1D show results of immunoblot analysis demonstrating specificity of an anti-NPRA antibody (antibody 3 specific to SEQ ID NO:3).
Figure 1B:
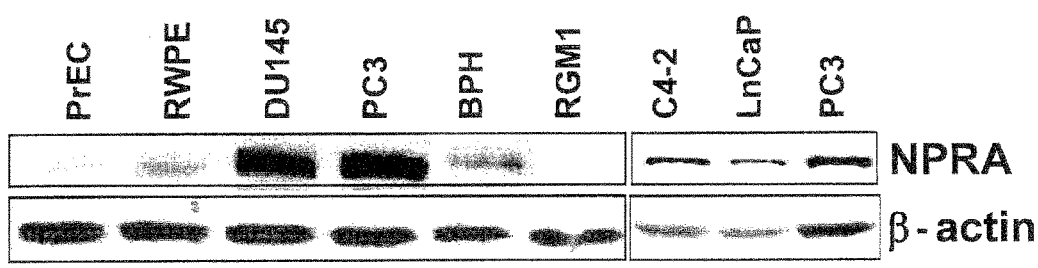

To examine the expression of NPRA protein in human PCa, the present inventors raised antibodies to three NPRA peptides (SEQ ID NOs: 1-3) conjugated with KLH in rabbits. The specificity of the anti-NPRA antibody was confirmed by immunoblot analysis. Three antibodies were screened, of which only one (antibody SEQ ID NO: 3) enables detection of human NPRA expression in a very specific manner while another is reactive to mouse, but not human, NPRA. As shown in FIGS. 1A and 1B, an approximately 120 kDa band corresponding to NPRA was detected only in human PCa cell lines, PC3 and DU145, but not in rat Rat gastric mucosa cell line, RGM1. The later does not express NPRA (6). The specificity of the anti-NPRA antibody was further confirmed in cell lysates prepared from PC3 cells transfected with a NPRA inhibitor.

Example 2—Examining NPRA Expression in Human PCa Specimens

Figure 2:
FIG. 2 shows the strong immunoreactivity for NPRA in human prostate TMA. A 200× image of a representative sample from each disease stage is shown.
Figure 2:
Figure 2:
Figure 2:
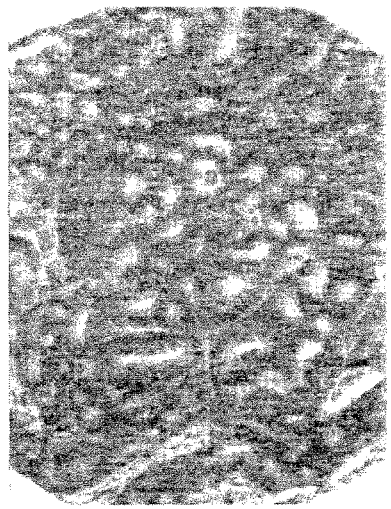
Figure 2:
Figure 2:
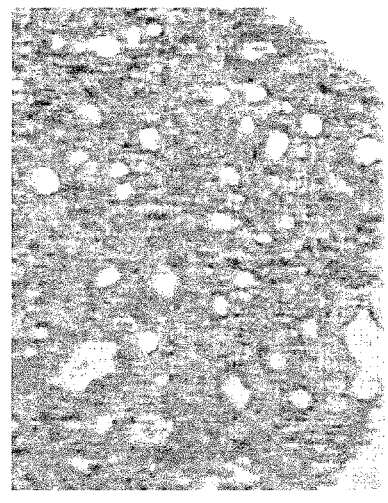

A human PCa tissue microarray (TMA) containing 240 samples, prepared in the histology laboratory of the Moffitt Cancer Center Tissue Core Facility was used to test for NPRA expression during PCa progression. The prostate TMA included 24 samples of benign prostatic hyperplasia (BPH), 21 samples of regular prostatic intraepithelial neoplasm (PIN-R), 14 samples of high PIN (PIN-H), 33 samples of prostate carcinoma (PC) with a Gleason score of 6, 82 samples of PC with a Gleason score of 7, 15 samples of androgen independent (AI) PC, and 51 samples of PC with a Gleason score of 8 and up was selected for immunohistochemical staining with our human NPRA antibody. The TMA slide was stained using a Ventana Discovery XT automated system (Ventana Medical Systems, Tucson, Ariz.), as per the manufacturer's protocol. Briefly, slides were deparaffinized on the automated system with EZ Prep solution (Ventana). Following the heat-induced antigen retrieval the slide was incubated with NPRA antibody (1:300) for 32 min and Ventana anti-rabbit secondary antibody for 20 min. The detection system used was the Ventana OmniMap kit, and the slide was then counterstained with Hematoxylin and dehydrated. A representative image (200×) of one sample from each disease stage is shown in FIG. 2. The results demonstrate that the majority of epithelial cells in BPH and PIN-R expressed NPRA with weak intensity, in PIN-H with weak-moderate intensity and in Gleason-6 samples with moderate-strong intensity. Weak and focal staining of stromal/inflammatory cells was also observed in these samples.

Figure 3:
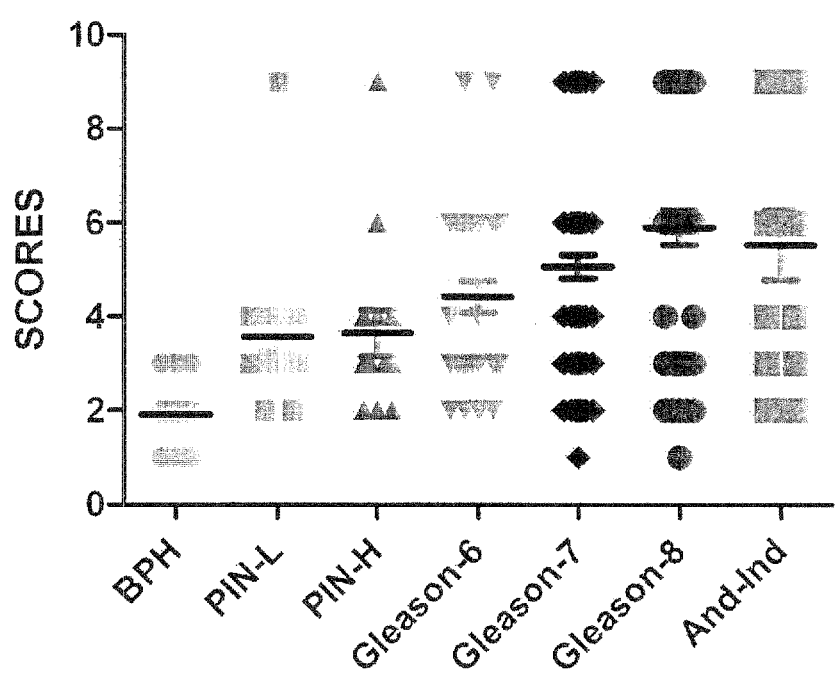
FIG. 3 is a graph showing the final NPRA scores for each sample of different stages of PCa. The bar represents the mean sample score for each category of PCa.

In contrast, NPRA staining was uniform, strong and prominent in epithelial tumors of Gleason-7 and -8 and in AI samples. Stromal/inflammatory cells of Gleason-7 and Gleason-8 also showed NPRA expression with moderate intensity. The TMA slide was scored for intensity and cellularity by Dr. Domenico Coppola, Scientific Director, Tissue Core Facility at the H. Lee Moffitt Cancer Center. The positive reaction of NPRA was scored into four grades, according to the intensity of the staining: 0, 1+, 2+ and 3+. The percentage of NPRA positive cells was scored into three categories: 1 (0-33%), 2 (34-64%) and 3 (65-100%). The product of the intensity and percentage scores was used as the final score. The final score was classified as: 0, negative; 1-3, weak; 4-6, moderate; and 7-9, strong. FIG. 3 shows the distribution of scores in each disease stage. The results suggest that mean sample score increased during PCa progression.

NPRA expression studies in human tissues have been limited by lack of availability of appropriate antibodies to NPRA. The antibodies that are commercially available are very poor in quality and do not provide consistent results. The present inventors developed an antibody to NPRA in rabbits using a specific antigenic peptide (amino acid 1010-1031 of mouse NPRA protein, which is homologous to rat and human NPRA). As shown in FIG. 1A, an approximately 120 kDa band corresponding to NPRA was detected only in human PCa cell lines, PC3 and DU145 that express NPRA, but not in the RGM1 cell line that does not express NPRA [22]. The specificity of the anti-NPRA antibody was confirmed by ELISA assay (data not shown), and by immunofluorescence and immunohistochemistry assays (FIG. 13A).

Figure 1C:
Figure 1C:
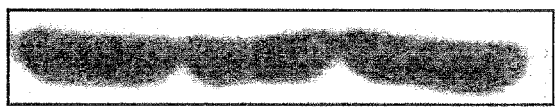
Figure 1D:
Figure 1D:

The inventors examined NPRA expression by western blotting in various types of PCa tumors and compared it with normal prostate epithelial (PrEC and RWPE) and benign prostatic hyperplasia (BPH) cells. Results of the western blot show that NPRA is expressed abundantly in the androgen-dependent PCa cell line, LNCaP and androgen-independent cell lines C4-2, PC3 and DU145, but not in PrEC cells and only weakly in RWPE and BPH cells (FIG. 1B). Lysates of normal RGM1 that does not express NPRA were used as control. NPRA is also highly expressed in transplantable syngeneic tumor lines derived from TRAMP (transgenic adenocarcinoma mouse prostate) mice which get spontaneous PCa. NPRA is strongly expressed in the tumorigenic TRAMP-C1 and -C2 PCa cell lines but less abundantly in the non-tumorigenic TRAMP-C3 PCa cell line (FIG. 1C) [26]; the latter shows a three-fold reduction in growth and colonization potential compared to TRAMP-C1 and C2 cells (FIGS. 14A-C). In addition, increased NPRA expression was seen in prostate epithelial lines from intact conditional homozygous Pten knock-out mice (PTEN-CaP2) that are tumorigenic compared to heterozygous Pten knock-out mice (PTEN-P2) (FIG. 1D) [23]. These results suggest that NPRA is more abundantly expressed in PCa cells than normal or benign prostate epithelial cells.

Example 3—Association of NPRA Expression with PCa Progression

The clinical relevance of NPRA expression during human PCa development was examined in BPH, high grade PIN (prostatic intraepithelial neoplasm) and prostatic adenocarcinoma using a human PCa tissue microarray (TMA) containing 240 samples. The TMA samples included BPH (n=24), low grade prostatic intraepithelial neoplasm (PIN-L) (n=21), high PIN (PIN-H) (n=14), prostate carcinoma (PC) with a Gleason score of 6 (n=33), PC with a Gleason score of 7 (n=82), PC with a Gleason score of 8 to 10 (n=51) and androgen-independent (AI) PC (n=15). The TMA slide was immuno-stained with a rabbit anti-human NPRA antibody using a Ventana Discovery XT automated system (Ventana Medical Systems, Tucson, Ariz.) and the data were statistically analyzed. A representative image (200×) of one sample from each disease stage is shown in FIG. 2. The results demonstrate that the majority of epithelial cells in BPH and PIN-L were weakly stained with NPRA, and that the PIN-H samples were weakly to moderately positive for NPRA. Gleason-6 PCa samples exhibited moderate to strong NPRA immunoreactivity. Weak and focal staining of stromal/inflammatory cells was also observed in these samples. In contrast, NPRA staining was uniformly strong and prominent in Gleason 7-10 and in AI PCa samples. Stromal/inflammatory cells in these samples also showed moderate NPRA expression.

The TMA slide was scored for intensity and cellularity by an expert pathologist. The final score was classified as: 0, negative; 1-3, weak; 4-6, moderate; and 7-9, strong. FIG. 2B shows the distribution of scores in each disease stage. The results show that the mean sample score increased during PCa progression. Table 1 displays a median analysis of NPRA expression in the TMA for 240 subjects. Across all 240 subjects, the median score was 4. Table 2 shows the frequency in each disease group of having a score falling at or below the median and having one above the median. The number of observations in the BPH group with a score >4 was zero, while for Gleason-6, Gleason-7, Gleason-8-10 and AI groups the numbers were respectively 14 (of 33), 43 (of 82), 34 (of 51) and 8 (of 15). A chi-square (two-way frequency table) value of 50.761 with asymptomatic significance of p<0.0001 was obtained, suggesting that the relationship between NPRA expression and PCa stage is very strong. A Kruskal-Wallis test indicated that the difference in NPRA expression among the seven diagnostic groups was highly significant (p<0.0001). The pairwise Wilcoxon-Mann-Whitney tests and p values in Table 1 show that NPRA expression is strongly associated with PCa progression. The elevated NPRA expression in high-grade tumors may reflect its role in tumor-stromal interaction. Since the outcomes of the Kruskal-Wallis and Wilcoxon-Mann-Whitney tests are of ordinal value and do not follow the normal distribution that the ANOVA or t-test requires a non-parametric version of these two methods was used.

TABLE 1

|  | N | Mean | Std. Deviation | Minimum | Maximum | 25th | 50th (Median) | 75th |
|---|---|---|---|---|---|---|---|---|
|  |  |  |  |  |  | Percentiles | | |
| Score | 240 | 4.66 | 2.431 | 1.00 | 9.00 | 3.00 | 4.00 | 6.00 |
| Disease | 240 | 4.57 | 1.8711 | 1.00 | 7.00 | 4.00 | 5.00 | 6.00 |

TABLE 2

| Score | B PH | PIN (Regular) | PIN (High) | PC Gleason 6 | PC Gleason 7 | PC (AI) | PC Gleasons 8-10 |
|---|---|---|---|---|---|---|---|
| >Median | 0 | 1 | 2 | 14 | 43 | 8 | 34 |
| ≤Median | 24 | 20 | 12 | 19 | 39 | 7 | 17 |

Thus, taken together, these results demonstrate a statistically significant difference in staining between BPH, PIN and prostatic adenocarcinoma, suggesting that NPRA expression is strongly associated with PCa progression. Hence, targeting NPRA signaling in PCa is highly relevant.

NPRA is more abundantly expressed in human PCa cells than in normal cells or prostate epithelial cells associated with benign prostatic hyperplasia (BPH), and its expression positively correlates with the Gleason score (GS) in clinically aggressive human PCa tissue (FIG. 17A). Thus, in accordance with the invention, NPRA expression levels may be used to detect and distinguish human PCa from normal cells and BPH. Additionally, since NPRA expression positively correlates with GS in aggressive PCa tissue, NPRA expression levels may be used to classify (stage) prostate cancer as to its clinical aggressiveness. The inventors used an identical PCa tissue microarray (TMA) to compare the expression of NPRA and prostate specific membrane antigen (PSMA), a transmembrane protein whose expression is increased in hormone-refractory PCa (FIG. 17B). NPRA expression correlated significantly with PSMA expression (Spearman's, r=1.000; p=0.0028, two-tailed) in each disease stage, but was more predictive in PCa with a core diagnosis of GS-7 (p<0.0001) and GS-8 (p<0.05) (FIG. 17C; Mann-Whitney test).

Example 4—Association of NPRA Expression with Colorectal Cancer

Figure 4:
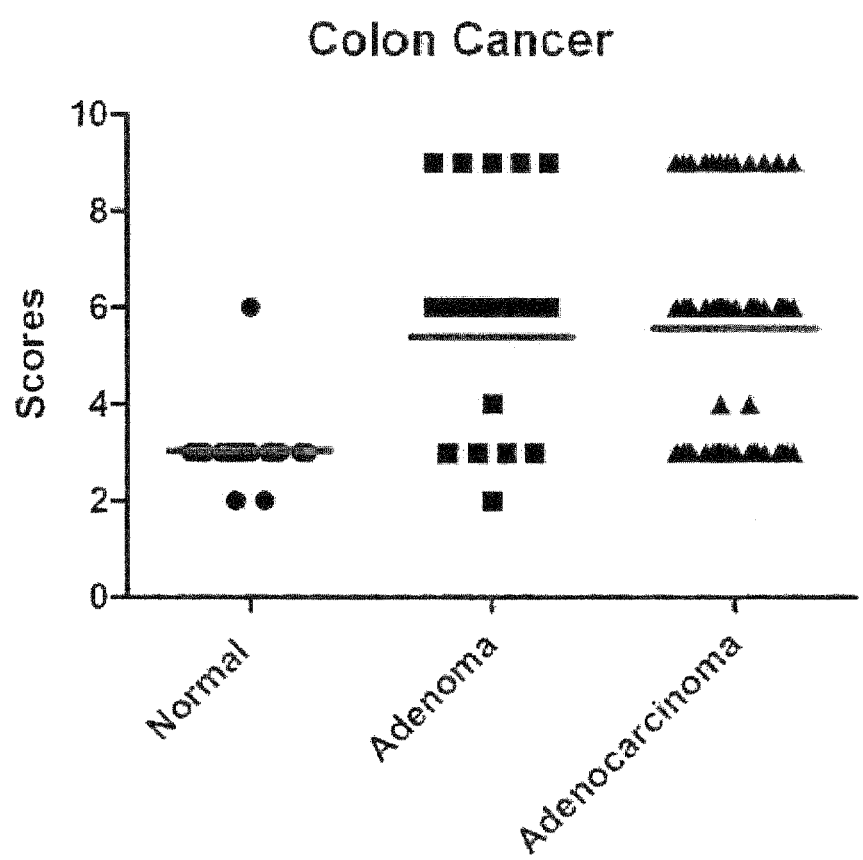
FIG. 4 shows the final scores for each sample of different stages of colon cancer are shown. These include, normal (n=24); adenoma (n=24) and adenocarcinoma (n=78). The bar represents the mean sample score for each category.

The present inventors analyzed the data two different ways, each of which indicates that NPRA expression is associated with colorectal cancer. The colon cancer TMA included normal (n=24); adenoma (n=24) and adenocarcinoma (n=78). The TMA slide was scored for intensity and cellularity. The results are shown in FIG. 4, which shows the distribution of scores in each disease stage. The results suggest that mean sample score increased during colorectal cancer.

Example 5—Association of NPRA Expression with Breast Cancer

Figure 5:
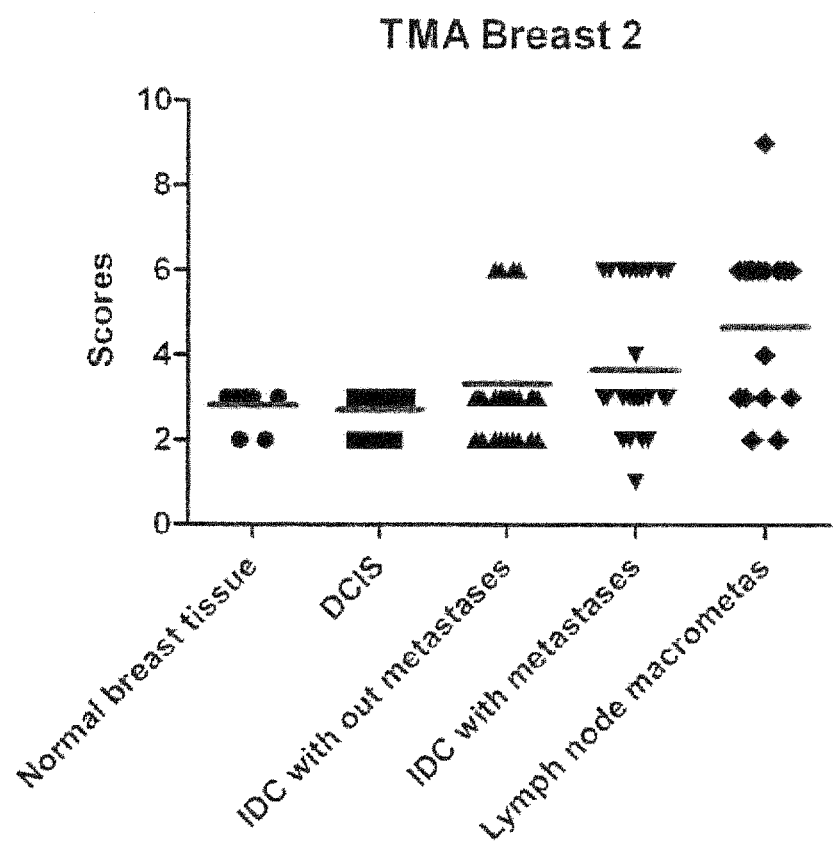
FIG. 5 shows the final scores for each sample of different stages of breast cancer are shown. These include, normal breast tissue (n=11); DCIS (n=14), IDC without metastases (n=28), IDC with metastases (n=31) and lymphnode metastases (n=21). The bar represents the mean sample score for each category.

The present inventors analyzed the data two different ways, each of which indicates that NPRA expression is associated with breast cancer. The breast cancer TMA included normal breast tissue (n=11); DCIS (n=14), IDC without metastases (n=28), IDC with metastases (n=31) and lymph node metastases (n=21). The TMA slide was scored for intensity and cellularity. The results are shown in FIG. 5, which shows the distribution of scores in each disease stage. The results suggest that mean sample score increased during breast cancer.

Example 6—Association of NPRA Expression with Pancreatic Cancer

Figure 6:
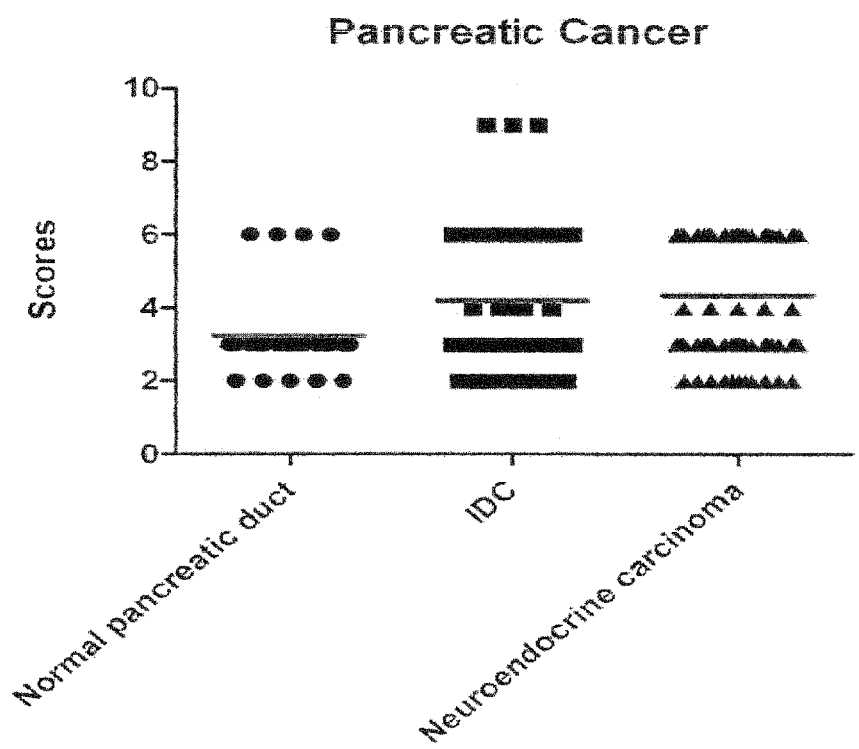
FIG. 6 shows the final scores for each sample of different stages of pancreatic cancer are shown. These include, normal pancreatic duct (n=54); IDC (n=68), and neuroendocrine carcinoma (n=158). The bar represents the mean sample score for each category.

The present inventors analyzed the data two different ways, each of which indicates that NPRA expression is associated with pancreatic cancer. The breast cancer TMA included pancreatic duct (n=54); IDC (n=68), and neuroendocrine carcinoma (n=158). The TMA slide was scored for intensity and cellularity. The results are shown in FIG. 6, which shows the distribution of scores in each disease stage. The results suggest that mean sample score increased during pancreatic cancer.

Example 7—Association of NPRA Expression with Merckell Cell Carcinoma

Figure 7:
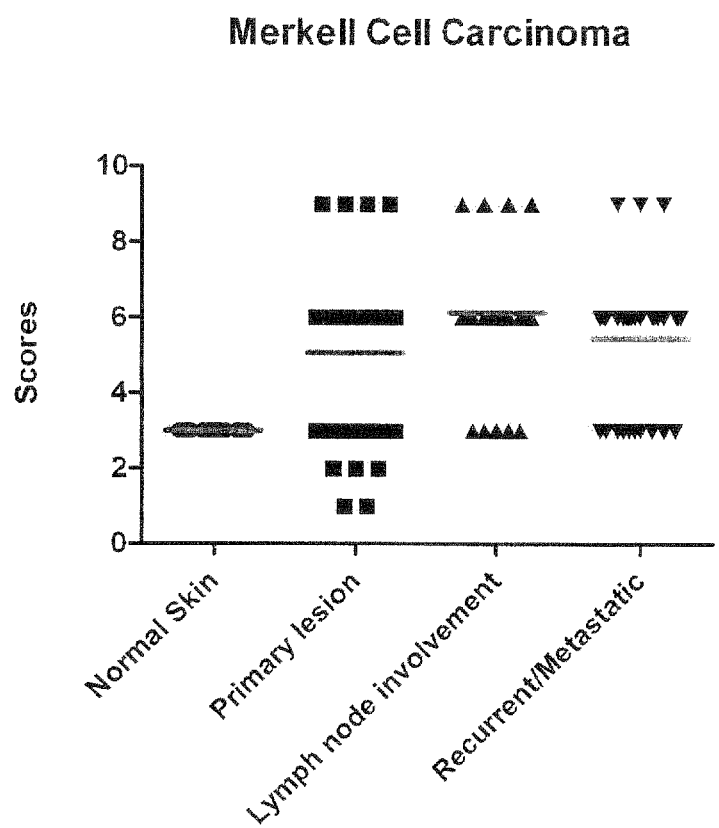
FIG. 7 shows the final scores for each sample of different stages of merkell cell carcinoma are shown. These include, normal skin (n=21); primary lesion (n=98), lymphnode involvement (n=65) and recurrent/metastatic (n=38). The bar represents the mean sample score for each category.

The present inventors analyzed the data two different ways, each of which indicates that NPRA expression is associated with pancreatic cancer. The merckell cell carcinoma TMA included normal skin (n=21); primary lesion (n=98), lymphnode involvement (n=65) and recurrent/metastatic (n=38). The TMA slide was scored for intensity and cellularity. The results are shown in FIG. 7, which shows the distribution of scores in each disease stage. The results suggest that mean sample score increased during merckell cell carcinoma.

Example 8—Association of NPRA Expression with GIST

Figure 8:
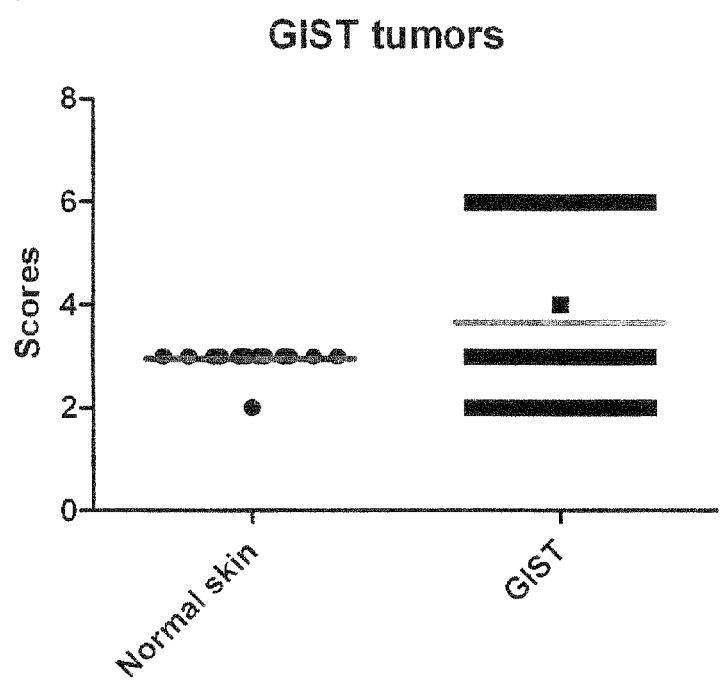
FIG. 8 shows the final scores for each sample of different stages of GIST tumors are shown. These include, normal skin (n=21); and GIST (n=124). The bar represents the mean sample score for each category.

The present inventors analyzed the data two different ways, each of which indicates that NPRA expression is associated with GIST cancer. The GIST TMA included normal skin (n=21); GIST tumor (n=124). The TMA slide was scored for intensity and cellularity. The results are shown in FIG. 8, which shows the distribution of scores in each disease stage. The results suggest that mean sample score increased in GIST.

Example 9—NPRA Deficiency Impairs Engraftment of PCA Cells

Figure 9A:
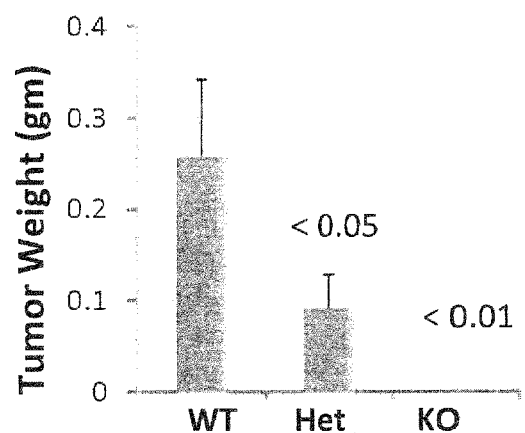
FIGS. 9A-C demonstrate effects of NPRA deficiency.
Figure 9B:
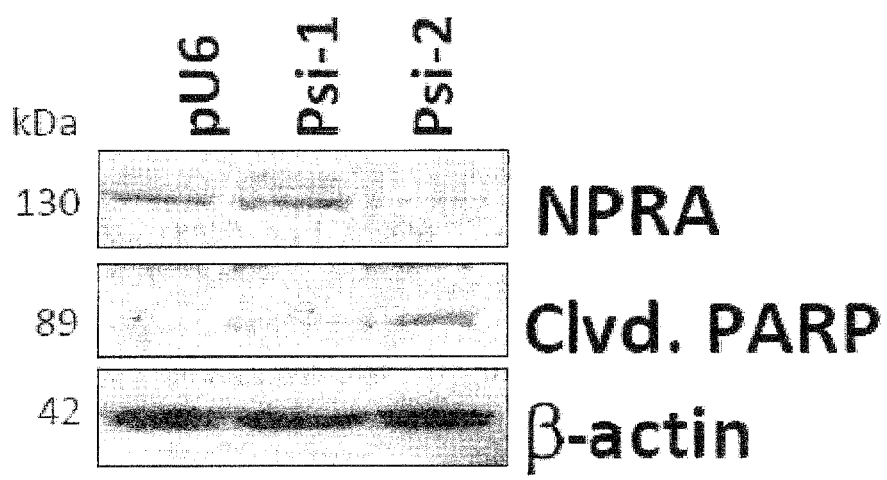
Figure 9C:
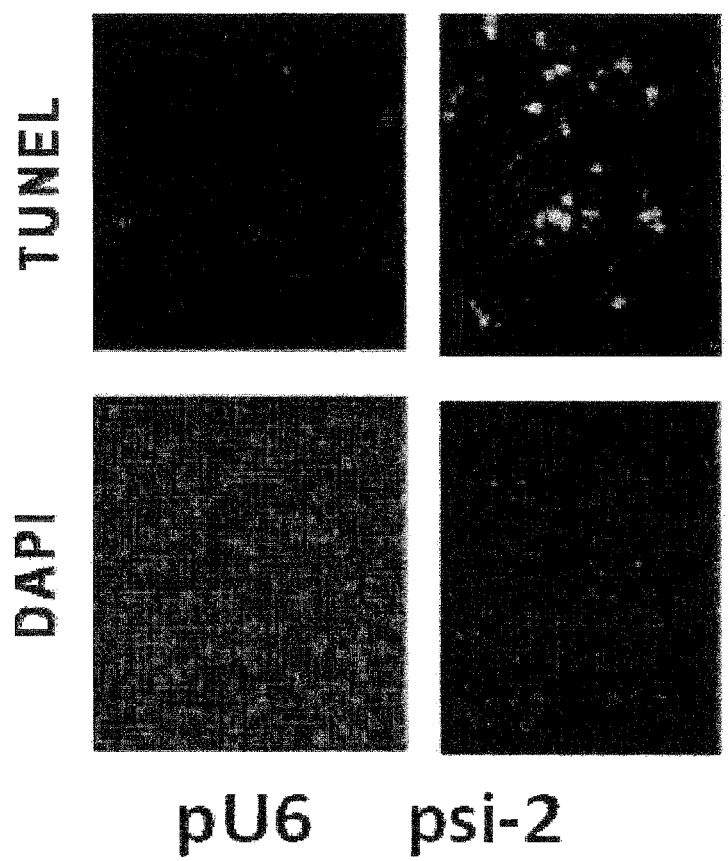

The present inventors proposed that NPRA might be important for prostate tumor growth. The role of NPRA in modulating PCa progression was tested using TRAMP-C1 cells, which form tumors when grafted subcutaneously into syngeneic C57BL/6 hosts [26]. For in vivo assays, C57BL/6 (WT), NPRA-heterozygous (NPRA-het) and NPRA-KO mice were injected subcutaneously with TRAMP-C1 cells. Mice were euthanized seven weeks after injection and tumor sizes and weights were compared (FIG. 9A). TRAMP-C1 cells failed to engraft in NPRA-KO mice and no visible tumors were detected in the homozygous group ten weeks after tumor cell injection. Some tumor growth was observed in NPRA-het mice, but at a significantly reduced level compared to that in WT C57BL/6 mice, suggesting that host NPRA gene dosage is a determining factor for the growth of tumor cells in these mice. The role of NPRA deficiency in the survival of TRAMP-C1 cells was tested in vitro by ectopic expression of a plasmid encoding small interfering RNA against NPRA (siNPRA). Expression of siNPRA-2, but not siNPRA-1, significantly reduced expression of NPRA (FIG. 9B). Apoptosis was detected by western blotting for PARP cleavage (FIG. 9B) and by the terminal transferase dUTP nick end labeling (TUNEL) assay (FIG. 9C). Downregulation of NPRA expression by siNPRA-2 induced significant apoptosis in PCa cells.

Example 10—NPRA Down-Regulation Inhibits Migration Inhibitory Factor (MIF) Expression It has been previously that NPRA-deficient mice fail to mount an inflammatory response, as exemplified by the lack of goblet cell hyperplasia and infiltration of eosinophils in the lungs of NPRA-KO mice compared to those of WT mice, when sensitized and challenged with ovalbumin [19]. The lack of inflammatory response correlated with reduced levels of inflammatory cytokines IL-4, IL-5 and IL-6 in the bronchoalveolar lavage (BAL) fluid of the NPRA-KO mice relative that of WT mice [19, 27]. To examine whether the anti-tumor effects of iNPRA were due to lack of local inflammation in prostate tissue, the inventors injected mice with lipopolysaccharide (LPS), a potent inducer of local inflammation and compared prostate tissues for alterations in gene expression in WT and NPRA-KO mice. Prostate tissue was collected from LPS-treated and control mice, and total RNA was examined for differential gene expression using a mouse autoimmune and inflammatory response oligo GEarray (SuperArray, MD). Analysis of genes altered (more than two-fold) during LPS challenge in WT and NPRA-KO mice identified 24 genes that are either upregulated (15) or downregulated (9) in the prostate tissue of NPRA-KO mice compared to their expression levels in control mice. A few of the genes that are down-regulated during LPS stimulation in NPRA-KO mice is shown in FIG. 4A, and include: fibronectin 1 (Fn1), which is involved in the acute phase response [28], granulin [29] and S100 calcium binding protein A 11 (S100a11) [30], which are cytokines, IL6 signal transducer (IL6st; also known as gp130), a cytokine receptor [31, 32] and MIF, which is involved in the inflammatory response [33].

Figure 10A:
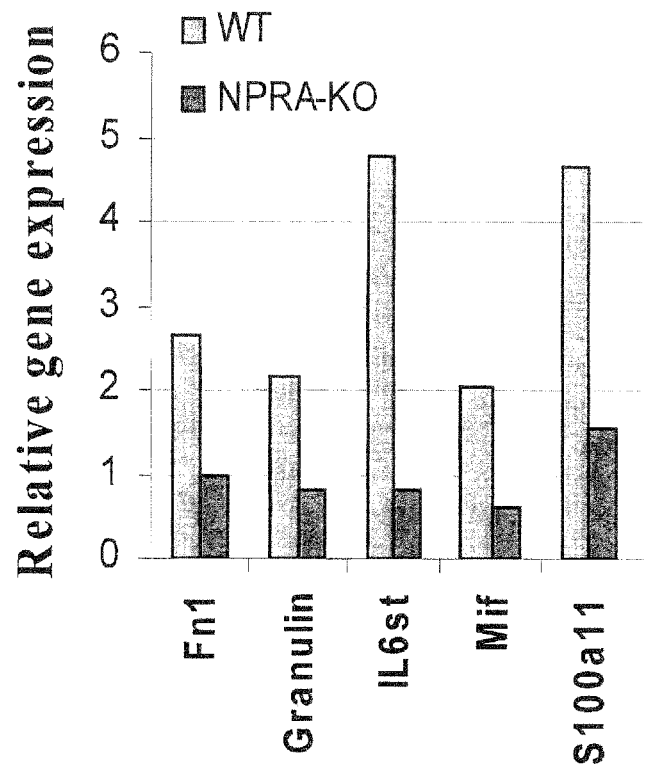
FIGS. 10A-C show that NPRA depletion inhibits MIF expression. SuperArray analysis of prostate tissues of NPRA-KO and WT C57BL/6 mice. The relative expression level of genes that are altered in the prostate tissues of NPRA-KO vs. WT is shown in FIG. 10A. TRAMP-C1 cells were transfected with pshNPRAs or $pNP_{73-102}$ plasmid. Whole cell lysates were extracted 72 hrs after transfection and examined for NPRA and MIF by Western blotting. Results are shown in FIGS. 10B and 10C.
Figure 10B:
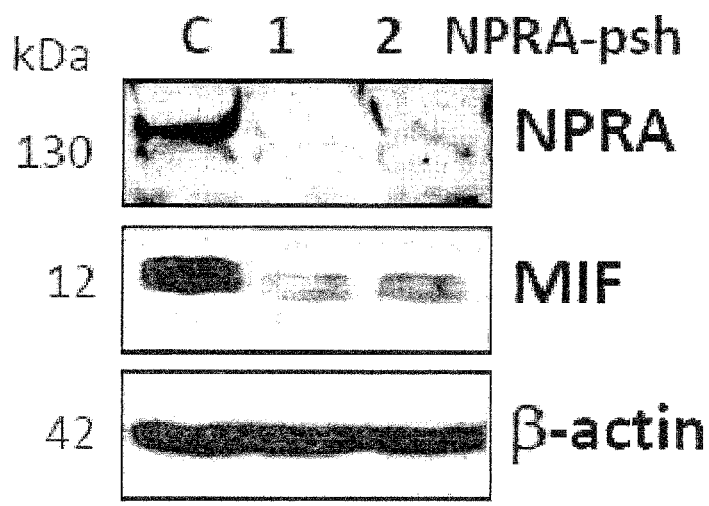
Figure 10C:
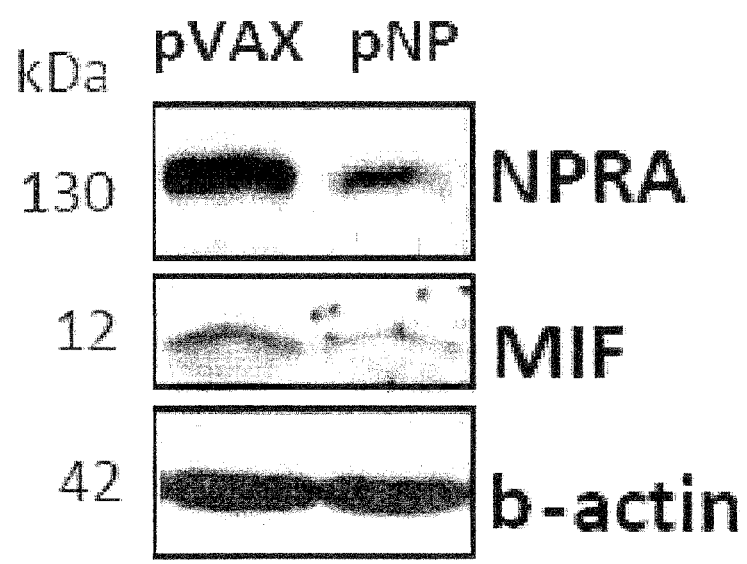

Since MIF has been reported to be involved in PCa progression [24, 33, 34], the possibility that NPRA depletion modulates MIF expression was tested using shRNAs for NPRA in TRAMP-C1 cells. As shown in FIG. 10B, transfection of TRAMP-C1 cells with shNPRA-1 and shNPRA-2 reduced NPRA expression >80% and also decreased MIF expression >90%. Since overexpression of plasmid-encoded $NP_{73-102}$ downregulates NPRA (FIG. 15), $pNP_{73-102}$ was also used as an inhibitor of NPRA (INFRA) in this study. Ectopic expression of the plasmid encoding $NP_{73-102}$, but not the pVAX vector, reduced both NPRA and MIF expression >50% in TRAMP-C1 cells (FIG. 10C).

Example 11—iNPRA Inhibits Tumor Burden by Down-Regulating MIF

Figure 11C:
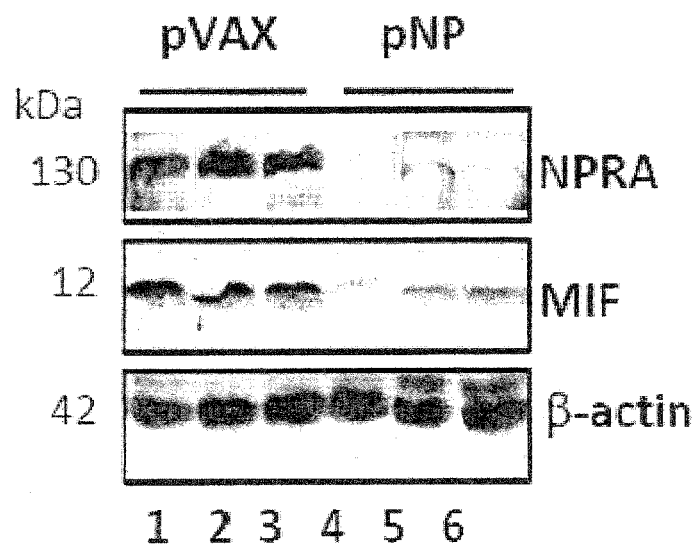

To rule out the possibility that impaired engraftment of TRAMP-C1 cells in NPRA-KO mice is due to immune rejection, the inventors examined the potential of NPRA inhibition to block the growth of TRAMP-C1 cells in immunocompetent C57BL/6 mice. Mice were inoculated with TRAMP-C1 cells and divided into four groups. Two weeks later, mice in each group were injected i.p. twice a week with chitosan nanoparticles (CNPs) encapsulating plasmid DNA (25 ug/mouse) encoding empty vector (pVAX), $pNP_{73-102}$, a control peptide encoding human vessel dilator (pVD) or a combination of 12.5 ug each of $pNP_{73-102}$ and pVD, using methods as described [19, 20]. Mice were monitored for tumor growth and tumor sizes were recorded on the indicated days (FIG. 11A). Tumor growth was significantly inhibited in mice treated with $pNP_{73-102}$ compared to pVAX- or pVD-treated groups. Mice were euthanized on day 65 after treatment, and tumor weights were measured and compared (FIG. 11B). As shown in FIGS. 11A and 11B, a significant reduction ($p<0.05$) in tumor burden was seen in mice treated with 25 ug of $pNP_{73-102}$ but not with the pVAX or pVD plasmids. Mice treated with 12.5 ug $pNP_{73-102}$ showed only moderate inhibition of tumor burden. The plasmid pVD encodes a peptide corresponding to human VD and is not homologous with mouse VD; thus, lack of any anti-tumor effects in pVD-treated mice suggests the specificity of these peptides in vivo. To understand the anti-tumor effects of $pNP_{73-102}$, the inventors examined NPRA and MIF expression in TRAMP-C1-engrafted tumor lysates from representative control (pVAX) and $pNP_{73-102}$-treated mice. The results (FIG. 11C) show that treatment of mice with $pNP_{73-102}$, but not with pVAX, significantly reduced expression of NPRA and MIF; therefore, expression of these proteins may be linked to growth of primary tumors in TRAMP-C1-inoculated C57BL/6 mice.

The inventors also examined NPRA and MIF expression in primary prostate tumors from TRAMP mice. Western blots showed that NPRA and MIF are detected in the lysates of primary prostate tumors from TRAMP mice of varying ages (18-30 weeks of age) (FIG. 12A; lanes 1-4) but not in prostates from age-matched WT C57BL/6 mice (18 and 28 weeks of age) (FIG. 12A; lanes 5-6). These results suggest that tumor cell lines, as well as primary prostate tumors of TRAMP mice, show significantly higher levels of NPRA and MIF compared to normal cells or prostate cells from C57BL/6 mice. The inventors also compared NPRA and MIF expression in total cell lysates of human PCa cells by Western blotting. Results presented in FIG. 12B suggest that increased MIF was seen in the lysates of PC3 and DU145 cells that express NPRA abundantly (FIG. 1B) compared to the lysates of BPH and RWPE. The results of these studies suggest that NPRA regulates MIF expression in PCa cells.

There remain several challenges in PCa research: the lack of specific clinical markers for early diagnosis and prognosis of PCa and the need to identify drugs that target AI-PCa tumor cells directly without damaging healthy cells. In this study, the inventors show that NPRA is a biomarker for PCa and candidate for PCa therapy.

An important finding of this study is the demonstration that NPRA is significantly over-expressed in mouse and human PCa cells compared to normal cells. Screening of a human PCa TMA containing 240 tissue samples shows that NPRA is also over-expressed in human tissues including high grade PIN (prostatic intraepithelial neoplasm) and prostatic adenocarcinoma. The benign hyperplastic glands exhibited significantly lower NPRA expression than localized PCas. These data are consistent with the previous report and with the data in this study, showing that NPRA is highly expressed in both human and mouse PCa cell lines and in advanced PCa tissues, but not in a normal prostate epithelial cell line or in a benign prostate hyperplasia epithelial cell line [19, 35, 36]. It is to be noted that NPRA was expressed in androgen dependent cell line LNCaP but not in stromal cell line, WPMY. However, expression of ANP was detected in the culture supernatant of PC3 and DU145 PCa cells and WPMY stromal cells but not in normal prostate epithelial cells or LNCaP cells (unpublished observation). The inventors found a significant association between NPRA expression and Gleason score and pathological stage. Results from the TMA studies show that NPRA is an independent predictor of advanced PCa, and may therefore be useful as a clinical marker. Although, a number of marker antigens have been reported for PCa, none of them is specific enough to pass the clinical test for use in PCa prognosis. Given the strong positive correlation ($r=0.64$, $p<0.005$) between NPRA expression and the severity of the clinical stage, particularly in AI-PCa, NPRA may prove to be an effective clinical prognostic marker.

This study also suggests that NPRA may be a drug target for treating PCa and other cancers. Using the TRAMP-C1 spontaneous PCa model, the inventors demonstrated that NPRA-KO mice, which have normal heart, kidney and vascular function, have no detectable increase in postnatal mortality, do not permit growth of implanted PCa cells and have a normal life-span of over 24 months. Tumor growth is observed in NPRA-het mice but at a significantly reduced level compared to that in WT C57BL/6 mice, which indicates that host NPRA gene dosage is a determining factor for the growth of tumor cells in mice. This finding is consistent with the reports that ANP peptides (ANP and VD) inhibit the proliferation of PCa cells in vitro and in mice [35]. This is presumably due to the feedback inhibition of NPRA expression caused by high doses of ANP or other natriuretic peptides, such as $NP_{73-102}$ [18, 35, 37, 38]. Thus, while low doses of these peptides stimulate NPRA signaling, high doses inhibit NPRA signaling and show anticancer effects. In sum, NPRA provides a heretofore undescribed target for PCa. This hypothesis is also supported by the observation that NPRA is an upstream regulator of IL-6, which has been reported as a target for PCa therapy [39, 40].

In view of the finding that $pNP_{73-102}$ inhibits NPRA expression, the inventors examined its role in treating PCa. TRAMP-C1 cells injected into C57BL/6 mice induced tumors in the control mice but not in $pNP_{73-102}$-treated mice. These findings demonstrate the potential utility of $pNP_{73-102}$ for the treatment of PCa. Although the mechanism of tumor inhibition by $pNP_{73-102}$ is unknown, the evidence that $pNP_{73-102}$ significantly decreases the expression of NPRA suggests that this may be the explanation for its antitumor effect. A perceived limitation in iNPRA therapy for PCa is the normal physiological role of NPRA in blood pressure regulation. To address this issue, the inventors compared blood pressure of NPRA-KO mice with that of TRAMP mice and found no relationship between NPRA expression, blood pressure levels and PCa incidence (FIG. 16), which is consistent with studies in humans that showed no relationship between blood pressure and PCa [41, 42].

Another major finding of this study is that the antitumor effects of limiting NPRA expression may be due to a reduction in inflammation in the tumor environment. The evidence herein shows that a number of molecules may be regulated by NPRA signaling including MIF and IL-6, both of which have been implicated in PCa development. Increased MIF mRNA expression and serum MIF levels have been associated with progression of PCa when tumor and benign tissue from matched samples were compared [33, 34, 43]. Elevated IL-6 levels are found in patients with metastatic PCa and are associated with a poor prognosis [44]. Furthermore, aberrant expression of the IL-6 gene and increased production of IL-6 are associated with advanced bone metastasis and increased morbidity [44-47], as well as resistance to chemotherapy [48]. There are three lines of evidence supporting the idea that NPRA is an upstream regulator of MIF in PCa cells: (i) A 2.5-fold reduction in MIF mRNA was found after LPS treatment of NPRA-KO mice compared to WT mice; (ii) MIF expression was detectable in the prostate tissues of TRAMP mice, but not in WT mice; and (iii) NPRA down-regulation reduced MIF expression in cultured TRAMP-C1 cells and xenografts. Consistent with these observations, a PCa TMA stained for NPRA showed expression of MIF.

Since intratumoral expression of MIF was correlated with serum IL-6 in patients with non-small cell lung cancer [49] and IL-6 was shown to be one of the potential MIF-regulated genes in DU145 cells [24], the inventors propose that NPRA can regulate IL-6 in PCa cells via MIF. In support of this hypothesis, the inventors found elevated IL-6 in the serum of TRAMP mice during PCa development. These data support previously reported studies, where lung tissues of NPRA-KO mice failed to induce IL-6 during OVA-induced inflammatory challenge and showed reduced expression of activated p65- and p50-NF-kB [19, 20]. Together, these studies show that NPRA may affect PCa progression by regulating MIF and possibly IL-6 expression, both of which have been linked to PCa.

The results herein demonstrate that increased NPRA expression is strongly associated with progression of human PCa and that NPRA deficiency prevents growth of transplanted PCa cells and inhibits tumor burden in TRAMP mice in part by down-regulating MIF in PCa cells.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Goggins W B, Wong G K: Poor survival for US Pacific Islander cancer patients: evidence from the Surveillance, Epidemiology, and End Results database: 1991 to 2004. *J Clin Oncol* 2007, 25:5738-5741.
2. Miller B A, Chu K C, Hankey B F, Ries L A: Cancer incidence and mortality patterns among specific Asian and Pacific Islander populations in the U.S. *Cancer Causes Control* 2007.
3. De Marzo A M, Nakai Y, Nelson W G: Inflammation, atrophy, and prostate carcinogenesis. *Urol Oncol* 2007, 25:398-400.
4. De Marzo A M, Platz E A, Sutcliffe S, Xu J, Gronberg H, Drake C G, Nakai Y, Isaacs W B, Nelson W G: Inflammation in prostate carcinogenesis. *Nat Rev Cancer* 2007, 7:256-269.
5. Nelson W G: Prostate cancer prevention. *Curr Opin Urol* 2007, 17:157-167.
6. Kelloff G J, Lieberman R, Steele V E, Boone C W, Lubet R A, Kopelovich L, Malone W A, Crowell J A, Higley H R, Sigman C C: Agents, biomarkers, and cohorts for chemopreventive agent development in prostate cancer. *Urology* 2001, 57:46-51.
7. Thun M J, Henley S J, Patrono C: Nonsteroidal anti-inflammatory drugs as anticancer agents: mechanistic, pharmacologic, and clinical issues. *J Natl Cancer Inst* 2002, 94:252-266.
8. Nelson J E, Harris R E: Inverse association of prostate cancer and non-steroidal anti-inflammatory drugs (NSAIDs): results of a case-control study. *Oncol Rep* 2000, 7:169-170.
9. Mohapatra S S, Lockey R F, Vesely D L, Gower W R, Jr.: Natriuretic peptides and genesis of asthma: an emerging paradigm? *J Allergy Clin Immunol* 2004, 114:520-526.
10. Vesely B A, Song S, Sanchez-Ramos J, Fitz S R, Alli A A, Solivan S M, Gower W R, Jr., Vesely D L: Five cardiac hormones decrease the number of human small-cell lung cancer cells. *Eur J Clin Invest* 2005, 35:388-398.
11. Vesely D L: Atrial natriuretic peptide prohormone gene expression: hormones and diseases that upregulate its expression. *IUBMB Life* 2002, 53:153-159.
12. Vesely D L, Perez-Lamboy G I, Schocken D D: Vessel dilator, long acting natriuretic peptide, and kaliuretic peptide increase circulating prostaglandin E2. *Life Sci* 2000, 66:905-913.
13. Kiemer A K, Vollmar A M: The atrial natriuretic peptide regulates the production of inflammatory mediators in macrophages. *Ann Rheum Dis* 2001, 60 Suppl 3:iii68-70.
14. Hellermann G, Kong X, Gunnarsdottir J, San Juan H, Singam R, Behera S, Zhang W, Lockey R F, Mohapatra S S: Mechanism of bronchoprotective effects of a novel natriuretic hormone peptide. *J Allergy Clin Immunol* 2004, 113:79-85.
15. Kumar M. Behera A K, Lockey R F, Vesely D L, Mohapatra S S: Atrial natriuretic peptide gene transfer by means of intranasal administration attenuates airway reactivity in a mouse model of allergic sensitization. *J Allergy Clin Immunol* 2002, 110:879-882.
16. Mohapatra S S: Role of natriuretic peptide signaling in modulating asthma and inflammation. *Can J Physiol Pharmacol* 2007, 85:754-759.
17. Sun Y, Eichelbaum E J, Wang H, Vesely D L: Vessel dilator and kaliuretic peptide inhibit ERK 1/2 activation in human prostate cancer cells. *Anticancer Res* 2006, 26:3217-3222.
18. Sun Y, Eichelbaum E J, Wang F L Vesely D L: Vessel dilator and kaliuretic peptide inhibit MEK 1/2 activation in human prostate cancer cells. *Anticancer Res* 2007, 27:1387-1392.
19. Kong X, Wang X, Xu W, Behera S, Hellermann G, Kumar A, Lockey R F, Mohapatra S, Mohapatra S S:

Natriuretic peptide receptor a as a novel anticancer target. *Cancer Res* 2008, 68:249-256.
20. Wang X, Xu W, Mohapatra S, Kong X, Li X, Lockey R F, Mohapatra S S: Prevention of airway inflammation with topical cream containing imiquimod and small interfering RNA for natriuretic peptide receptor. *Genet Vaccines Ther* 2008, 6:7.
21. Lopez M J, Wong S K, Kishimoto I, Dubois S, Mach V, Friesen J, Garbers D L, Beuve A: Salt-resistant hypertension in mice lacking the guanylyl cyclase-A receptor for atrial natriuretic peptide. *Nature* 1995, 378:65-68.
22. Gower W R, Jr., Carter G M, McAfee Q, Solivan S M: Identification, regulation and anti-proliferative role of the NPR-C receptor in gastric epithelial cells. *Mol Cell Biochem* 2006, 293:103-118.
23. Jiao J, Wang S, Qiao R, Vivanco I, Watson P A, Sawyers C L, Wu H: Murine cell lines derived from Pten null prostate cancer show the critical role of PTEN in hormone refractory prostate cancer development. *Cancer Res* 2007, 67:6083-6091.
24. Meyer-Siegler K L, Iczkowski K A, Leng L, Bucala R, Vera P L: Inhibition of macrophage migration inhibitory factor or its receptor (CD74) attenuates growth and invasion of DU-145 prostate cancer cells. *J Immunol* 2006, 177:8730-8739.
25. Mohapatra S, Chu B, Zhao X, Pledger W J: Accumulation of p53 and reductions in XIAP abundance promote the apoptosis of prostate cancer cells. *Cancer Res* 2005, 65:7717-7723.
26. Foster B A, Gingrich J R, Kwon E D, Madias C, Greenberg N M: Characterization of prostatic epithelial cell lines derived from transgenic adenocarcinoma of the mouse prostate (TRAMP) model. *Cancer Res* 1997, 57:3325-3330.
27. Wang X, Xu W, Kong X, Chen D, Hellermann G, Ahlert T A, Giaimo J D, Cormier S A, Li X, Lockey R F, et al: Modulation of lung inflammation by vessel dilator in a mouse model of allergic asthma. *Respir Res* 2009, 10:66.
28. Le N T, Xue M, Castelnoble L A, Jackson C J: The dual personalities of matrix metalloproteinases in inflammation. *Front Biosci* 2007, 12:1475-1487.
29. He Z, Ong C H, Halper J, Bateman A: Progranulin is a mediator of the wound response. *Nat Med* 2003, 9:225-229.
30. Salama I, Malone P S, Mihaimeed F, Jones J L: A review of the S100 proteins in cancer. *Eur J Surg Oncol* 2008, 34:357-364.
31. Kawada M, Inoue H, Usami I, Takamoto K, Masuda T, Yamazaki Y, Ikeda D: Establishment of a highly tumorigenic LNCaP cell line having inflammatory cytokine resistance. *Cancer Lett* 2006, 242:46-52.
32. Liu X H, Kirschenbaum A, Lu M, Yao S, Klausner A, Preston C, Holland J F, Levine A C: Prostaglandin E(2) stimulates prostatic intraepithelial neoplasia cell growth through activation of the interleukin-6/GP130/STAT-3 signaling pathway. *Biochem Biophys Res Commun* 2002, 290:249-255.
33. Meyer-Siegler K L, Vera P L, Iczkowski K A, Bifulco C, Lee A, Gregersen P K, Leng L, Bucala R: Macrophage migration inhibitory factor (MIF) gene polymorphisms are associated with increased prostate cancer incidence. *Genes Immun* 2007, 8:646-652.
34. Meyer-Siegler K L, Iczkowski K A, Vera P L: Further evidence for increased macrophage migration inhibitory factor expression in prostate cancer. *BMC Cancer* 2005, 5:73.
35. Vesely B A, Alli A A, Song S J, Gower W R, Jr., Sanchez-Ramos J, Vesely D L: Four peptide hormones' specific decrease (up to 97%) of human prostate carcinoma cells. *Eur Clin Invest* 2005, 35:700-710.
36. Bell E N, Tse M Y, Frederiksen L J, Gardhouse A, Pang S C, Graham C H, Siemens D R: Atrial natriuretic peptide attenuates hypoxia induced chemoresistance in prostate cancer cells. *J Urol* 2007, 177:751-756.
37. Sun Y, Eichelbaum E J, Wang H, Vesely D L: Atrial natriuretic peptide and long acting natriuretic peptide inhibit ERK 1/2 in prostate cancer cells. *Anticancer Res* 2006, 26:4143-4148.
38. Cao L, Wu J, Gardner D G: Atrial natriuretic peptide suppresses the transcription of its guanylyl cyclase-linked receptor. *J Biol Chem* 1995, 270:24891-24897.
39. Stark J R, Li H, Kraft P, Kurth T, Giovannucci E L, Stampfer M J, Ma J, Mucci L A: Circulating prediagnostic interleukin-6 and C-reactive protein and prostate cancer incidence and mortality. *Int J Cancer* 2009, 124:2683-2689.
40. Tumminello F M, Badalamenti G, Incorvaia L, Fulfaro F, D'Amico C, Leto G: Serum interleukin-6 in patients with metastatic bone disease: correlation with cystatin C. *Med Oncol* 2009, 26:10-15.
41. Beebe-Dimmer J L, Dunn R L, Sarma A V, Montie J E, Cooney K A: Features of the metabolic syndrome and prostate cancer in African-American men. *Cancer* 2007, 109:875-881.
42. Rodriguez C, Jacobs E J, Deka A, Patel A V, Bain E B, Thun M J, Calle E E: Use of blood-pressure-lowering medication and risk of prostate cancer in the Cancer Prevention Study II Nutrition Cohort. *Cancer Causes Control* 2009, 20:671-679.
43. Mentor-Marcel R, Lamartiniere C A, Eltoum I E, Greenberg N M, Elgavish A: Genistein in the diet reduces the incidence of poorly differentiated prostatic adenocarcinoma in transgenic mice (TRAMP). *Cancer Res* 2001, 61:6777-6782.
44. Michalaki V, Syrigos K, Charles P, Waxman J: Serum levels of IL-6 and TNF-alpha correlate with clinicopathological features and patient survival in patients with prostate cancer. *Br J Cancer* 2004, 90:2312-2316.
45. Paule B, Terry S, Kheuang L, Soyeux P, Vacherot F, de la Taille A: The NF-kappaB/IL-6 pathway in metastatic androgen-independent prostate cancer: new therapeutic approaches? *World J Urol* 2007, 25:477-489.
46. Smith P C, Hobisch A, Lin D L, Culig Z, Keller E T: Interleukin-6 and prostate cancer progression. *Cytokine Growth Factor Rev* 2001, 12:33-40.
47. Smith P C, Keller E T: Anti-interleukin-6 monoclonal antibody induces regression of human prostate cancer xenografts in nude mice. *Prostate* 2001, 48:47-53.
48. Borsellino N, Belldegrun A, Bonavida B: Endogenous interleukin 6 is a resistance factor for cis-diamminedichloroplatinum and etoposide-mediated cytotoxicity of human prostate carcinoma cell lines. *Cancer Res* 1995, 55:4633-4639.
49. Hamatake M, Yoshino 1, Tomiyasu M, Miura N, Okazaki H, Ohba T, Takenaka T, Maehara Y: Intratumoral expression of macrophage migration inhibitory factor is correlated with serum C-reactive protein and interleukin-6 in patients with non-small cell lung cancer. *Surg Today* 2008, 38:921-925.

We claim:

1. A method for predicting progression of a malignancy and prognosing the malignancy in a human subject diagnosed with the malignancy, comprising:
   (a) obtaining a tissue sample suspected of containing malignant cells from the human subject diagnosed with the malignancy;
   (b) determining a level of human natriuretic peptide receptor A (NPRA) protein in the tissue sample using an immunohistochemical assay, wherein the human NPRA protein comprises the amino acid sequence of SEQ ID NO:5, and wherein the immunohistochemical assay comprises: (i) contacting the tissue sample with a polyclonal antibody, or fragment thereof, that binds to the human NPRA protein, forming a complex, wherein the polyclonal antibody, or fragment thereof, is capable of binding to an epitope of mouse NPRA protein within the amino acid sequence of SEQ ID NO:3, and (ii) detecting the complex between the polyclonal antibody, or fragment thereof, and the human NPRA protein;
   (c) comparing the level determined in (b) with a control NPRA level, wherein a high human NPRA protein level is indicative of an unfavorable prognosis and a low human NPRA protein level is indicative of a favorable prognosis; and
   (d) repeating (a)-(c) one or more times over time, to monitor the malignancy over time.

2. The method of claim 1, wherein the tissue sample comprises tumor cells from the human subject.

3. The method of claim 1, wherein a favorable prognosis comprises tumor regression and/or longer survival rates relative to patients with unfavorable prognosis.

4. The method of claim 1, wherein the malignancy is selected from the group consisting of prostate cancer, colon cancer, breast cancer, pancreatic cancer, Merkell cell carcinoma, and gastrointestinal stromal tumor (GIST).

5. The method of claim 1, wherein the malignancy is colon cancer.

6. The method of claim 5, further comprising carrying out at least one confirmatory test for the colon cancer.

7. The method of claim 1, further comprising treating the human subject for the malignancy.

8. The method of claim 1, further comprising communicating the prognosis to the human subject.

9. The method of claim 1, wherein the human subject has undergone initiation of a regimen for treatment of the malignancy prior to said obtaining of (a).

10. The method of claim 9, wherein the control NPRA level is an NPRA level in a tissue sample obtained from the human subject earlier in the treatment regimen.

11. The method of claim 1, wherein the control NPRA level comprises a plurality of control NPRA levels, and wherein each control NPRA level corresponds to a different stage or grade of the malignancy.

12. The method of claim 11, wherein the malignancy is prostate cancer, and wherein the stage or grade of the malignancy comprises a Gleason score.

13. The method of claim 1, wherein the malignancy is prostate cancer.

14. The method of claim 1, wherein the immunohistochemical assay is a tissue microarray.

15. The method of claim 1, further comprising cryopreserving the tissue sample prior to said determining.

16. The method of claim 1, wherein the polyclonal antibody is a rabbit polyclonal antibody.

* * * * *

UNITED STATES PATENT AND TRADEMARK OFFICE
CERTIFICATE OF CORRECTION

Page 1 of 1

PATENT NO. : 10,184,942 B2
APPLICATION NO. : 13/422880
DATED : January 22, 2019
INVENTOR(S) : Subhra Mohapatra and Shyam S. Mohapatra It is certified that error appears in the above-identified patent and that said Letters Patent is hereby corrected as shown below:

In the Specification

Column 12
Line 19, "mrvrerinit" should read --mrvrerlnit--.
Line 27, "aysehrlywp" should read --avsehrlywp--.

Column 17
Line 22, "ccgctactgt" should read --ccgttactgt--.
Line 60, "GI: 67830410" should read --GI:167830410--.

Column 27
Line 16, "selectively hinds" should read --selectively binds--.

Column 35
Line 4, "NPRA (INFRA)" should read --NPRA (iNPRA)--.

Signed and Sealed this
Ninth Day of July, 2019

Andrei Iancu
*Director of the United States Patent and Trademark Office*

SEQUENCE LISTING

<160> NUMBER OF SEQ ID NOS: 6

<210> SEQ ID NO 1
<211> LENGTH: 16
<212> TYPE: PRT
<213> ORGANISM: Artificial sequence
<220> FEATURE:
<223> OTHER INFORMATION: NPRA target sequence of antibody 1

<400> SEQUENCE: 1

Cys Trp Ala Glu Asp Pro Gln Glu Arg Pro Pro Phe Gln Gln Ile Arg
1               5                   10                  15

<210> SEQ ID NO 2
<211> LENGTH: 23
<212> TYPE: PRT
<213> ORGANISM: Artificial sequence
<220> FEATURE:
<223> OTHER INFORMATION: NPRA target sequence of antibody 2

<400> SEQUENCE: 2

Cys Ser Glu Leu Trp Arg Val Arg Trp Glu Asp Leu Gln Pro Ser Ser
1               5                   10                  15

Leu Glu Arg His Leu Arg Ser
            20

<210> SEQ ID NO 3
<211> LENGTH: 22
<212> TYPE: PRT
<213> ORGANISM: Artificial sequence
<220> FEATURE:
<223> OTHER INFORMATION: NPRA target sequence of antibody 3

<400> SEQUENCE: 3

Ile His Leu Ser Ser Glu Thr Lys Ala Val Leu Glu Glu Phe Asp Gly
1               5                   10                  15

Phe Glu Leu Glu Leu Arg
            20

<210> SEQ ID NO 4
<211> LENGTH: 1057
<212> TYPE: PRT
<213> ORGANISM: Mus musculus

<400> SEQUENCE: 4

Met Pro Arg Ser Arg Arg Val Arg Pro Arg Leu Arg Ala Leu Leu Leu
1               5                   10                  15

Leu Pro Pro Leu Leu Leu Leu Arg Ser Gly His Ala Ser Asp Leu Thr
            20                  25                  30

Val Ala Val Val Leu Pro Val Thr Asn Thr Ser Tyr Pro Trp Ser Trp
        35                  40                  45

Ala Arg Val Gly Pro Ala Val Glu Leu Ala Leu Gly Arg Val Lys Ala
    50                  55                  60

Arg Pro Asp Leu Leu Pro Gly Trp Thr Val Arg Met Val Leu Gly Ser
65                  70                  75                  80

Ser Glu Asn Ala Ala Gly Val Cys Ser Asp Thr Ala Ala Pro Leu Ala
                85                  90                  95

Ala Val Asp Leu Lys Trp Glu His Ser Pro Ala Val Phe Leu Gly Pro
            100                 105                 110

Gly Cys Val Tyr Ser Ala Ala Pro Val Asp Arg Phe Thr Ala His Trp
        115                 120                 125

```
Arg Leu Pro Leu Leu Thr Ala Gly Ala Pro Ala Leu Gly Ile Gly Val
130                 135                 140

Lys Asp Glu Tyr Ala Leu Thr Thr Arg Thr Gly Pro Ser His Val Lys
145                 150                 155                 160

Leu Gly Asp Phe Val Thr Ala Leu His Arg Arg Leu Gly Trp Glu His
                165                 170                 175

Gln Ala Leu Val Leu Tyr Ala Asp Arg Leu Gly Asp Arg Pro Cys
            180                 185                 190

Phe Phe Ile Val Glu Gly Leu Tyr Met Arg Val Arg Glu Arg Leu Asn
        195                 200                 205

Ile Thr Val Asn His Gln Glu Phe Val Glu Gly Asp Pro Asp His Tyr
210                 215                 220

Thr Lys Leu Leu Arg Thr Val Gln Arg Lys Gly Arg Val Ile Tyr Ile
225                 230                 235                 240

Cys Ser Ser Pro Asp Ala Phe Arg Asn Leu Met Leu Leu Ala Leu Asp
                245                 250                 255

Ala Gly Leu Thr Gly Glu Asp Tyr Val Phe Phe His Leu Asp Val Phe
            260                 265                 270

Gly Gln Ser Leu Gln Gly Ala Gln Gly Pro Val Pro Glu Lys Pro Trp
        275                 280                 285

Glu Arg Asp Asp Gly Gln Asp Arg Arg Ala Arg Gln Arg Phe Gln Ala
290                 295                 300

Ala Lys Ile Ile Thr Tyr Lys Glu Pro Asp Asn Pro Glu Tyr Leu Glu
305                 310                 315                 320

Phe Leu Lys Gln Leu Lys Leu Leu Ala Asp Lys Lys Phe Asn Phe Thr
                325                 330                 335

Met Glu Asp Gly Leu Lys Asn Ile Ile Pro Ala Ser Phe His Asp Gly
            340                 345                 350

Leu Leu Leu Tyr Val Gln Ala Val Thr Glu Thr Leu Ala Gln Gly Gly
        355                 360                 365

Thr Val Thr Asp Gly Glu Asn Ile Thr Gln Arg Met Trp Asn Arg Ser
370                 375                 380

Phe Gln Gly Val Thr Gly Tyr Leu Lys Ile Asp Arg Asn Gly Asp Arg
385                 390                 395                 400

Asp Thr Asp Ser Pro Leu Trp Asp Met Asp Pro Glu Thr Gly Ala Phe
                405                 410                 415

Arg Val Val Leu Asn Phe Asn Gly Thr Ser Gln Glu Leu Met Ala Val
            420                 425                 430

Ser Glu His Arg Leu Tyr Trp Pro Leu Gly Tyr Pro Pro Pro Asp Ile
        435                 440                 445

Pro Lys Cys Gly Phe Asp Asn Glu Asp Pro Ala Cys Asn Gln Asp His
450                 455                 460

Phe Ser Thr Leu Glu Val Leu Ala Leu Val Gly Ser Leu Ser Leu Val
465                 470                 475                 480

Ser Phe Leu Ile Val Ser Phe Phe Ile Tyr Arg Lys Met Gln Leu Glu
                485                 490                 495

Lys Glu Leu Val Ser Glu Leu Trp Arg Val Arg Trp Glu Asp Leu Gln
            500                 505                 510

Pro Ser Ser Leu Glu Arg His Leu Arg Ser Ala Gly Ser Arg Leu Thr
        515                 520                 525

Leu Ser Gly Arg Gly Ser Asn Tyr Gly Ser Leu Leu Thr Thr Glu Gly
530                 535                 540
```

-continued

Gln Phe Gln Val Phe Ala Lys Thr Ala Tyr Tyr Lys Gly Asn Leu Val
545                 550                 555                 560

Ala Val Lys Arg Val Asn Arg Lys Arg Ile Glu Leu Thr Arg Lys Val
                565                 570                 575

Leu Phe Glu Leu Lys His Met Arg Asp Val Gln Asn Glu Gln Leu Thr
            580                 585                 590

Arg Phe Val Gly Ala Cys Thr Asp Pro Pro Asn Ile Cys Ile Leu Thr
        595                 600                 605

Glu Tyr Cys Pro Arg Gly Ser Leu Gln Asp Ile Leu Glu Asn Glu Ser
    610                 615                 620

Ile Thr Leu Asp Trp Met Phe Arg Tyr Ser Leu Thr Asn Asp Ile Val
625                 630                 635                 640

Lys Gly Met Leu Phe Leu His Asn Gly Ala Ile Cys Ser His Gly Asn
                645                 650                 655

Leu Lys Ser Ser Asn Cys Val Val Asp Gly Arg Phe Val Leu Lys Ile
                660                 665                 670

Thr Asp Tyr Gly Leu Glu Ser Phe Arg Asp Pro Glu Pro Glu Gln Gly
            675                 680                 685

His Thr Leu Phe Ala Lys Lys Leu Trp Thr Ala Pro Glu Leu Leu Arg
        690                 695                 700

Met Ala Ser Pro Pro Ala Arg Gly Ser Gln Ala Gly Asp Val Tyr Ser
705                 710                 715                 720

Phe Gly Ile Ile Leu Gln Glu Ile Ala Leu Arg Ser Gly Val Phe Tyr
                725                 730                 735

Val Glu Gly Leu Asp Leu Ser Pro Lys Glu Ile Ile Glu Arg Val Thr
            740                 745                 750

Arg Gly Glu Gln Pro Pro Phe Arg Pro Ser Met Asp Leu Gln Ser His
        755                 760                 765

Leu Glu Glu Leu Gly Gln Leu Met Gln Arg Cys Trp Ala Glu Asp Pro
770                 775                 780

Gln Glu Arg Pro Pro Phe Gln Gln Ile Arg Leu Ala Leu Arg Lys Phe
785                 790                 795                 800

Asn Lys Glu Asn Ser Ser Asn Ile Leu Asp Asn Leu Leu Ser Arg Met
                805                 810                 815

Glu Gln Tyr Ala Asn Asn Leu Glu Glu Leu Val Glu Glu Arg Thr Gln
            820                 825                 830

Pro Tyr Leu Glu Glu Lys Arg Lys Ala Glu Ala Leu Leu Tyr Gln Ile
        835                 840                 845

Leu Pro His Ser Val Ala Glu Gln Leu Lys Arg Gly Glu Thr Val Gln
850                 855                 860

Ala Glu Ala Phe Asp Ser Val Thr Ile Tyr Phe Ser Asp Ile Val Gly
865                 870                 875                 880

Phe Thr Ala Leu Ser Ala Glu Ser Thr Pro Met Gln Val Val Thr Leu
                885                 890                 895

Leu Asn Asp Leu Tyr Thr Cys Phe Asp Ala Val Ile Asp Asn Phe Asp
            900                 905                 910

Val Tyr Lys Val Glu Thr Ile Gly Asp Ala Tyr Met Val Val Ser Gly
        915                 920                 925

Leu Pro Val Arg Asn Gly Gln Leu His Ala Arg Glu Val Ala Arg Met
930                 935                 940

Ala Leu Ala Leu Leu Asp Ala Val Arg Ser Phe Arg Ile Gly His Arg
945                 950                 955                 960

```
Pro Gln Glu Gln Leu Arg Leu Arg Ile Gly Ile His Thr Gly Pro Val
                965                 970                 975

Cys Ala Gly Val Val Gly Leu Lys Met Pro Arg Tyr Cys Leu Phe Gly
            980                 985                 990

Asp Thr Val Asn Thr Ala Ser Arg  Met Glu Ser Asn Gly  Glu Ala Leu
        995                 1000                1005

Arg Ile His Leu Ser Ser Glu  Thr Lys Ala Val Leu  Glu Glu Phe
        1010                1015                1020

Asp Gly  Phe Glu Leu Glu Leu  Arg Gly Asp Val Glu  Met Lys Gly
        1025                1030                1035

Lys Gly  Lys Val Arg Ser Tyr  Trp Leu Leu Gly Asp  Arg Gly Cys
        1040                1045                1050

Ser Ser  Arg Ala
        1055

<210> SEQ ID NO 5
<211> LENGTH: 415
<212> TYPE: PRT
<213> ORGANISM: Homo sapiens

<400> SEQUENCE: 5

Met Phe Arg Tyr Ser Leu Thr Asn Asp Ile Val Lys Gly Met Leu Phe
1               5                   10                  15

Leu His Asn Gly Ala Ile Cys Ser His Gly Asn Leu Lys Ser Ser Asn
            20                  25                  30

Cys Val Val Asp Gly Arg Phe Val Leu Lys Ile Thr Asp Tyr Gly Leu
        35                  40                  45

Glu Ser Phe Arg Asp Leu Asp Pro Glu Gln Gly His Thr Val Tyr Ala
50                  55                  60

Lys Lys Leu Trp Thr Ala Pro Glu Leu Leu Arg Met Ala Ser Pro Pro
65                  70                  75                  80

Val Arg Gly Ser Gln Ala Gly Asp Val Tyr Ser Phe Gly Ile Ile Leu
                85                  90                  95

Gln Glu Ile Ala Leu Arg Ser Gly Val Phe His Val Glu Gly Leu Asp
            100                 105                 110

Leu Ser Pro Lys Glu Ile Ile Glu Arg Val Thr Arg Gly Glu Gln Pro
        115                 120                 125

Pro Phe Arg Pro Ser Leu Ala Leu Gln Ser His Leu Glu Glu Leu Gly
        130                 135                 140

Leu Leu Met Gln Arg Cys Trp Ala Glu Asp Pro Gln Glu Arg Pro Pro
145                 150                 155                 160

Phe Gln Gln Ile Arg Leu Thr Leu Arg Lys Phe Asn Arg Glu Asn Ser
                165                 170                 175

Ser Asn Ile Leu Asp Asn Leu Leu Ser Arg Met Glu Gln Tyr Ala Asn
            180                 185                 190

Asn Leu Glu Glu Leu Val Glu Glu Arg Thr Gln Ala Tyr Leu Glu Glu
        195                 200                 205

Lys Arg Lys Ala Glu Ala Leu Leu Tyr Gln Ile Leu Pro His Ser Val
        210                 215                 220

Ala Glu Gln Leu Lys Arg Gly Glu Thr Val Gln Ala Glu Ala Phe Asp
225                 230                 235                 240

Ser Val Thr Ile Tyr Phe Ser Asp Ile Val Gly Phe Thr Ala Leu Ser
                245                 250                 255

Ala Glu Ser Thr Pro Met Gln Val Val Thr Leu Leu Asn Asp Leu Tyr
            260                 265                 270
```

```
Thr Cys Phe Asp Ala Val Ile Asp Asn Phe Asp Val Tyr Lys Val Glu
            275                 280                 285

Thr Ile Gly Asp Ala Tyr Met Val Val Ser Gly Leu Pro Val Arg Asn
        290                 295                 300

Gly Arg Leu His Ala Cys Glu Val Ala Arg Met Ala Leu Ala Leu Leu
305                 310                 315                 320

Asp Ala Val Arg Ser Phe Arg Ile Arg His Arg Pro Gln Glu Gln Leu
                325                 330                 335

Arg Leu Arg Ile Gly Ile His Thr Gly Pro Val Cys Ala Gly Val Val
                340                 345                 350

Gly Leu Lys Met Pro Arg Tyr Cys Leu Phe Gly Asp Thr Val Asn Thr
            355                 360                 365

Ala Ser Arg Met Glu Ser Asn Gly Glu Ala Leu Lys Ile His Leu Ser
        370                 375                 380

Ser Glu Thr Lys Ala Val Leu Glu Gln Phe Gly Gly Phe Glu Leu Glu
385                 390                 395                 400

Leu Arg Gly Asp Val Glu Met Lys Gly Lys Gly Lys Val Arg Thr
                405                 410                 415
```

<210> SEQ ID NO 6
<211> LENGTH: 4201
<212> TYPE: DNA
<213> ORGANISM: Homo sapiens

<400> SEQUENCE: 6

```
acactccctg gggcaggcgc tcacgcacgc tacaaacaca cactcctctt tcctccctcg      60
cgcgccctct ctcatccttc ttcacgaagc gctcactcgc accctttctc tctctctctc     120
tctctctcta acacgcacgc acactcccag ttgttcacac tcgggtcctc tccagcccga     180
cgttctcctg gcacccacct gctccgcggc gccctgcgcg ccccctcgg tcgcgcccct      240
tgcgctctcg gccagaccg tgcagctac agggggcctc gagccccggg gtgagcgtcc       300
ccgtcccgct cctgctcctt cccatagggga gcgcgcctgat gcctgggacc ggccgctgag   360
cccaagggga ccgaggaggc catggtagga gcgctcgcct gctgcggtgc ccgctgaggc     420
catgccgggg ccccggcgcc ccgctggctc ccgcctgcgc ctgctcctgc tcctgctgct     480
gccgccgctg ctgctgctgc tccggggcag ccacgcgggc aacctgacgg tagccgtggt     540
actgccgctg ccaataacct cgtacccctg gtcgtgggcg cgcgtgggac ccgccgtgga    600
gctggccctg gcccaggtga aggcgcgccc cgacttgctg ccgggctgga cggtccgcac     660
ggtgctgggc agcagcgaaa acgcgctggg cgtctgctcc gacaccgcag cgcccctggc    720
cgcggtggac tcaagtgggg agcacaaccc cgctgtgttc ctgggccccg gctgcgtgta    780
cgccgccgcc ccagtggggc gcttcaccgc gcactggcgg gtcccgctgc tgaccgccgg    840
cgccccggcg ctgggcttcg gtgtcaagga cgagtatgcg ctgaccaccc gcgcggggcc    900
cagctacgcc aagctggggg acttcgtggc ggcgctgcac cgacggctgg gctgggagcg    960
ccaagcgctc atgctctacg cctaccggcc gggtgacgaa gagcactgct tcttcctcgt   1020
ggagggggctg ttcatgcggg tccgcgaccg cctcaatatt acgtggacc acctggagtt    1080
cgccgaggac gacctcagcc actacaccag gctgctgcgg accatgccgc gcaaaggccg   1140
agttatctac atctgcagct cccctgatgc cttcagaacc tcatgctcc tggccctgga     1200
agctggcttg tgtggggagg actacgtttt cttccacctg gatatctttg ggcaaagcct   1260
gcaaggtgga cagggccctg ctccccgcag gccctgggag agagggggatg gcaggatgt    1320
```

```
cagtgcccgc caggcctttc aggctgccaa atcattaca tataaagacc cagataatcc  1380
cgagtacttg gaattcctga agcagttaaa acacctggcc tatgagcagt tcaacttcac  1440
catggaggat ggcctggtga acaccatccc agcatccttc cacgacgggc tcctgctcta  1500
tatccaggca gtgacggaga ctctggcaca tgggggaact gttactgatg gggagaacat  1560
cactcagcgg atgtggaacc gaagctttca aggtgtgaca ggatacctga aaattgatag  1620
cagtggcgat cgggaaacag acttctccct ctgggatatg gatcccgaga atggtgcctt  1680
cagggttgta ctgaactaca atgggacttc caagagctg gtggctgtgt cggggcgcaa   1740
actgaactgg cccctggggt accctcctcc tgacatcccc aaatgtggct ttgacaacga  1800
agacccagca tgcaaccaag atcacctttc caccctggag gtgctggctt tggtgggcag  1860
cctctccttg ctcggcattc tgattgtctc cttcttcata tacaggaaga tgcagctgga  1920
gaaggaactg gcctcggagc tgtggcgggt gcgctgggag gacgttgagc ccagtagcct  1980
tgagaggcac ctgcggagtg caggcagccg gctgacccctg agcggagag gctccaatta  2040
cggctccctg ctaaccacag agggccagtt ccaagtcttt gccaagacag catattataa  2100
gggcaacctc gtggctgtga aacgtgtgaa ccgtaaacgc attgagctga cacgaaaagt  2160
cctgtttgaa ctgaagcata tgcgggatgt gcagaatgaa cacctgacca ggtttgtggg  2220
agcctgcacc gaccccccca atatctgcat cctcacagag tactgtcccc gtgggagcct  2280
gcaggacatt ctggagaatg agagcatcac cctggactgg atgttccggt actcactcac  2340
caatgacatc gtcaagggca tgctgttct acacaatggg gctatctgtt cccatgggaa  2400
cctcaagtca tccaactgcg tggtagatgg gcgctttgtg ctcaagatca ccgactatgg  2460
gctggagagc ttcagggacc tggacccaga gcaaggacac accgtttatg ccaaaaagct  2520
gtggacggcc cctgagctcc tgcgaatggc ttcacccccct gtgcggggct cccaggctgg  2580
tgacgtatac agctttggga tcatccttca ggagattgcc ctgaggagtg ggtcttcca   2640
cgtggaaggt ttggacctga gccccaaaga gatcatcgag cgggtgactc ggggtgagca  2700
gccccccttc cggcccctcc tggccctgca gagtcacctg gaggagttgg ggctgctcat  2760
gcagcggtgc tgggctgagg acccacagga gaggccacca ttccagcaga tccgcctgac  2820
gttgcgcaaa tttaacaggg agaacagcag caacatcctg gacaacctgc tgtcccgcat  2880
ggagcagtac gcgaacaatc tggaggaact ggtggaggag cggacccagg catacctgga  2940
ggagaagcgc aaggctgagg ccctgctcta ccagatcctg cctcactcag tggctgagca  3000
gctgaagcgt ggggagacgg tgcaggccga agcctttgac agtgttacca tctacttcag  3060
tgacattgtg ggtttcacag cgctgtcggc ggagagcaca cccatgcagg tggtgaccct  3120
gctcaatgac ctgtacactt gctttgatgc tgtcatagac aactttgatg tgtacaaggt  3180
ggagacaatt ggcgatgcct acatggtggt gtcagggctc cctgtgcgga acgggcggct  3240
acacgcctgc gaggtagccc gcatggccct ggcactgctg gatgctgtgc gctccttccg  3300
aatccgccac cggccccagg agcagctgcg cttgcgcatt ggcatccaca caggacctgt  3360
gtgtgctgga gtggtgggac tgaagatgcc ccgttactgt ctctttgggg atacagtcaa  3420
cacagcctca agaatggagt ctaatgggga agccctgaag atccacttgt cttctgagac  3480
caaggctgtc ctggaggagt ttggtggttt cgagctggag cttcgagggg atgtagaaat  3540
gaagggcaaa gcaaggttc ggaccctactg gctccttggg gagagggggga gtagcacccg  3600
aggctgacct gcctcctctc ctatccctcc acacctccct accctgtgcc agaagcaaca  3660
gaggtgccag gcctcagcct cacccacagc agccccatcg ccaaaggatg gaagtaattt  3720
```

-continued

```
gaatagctca ggtgtgctga ccccagtgaa gacaccagat aggacctctg agagggact    3780 ggcatggggg gatctcagag cttacaggct gagccaagcc cacggccatg cacagggaca   3840
ctcacacagg cacacgcacc tgctctccac ctggactcag gccgggctgg gctgtggatt   3900
cctgatcccc tcccctcccc atgctctcct ccctcagcct tgctaccctg tgacttactg   3960
ggaggagaaa gagtcacctg aaggggaaca tgaaaagaga ctaggtgaag agagggcagg   4020
ggagcccaca tctggggctg gcccacaata cctgctcccc cgaccccctc cacccagcag   4080
tagacacagt gcaggggga gaagagggt ggcgcagaag ggttgggggc ctgtatgcct     4140
tgcttctacc atgagcagag acaattaaaa tctttattcc agtgaaaaaa aaaaaaaaaa   4200
a                                                                   4201
```